(12) United States Patent
Suda

(10) Patent No.: US 8,765,384 B2
(45) Date of Patent: *Jul. 1, 2014

(54) CARBOHYDRATE-LIGAND CONJUGATES AND THEIR APPLICATION FOR THE ANALYSIS OF CARBOHYDRATE-PROTEIN INTERACTION

(75) Inventor: Yasuo Suda, Kagoshima (JP)

(73) Assignees: Japan Science and Technology Agency, Saitama (JP); National University Corporation Kagoshima University, Kagoshima (JP)

( * ) Notice: Subject to any disclaimer, the term of this patent is extended or adjusted under 35 U.S.C. 154(b) by 2049 days.

This patent is subject to a terminal disclaimer.

(21) Appl. No.: 10/590,045

(22) PCT Filed: Feb. 18, 2005

(86) PCT No.: PCT/JP2005/003220
§ 371 (c)(1),
(2), (4) Date: Jul. 17, 2007

(87) PCT Pub. No.: WO2005/077965
PCT Pub. Date: Aug. 25, 2005

(65) Prior Publication Data
US 2007/0287195 A1     Dec. 13, 2007

(30) Foreign Application Priority Data
Feb. 18, 2004   (JP) ................. 2004-041994

(51) Int. Cl.
*G01N 33/53* (2006.01)
*G01N 33/532* (2006.01)
*G01N 33/553* (2006.01)

(52) U.S. Cl.
USPC ............ 435/7.1; 435/7.92; 436/544; 436/525

(58) Field of Classification Search
None
See application file for complete search history.

(56) References Cited

U.S. PATENT DOCUMENTS

| | | | |
|---|---|---|---|
| 5,955,729 A | 9/1999 | Nelson et al. | |
| 6,821,529 B2 | 11/2004 | Nelson | |
| 2006/0030699 A1 | 2/2006 | Suda et al. | |
| 2007/0213523 A1 | 9/2007 | Suda et al. | |

FOREIGN PATENT DOCUMENTS

| | | | | |
|---|---|---|---|---|
| EP | 1538156 A1 | 6/2005 | | |
| EP | 1548016 A1 | 6/2005 | | |
| JP | 2002022745 A | * | 1/2002 | ........... G01N 33/566 |
| JP | 2002080488 | 3/2002 | | |
| JP | 2003083969 | 3/2003 | | |
| JP | 2004157108 | 6/2004 | | |
| TW | 200530151 | 9/2005 | | |
| WO | WO-9709608 | 3/1997 | | |
| WO | WO-2004/022583 A | 3/2004 | | |

OTHER PUBLICATIONS

Fazio et al. Synthesis of sugar arrays in microtiter plate. J. Am. CHem. Soc. 2002, vol. 124, pp. 14397-14402.*
Arano, Akio et al. "Analysis of Binding Interaction Between Glycosaminoglycans and Proteins Using Surface Plasmon Resonance," Annual Meeting Syllabus of the Japanese Society of Carbohydrate Research, vol. 22, 4 pages.
Liedberg, B. et al. (1995). "Biosensing with surface plasmon resonance—how it all started," Biosensors & Bioelectronics 10:i-ix.
Plant, A.L. et al. (1995). "Phospholipid/Alkanethiol Bilayers for Cell-Surface Receptor Studies by Surface Plasmon Resonance," Analytical Biochemistry, 226:342-348.
Horan, N. et al. (1999). "Nonstatistical binding of a protein to clustered carbohydrates," PNAS, 96(21):11782-11786.
Arano, Akio et al. (2001). "Synthesis of a conjugate having heparin partial structure and a distal disulfide group and its application to chip technology," Chemical Society of Japan, Tentative Lecture Proceedings II in the 79th Spring Meeting, Mar. 15, 2001, 3 pages (4G305).
Kideki et al. (2001). "Assembly of saccharide by multi-functional linker and application to surface plasmon resonance analysis and affinity chromatography," Tentative Lecture Proceedings, Chemical Society of Japan, vol. 83, 3 pages.
Arano, Akio et al. (2002) "Preparation of novel clustered oligosaccharide-ligand containing multi-units of heparin partial structure and its application for chip technology," The Chemical Society of Japan, the 82nd Fall Meeting, Sep. 10, 2002, 3 pages.
Fazio, F. et al. (2002). "Synthesis of Sugar Arrays in Microtiter Plate," J. Am. Chem. Soc., 124:14397-14402.

(Continued)

*Primary Examiner* — Shafiqul Haq
(74) *Attorney, Agent, or Firm* — Morrison & Foerster LLP

(57) ABSTRACT

A novel ligand conjugate which is effectively utilizable for analyzing a function of a protein; a ligand-supporting object; and a method of analyzing a protein. The ligand conjugate has a structure which comprises: a linker compound having a structure represented by the following General Formula (1):

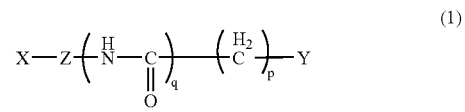

(wherein n and p each is an integer of 0 to 6) in which X is a structure comprising one, two, or three hydrocarbon derivative chains which have an aromatic amino group at the end and may have a carbon-nitrogen bond in the main chain, Y is a hydro-carbon structure containing one or more sulfur atoms, and Z is a straight-chain structure comprising a carbon-carbon bond or carbon-oxygen bond; and a sugar which has a reducing end and is bonded to the linker compound through the aromatic amino group.

7 Claims, 23 Drawing Sheets

(56) References Cited

OTHER PUBLICATIONS

Fukui, S. et al. (2002). "Oligosaccharide microarrays for high-throughput detection and specificity assignments of carbohydrate-protein interactions," Nature Biotechnology, 20:1011-1017.

Houseman, B. et al. (2002). "Carbohydrate Arrays for the Evaluation of Protein Binding and Enzymatic Modification," Chemistry & Biology, 9:443-454.

Wang, D. et al. (2002). "Carbohydrate microarrays for the recognition of cross-reactive molecular markers of microbes and host cells," Nature Biotechnology, 20:275-281.

Arano, Akio et al. (2003) "Preparation of Sugar Chips Immobilized with Clustered Sulfated Oligosaccharides and their Application of Surface Plasmon Resonance," The Japanese Society of Carbohydrate Research, vol. 24, 7 pages.

Hayashi et al. (2003). "Synthesis, designed assembly and biotinylation of sulfated oligosaccharide and its application to surface plasmon resonance," Tentative Lecture Proceedings, Chemical Society of Japan, 3 pages.

Suda, Yasuo et al. (2003). "Development of Analytical System for the Function of Oligosaccharides at Nanometer Scale," Annual Meeting Syllabus of the Japanese Society of Carbohydrate Research, vol. 24, 7 pages.

Feizi, T. et al. (2004). "Oligosaccharide microarrays to decipher the glycol code," Nature, 5:582-588.

Kato, M. et al. (2004). "Using Model Substrates to Study the Dependence of Focal Adhesion Formation on the Affinity of Integrin-Ligand Complexes," Biochemistry, 43:2699-2707.

Ratner, D.M. et al. (2004). "Probing Protein-Carbohydrate Interactions with Microarrys of Synthetic Oligosaccharides," ChemBioChem, 5:379-383.

Suda, Yasuo (2004). "Sugar Chip: Novel Bio Device for Finding Out Biofunction of Oligosaccharides," Polymer Preprints, Japan, vol. 52, 11 pages.

Park, S. et al. (2004). "Carbohydrate Chips for Studying High-Throughput Carbohydrate-Protein Interactions," J. Am. Chem. Soc., 126:4812-4819.

Karamanska, R. et al. (2005). "Thioctic acid amides: convenient tethers for achieving low nonspecific protein binding to carbohydrates presented on gold surfaces," Chem. Commun., pp. 3334-3336.

European Search Report mailed Jul. 24, 2009, for EP Application No. 05710751.8 filed Feb. 18, 2005, 4 pages.

Fukase, K. et al. (Jan. 1, 1994). "Functional Fluorescence labeling of carbohydrates and its use for preparation of neoglycoconjugates," *Journal of Carbohydrate Chemistry* 13(5):715-736.

Hayashi, K. et al. (Sep. 10, 2002). "Synthesis of a novel linker molecule for assembly and immobilization of reducing saccharides," *Chemical Society of Japan Koen Yokoshu* 82(1 C1-C2):137.

Office Action received for U.S. Appl. No. 10/588,612, mailed on Dec. 30, 2009, 19 pages.

Response to Office Action mailed on Dec. 30, 2009 for U.S. Appl. No. 10/588,612, dated May 17, 2010, 16 pages.

Response to Notice of Non-compliant Amendment for U.S. Appl. No. 10/588,612, dated May 28, 2010, 14 pages.

Notice of Allowance received for U.S. Appl. No. 10/588,612, mailed on Jul. 12, 2010, 9 pages.

Amendment After Allowance for U.S. Appl. No. 10/588,612, dated Aug. 27, 2010, 15 pages.

International Search Report mailed Mar. 15, 2005, for International Patent Application No. PCT/JP2005/001726, filed Feb. 4, 2005. 2 pages.

Supplementary EP Search Report for European Patent Application No. 0570975.1, mailed Aug. 27, 2007. 3 pages.

\* cited by examiner

CARBOHYDRATE-LIGAND CONJUGATES AND THEIR APPLICATION FOR THE ANALYSIS OF CARBOHYDRATE-PROTEIN INTERACTION

CROSS REFERENCE TO RELATED APPLICATIONS

This application is a 35 U.S.C. §371 National Stage filing of International Patent Application No. PCT/JP2005/003220, titled SUGAR CHAIN LIGAND COMPOSITE AND METHOD OF ANALYZING PROTEIN WITH THE LIGAND COMPOSITE, filed Feb. 18, 2005, which claims priority to Japanese Patent No. 2004/041994, filed Feb. 18, 2004, both of which are incorporated herein by reference in their entirety.

TECHNICAL FIELD

The present invention relates to a novel ligand conjugate in which a sugar chain having a reducing end is introduced to a linker compound, and to a ligand carrier which is a chip on which a large number of molecules of the ligand conjugate are immobilized, the chip having a surface coated with a metal such as gold, silver, copper, or the like. Further, the present invention relates to a method for performing protein analysis using the ligand conjugate.

BACKGROUND ART

Various intravital sugar chains play an important role in a mechanism for sustaining activities and lives of living organisms. In order to specifically clarify the functions of such sugar chains, it is necessary to analyze the functions of the sugar chains based on a conjugate structure thereof. Functional analysis of the sugar chains is carried out by the following technique. The structure of a sugar chain is reproduced part by part by using oligosaccharide whose structure is elucidated, so as to clarify the relation between the structure of a whole sugar chain and its functions.

As the technique of the functional analysis of sugar chains, the surface plasmon resonance (hereinafter referenced to as SPR) method is known, for example. That is, the ligand conjugate containing the oligosaccharide which imitates a part of sugar chain is immobilized on the sensor chip surface. By using the sensor chip having oligosaccharide immobilized thereon, a substance, such as protein, which specifically interacts with an oligosaccharide are identified. This makes it possible to properly evaluate a biological activity based on the structure of the oligosaccharide.

Meanwhile, a single oligosaccharic molecule is not active enough. Therefore, it is necessary to implement a large number of molecules of oligosaccharide onto the sensor chip when evaluating a biological activity of an oligosaccharide. In other words, the use of a large number of molecules of oligosaccharide for analysis of interaction with a protein allows for evaluation of biological activity of oligosaccharide.

In view of this, the inventor of the present invention and the others have so far found a linker compound including molecules having therein (i) moiety capable of being immobilizable onto the surface of the sensor chip and (ii) moiety capable of taking in one or two units of oligosaccharide. Also, the inventor of the present invention and the other have so far found a ligand conjugate which includes the linker compound having one or two units of sugar chains of oligosaccharide introduced thereinto. Then, the inventor of the present invention and the others found that the use of such a ligand conjugate makes it possible to introduce a large number of molecules of oligosaccharide onto the sensor chip (for example, see Patent literature 1, Non-patent literature 1).

[Patent Literature 1]
Japanese Unexamined Patent Publication No. 836969/2003 (Tokukai 2003-836969; published on Mar. 19, 2003)

[Non-Patent Literature 1]
Tentative Lecture Proceedings II in the 79th Spring Meeting, Chemical Society of Japan, Mar. 15, 2001, p. 1042

However, the ligand conjugates described in the literatures are such that sugar (oligosaccharides) introducible to the ligand conjugates are limited to sulfated sugar synthesized by the inventor of the present invention and the others. The literatures does not describe whether or not commercially-available oligosaccharides having a reducing end, such as maltose, lactose, and the like, can be introduced into the ligand conjugate to form a sensor therewith. Moreover, it has been proposed to carry out the SPR measurement and then protein identification with the same sensor chip having the ligand conjugate described in the literatures immobilized thereon, in order to identify a protein bonded with the sugar chain on the chip. However, no technique that can give satisfactory data has not been established.

The present invention is accomplished in view of the aforementioned problems, and has an object to provide a novel ligand conjugate in which a commercially-available sugar having a reducing end is introduced, and a ligand carrier which can be used for protein identification.

DISCLOSURE OF INVENTION

As a result of diligent study to solve the above-mentioned problems, the inventor of the present invention reacted, with commercially-available maltose or lactose, a linker compound described in the earlier application (Japanese Patent Application No.: Tokugan 2003-190568, Japanese Unexamined Patent Publication No.: Tokukai 2004-157108 (published on Jun. 3, 2004 which was after the priority date of the present application (Feb. 18, 2004)), thereby synthesizing a ligand conjugate that has α-glucopyranose, or β-galactopyranose at its end. Further, the inventor of the present invention produced sugar chips (ligand carriers) by immobilizing the ligand conjugates on gold-coating chips, respectively. The inventor of the present invention studied interaction of the sugar chips with protein by performing MALDI-TOF/MS with the sugar chips after confirming the interaction by SPR analysis. As a result, the inventor of the present invention found that it is possible to identify the protein bound on the sugar chips by perfuming such analysis. The present invention is accomplished based on these findings.

A ligand conjugate according to the present invention includes a linker compound and a sugar, the linker compound having a structure represented by General Formula (1):

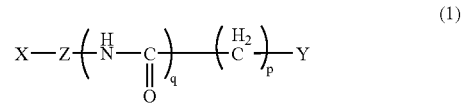

(1)

where p and q are independently integers of not less than 0 but not more than 6, in which X is a structure comprising one, two, or three hydrocarbon derivative chains which have an aromatic amino group at an end and may have a carbon-nitrogen bond in a main chain, Y is a sulfur atom or a hydrocarbon structure containing a sulfur atom, and Z is a straight-chain structure comprising a carbon-carbon bond or carbon-oxygen bond, the sugar having a reducing end and being bonded to the linker compound through the aromatic amino group.

The "hydrocarbon derivative chain" is a hydrocarbon chain made of carbons and hydrogens, wherein part of the carbons and hydrogens may be substituted with another or other atoms, or a substituent(s). That is, the hydrocarbon derivative chain, which has an aromatic amino group at the end, may be such that part of carbon-carbon bonds (C—C bond) that constitute the main chain structure of the hydrocarbon chain is substituted with carbon-nitrogen bond (C—N bond), carbon-oxygen bond (C—O bond), or amide bond (CO—NH bond).

Moreover, the "hydrocarbon structure having a sulfur atom" is a hydrocarbon structure made of carbons and hydrogens, wherein part of the carbons is substituted with sulfur(s). The hydrocarbon structure having a sulfur atom may be a chain (straight or branched), a ring, or a structure having a chain and ring structures.

The ligand conjugate according to the present invention may be arranged such that Y is a hydrocarbon structure having a S—S bond or a SH group. That is, the hydrocarbon structure having a sulfur atom may have a disulfide bond (S—S bond) or thiol group (SH group).

The ligand conjugate according to the present invention may be such that X has a structure represented by General Formula (2):

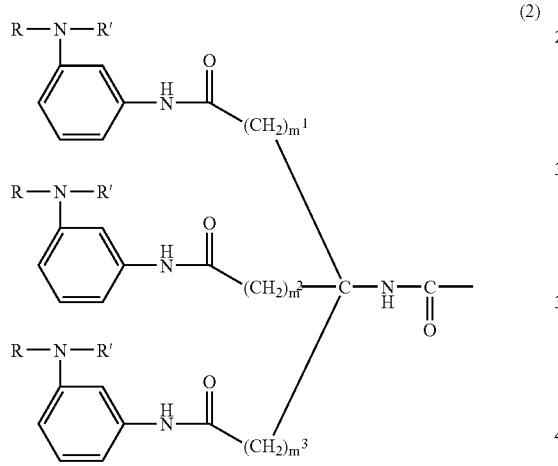

(2)

where $m^1$, $m^2$, and $m^3$ are independently integers of not less than 0 but not more than 6, and R' is a hydrogen (H) or R, R being a compound derived from a sugar chain.

The ligand conjugate according to the present invention may be such that X has a structure represented by General Formula (3):

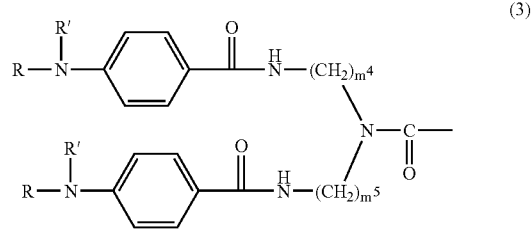

(3)

where $m^4$ and $m^5$ are independently integers of not less than 0 but not more than 6, R' is a hydrogen (H) or R, R being a compound derived from a sugar chain.

The ligand conjugate according to the present invention may be arranged such that X has a structure represented by General Formula (4):

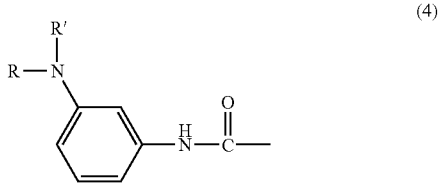

(4)

where R' is a hydrogen (H), or R, R being a compound derived from a sugar chain.

The ligand conjugate according to the present invention may be arranged such that Z has a structure of Formula (5) or (6):

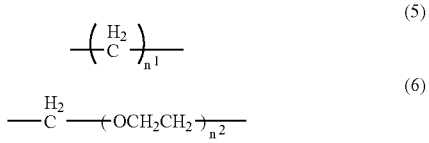

(5)

(6)

where $n^1$ and $n^2$ are independently integers of not less than 1 but not more than 6.

A method according to the present invention for producing a ligand conjugate includes performing reductive amination using a linker compound and a sugar that has a reducing end, the linker compound being any one of:

a linker compound having a structure represented by General Formula (7):

(7)

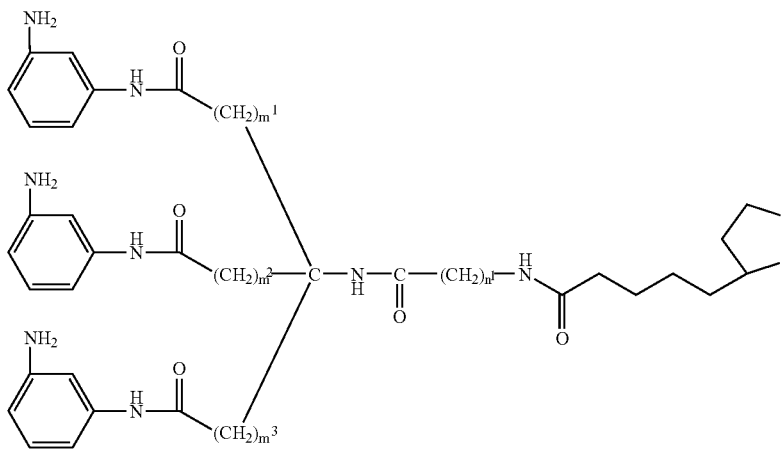

where $m^1$, $m^2$, and $m^3$ are independently integers of not less than 0 but not more than 6, and $n^1$ is an integer not less than 1 but not more than 6;

a linker compound having a structure represented by General Formula (8):

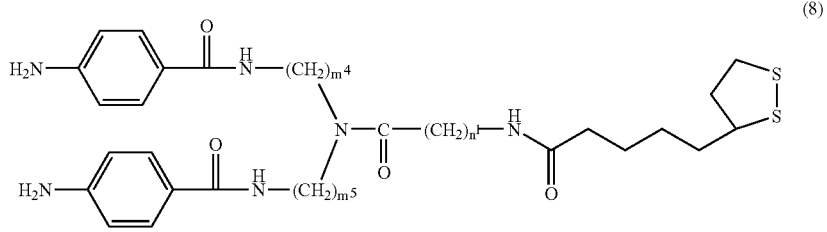

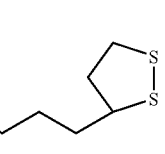

where $m^4$ and $m^5$ are independently integers of not less than 0 but not more than 6, and $n^1$ is an integer of not less than 1 but not more than 6;

a linker compound having a structure represented by General Formula (9):

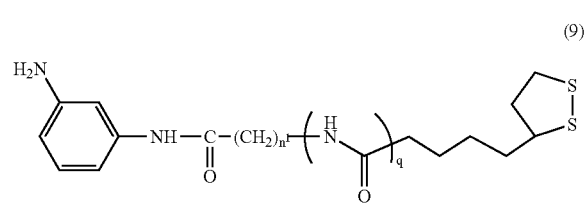

where $n^1$ and q are independently integers of not less than 0 but not more than 6;

a linker compound having a structure represented by General Formula (10):

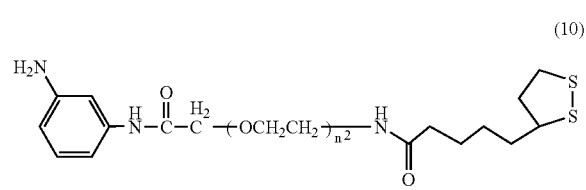

where $n^2$ is an integer of not less than 1 but not more than 6; and a linker compound having a structure represented by General Formula (11):

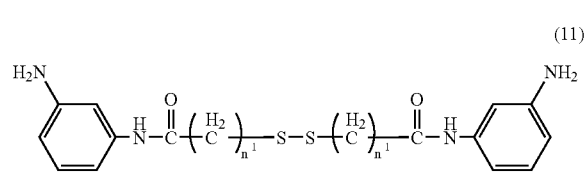

where $n^1$ is an integer of not less than 1 but not more than 6.

Moreover, a ligand carrier according to the present invention is such that any one of the ligand conjugates mentioned above is immobilized on a supporter having a metal on a surface thereof. The ligand carrier may be used for protein analysis.

Moreover, a method according to the present invention for analyzing protein, includes (i) allowing any one of the ligand conjugates mentioned above to stand in contact with a supporter so as to prepare a ligand carrier in which the ligand conjugate is immobilized on the supporter; (ii) analyzing intermolecular interaction after allowing the ligand carrier to stand in contact with a protein solution; and (iii) performing mass spectroscopy after the analysis of the intermolecular interaction, so as to identify a protein bound on the ligand carrier.

BEST MODE FOR CARRYING OUT THE INVENTION

Figure 1:
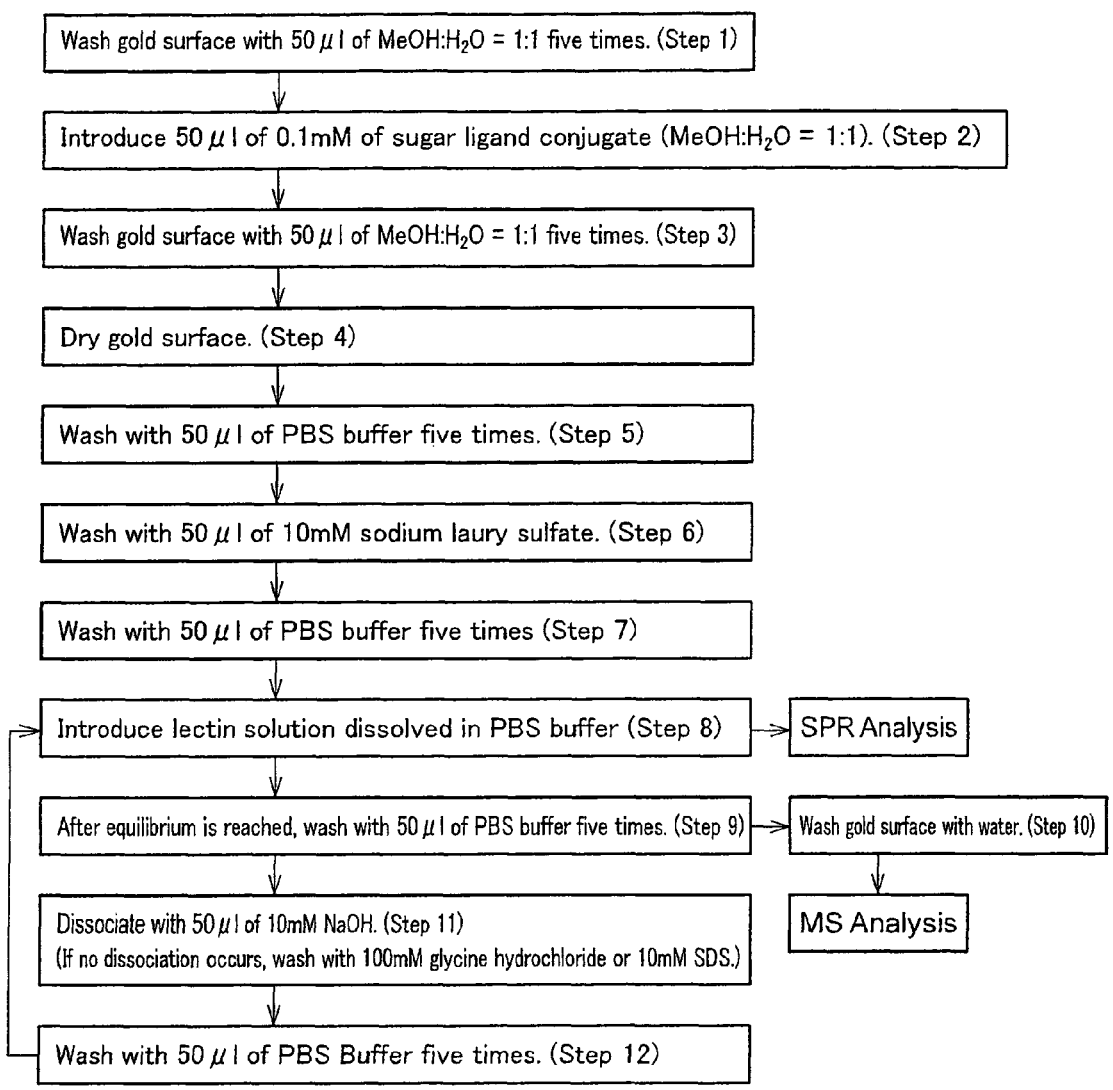
FIG. 1 is a schematic diagram illustrating procedure of protein analysis method using a ligand conjugate according to the present invention.

The present invention is described below in details.

A ligand conjugate according to the present invention is used by being immobilized on a supporter for use in protein analysis, such as sensor chips for Surface Plasmon Resonance (SPR), carriers of affinity chromatography, etc. The ligand conjugate according to the present invention comprises a linker compound linkable to a surface of the supporter, and a sugar chain that can interact specifically with an analyte such as protein and the like. The SPR and affinity chromatography are for identification or isolation of a substance (such as protein) that interacts with a sugar molecule specifically. Thus, the ligand conjugate should not be interactive with the substance such as protein in a non-specific manner.

Therefore, the ligand conjugate according to the present invention comprises a linker portion (linker compound) having a structure represented by General Formula (1). The structure denoted as "Y" in the structure represented by General Formula (1) contains a sulfur atom (S). The sulfur atom (S), for example, forms a metal-sulfur bond (e.g., Au—S bond) with a metal (e.g., Au) with which the surface of the supporter for use in the protein analysis is coated, thereby allowing the ligand conjugate to be firmly bonded to the supporter.

Moreover, the linker compound comprises, as "X" in General Formula (1), a structure having one, two, or three hydrocarbon derivative chains which have an aromatic amino group at the end and may have a carbon-nitrogen bond in its main chain. With this, the linker compounds can be aligned on the surface of the supporter so as to increase the number of the sugar molecules on the surface. Meanwhile, the aromatic amino group at the end allows easy introduction of the sugar molecules.

Moreover, the linker compound comprises, as "Z" in General Formula (1), a straight-chain structure having a carbon-carbon bond or a carbon-oxygen bond. More specifically, it is preferable that Z have a structure represented by Formula (5) or (6). In General Formula (1), p and q are not particularly limited provided that they are independently integers of not less than 0 but not more than 6. Moreover, $n^1$ in Formula (5) and $n^2$ in Formula (6) are not particularly limited provided that they are independently integers of not less than 1 but not more than 6.

An example of the linker compound is a compound represented by General Formula (1) wherein p=4, q=1, Y is a cyclic hydrocarbon structure having a S—S bond, and Z has the structure represented by Formula (5). This linker compound is exemplified by a compound having a structure represented by General Formula (12):

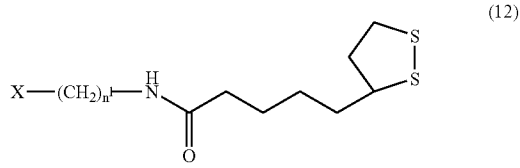

(12)

The linker compound can be synthesized from thioctic acid.

Moreover, an example of the linker compound is a compound represented by General Formula (1) wherein p=4, q=1, Y is a cyclic hydrocarbon structure having a S—S bond, and Z has the structure represented by Formula (6). This linker compound is exemplified by a compound having a structure represented by General Formula (13):

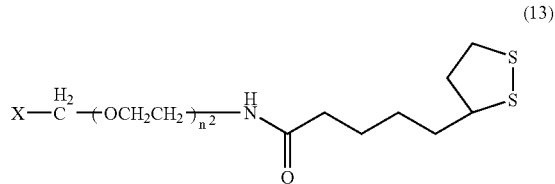

(13)

The linker compound can be synthesized from thioctic acid.

Further, an example of the linker compound is a compound represented by General Formula (1), wherein p=1, q=0, Y is a sulfur atom (S), and Z is a dimer of the structure represented by Formula (5) or (6). An example of such a linker compound is a compound represented by General Formula (14):

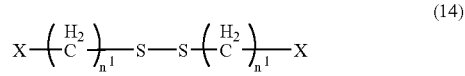

(14)

The linker compounds represented by General Formulae (12), (13), and (14) contain disulfide bond (S—S bond). The sulfur (S) in the S—S bond can form a metal-sulfur bond (e.g., Au—S bond) with a metal (e.g., Au) coating the surface of the supporter for use in protein analysis, thereby to form a strong bond with the supporter. Note that Y is not limited to these represented by General Formulae (12), (13), and (14). For easy formation of the metal-sulfur bond (e.g., Au—S bond), it is preferable that Y be a hydrocarbon structure having a S—S bond or a SH group.

The ligand conjugate according to the present invention is prepared by introducing a sugar chain having a reducing end into the aromatic amino group of the linker compound. In other words, the ligand conjugate according to the present invention has a structure in which the sugar chain having the reducing end is bonded with the linker compound via the aromatic amino group. The introduction of the sugar may be carried out with a reductive amination of the amino group (—NH$_2$) of the aromatic amino group of the linker compound with the sugar. That is, aldehyde group (—CHO group) or ketone group (—CRO group, where R is a hydrocarbon group) occurred in the sugar due to equilibrium is reacted with an amino group of the linker compound. Then, Schiff base formed by the reaction is subsequently reduced, thereby to introduce the sugar into the aromatic amino group with ease.

In the present invention, the sugar having the reducing end is not the sulfated sugar synthesized by the inventor of the present invention and others as described in the earlier application, but a sugar commercially available or prepared by breaking down a polysaccharide commercially available. The "sugar having a reducing end" is a monosaccharide or oligosaccharide whose anomer carbon atom is not substituted. That is, "sugar having a reducing end" is a reducing sugar.

Concrete examples of the sugar having a reducing end include maltose, lactose, panose, cellobiose, melibiose, mannooligosaccharide, chitooligosaccharide, laminarioligosaccharide, and the like. Note that the present invention is not limited to these. A ligand conjugate having an oligosaccharide such as maltose, lactose, or the like is advantageous in its wide applicability for protein analysis compared with the conventional ligand conjugate having the sulfated sugar.

Concrete examples of the ligand conjugate according to the present invention include a ligand conjugate having a structure in which a sugar having a reducing end is introduced into an aromatic amino group of any one of the following linker compounds:

a linker compound having a structure represented by General Formula (7):

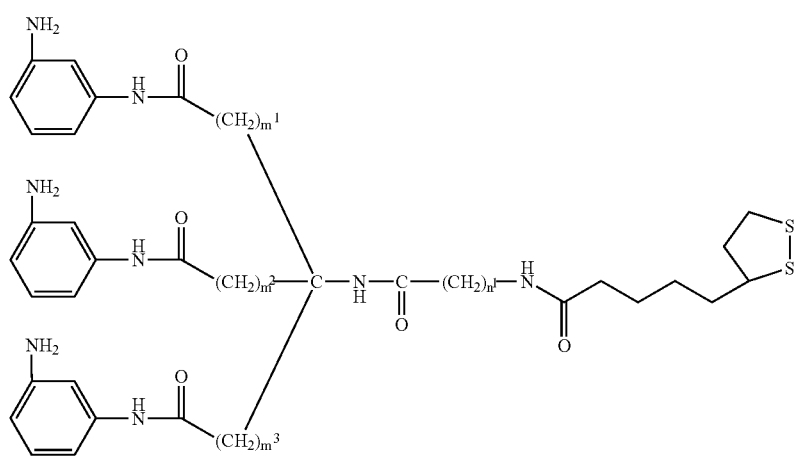

(7)

where $m^1$, $m^2$, and $m^3$ are independently integers of not less than 0 but not more than 6, and $n^1$ is an integer of not less than 1 but not more than 6;

a linker compound having a structure represented by General Formula (8):

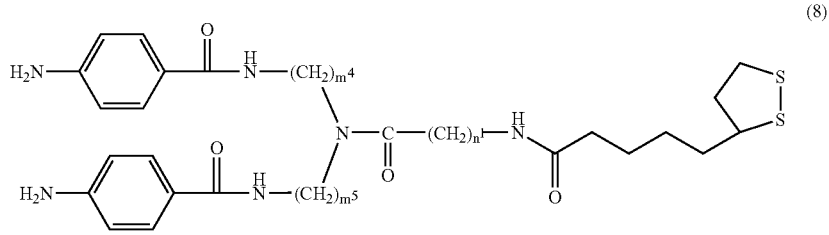

(8)

where $m^4$, and $m^5$ are independently integers of not less than 0 but not more than 6, and $n^1$ is an integer of not less than 1 but not more than 6;

a linker compound having a structure represented by General Formula (9):

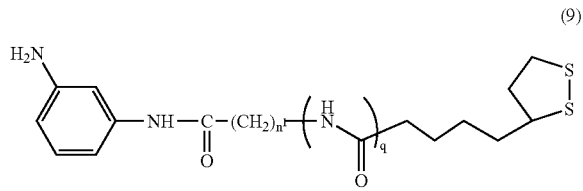

where $n^1$ and q are independently integers of not less than 1 but not more than 6;

a linker compound having a structure represented by General Formula (10):

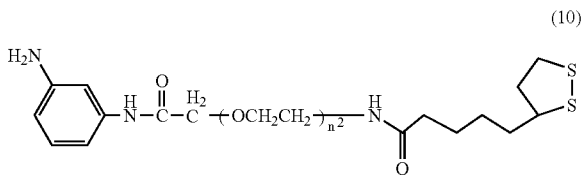

where $n^2$ is an integer of not less than 1 but not more than 6; and a linker compound having a structure represented by General Formula (11):

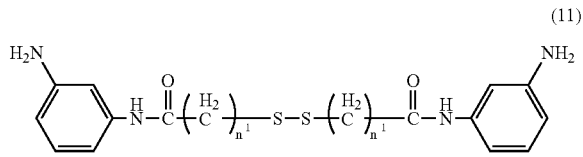

where $n^1$ is an integer of not less than 1 but not more than 6.

The ligand conjugate can be produced by carrying out reductive amination using a sugar having a reducing end and the linker compound represented by any one of General Formulae (7) to (11).

The linker compound having the structure represented by General Formula (7) is a linker compound having three hydrocarbon derivative chains. The three hydrocarbon derivative chains, each of which has an aromatic amino group at the end, are bonded to one carbon (C), thereby forming a branched structure. Note that in General Formula (7), $m^1$, $m^2$, $m^3$ and $n^1$ are not particularly limited provided that $m^1$, $m^2$, and $m^3$ are integers of not less than 0 but not more than 6, and $n^1$ is an integer of not less than 1 but not more than 6. They may be different from one another, or some or all of them may be the same integer. For easy production, it is preferable that $m^1$, $m^2$, and $m^3$ be the same integer, and it is especially preferable that $m^1$, $m^2$, and $m^3$ are 2.

The linker compound having the structure represented by General Formula (8) is a linker compound having two hydrocarbon derivative chains. The two hydrocarbon derivative chains, each of which has an aromatic amino group at its end, are bonded to one nitrogen (N), thereby forming a branched structure. Note that in General Formula (8), $m^4$, $m^5$ and $n^1$ are not particularly limited provided that $m^4$ and $m^5$ are integers of not less than 0 but not more than 6, and $n^1$ is an integer of not less than 1 but not more than 6. They may be different from one another, or some or all of them may be the same integer. For easy production, it is preferable that $m^4$ and $m^5$ be the same integer, and it is especially preferable that $m^4$ and $m^5$ be 2.

The linker compound having the structure represented by General Formula (9) is a linker compound having one hydrocarbon derivative chain. Note that in General Formula (9), $n^1$ and q are not particularly limited, provided that they are integers of not less than 0 but not more than 6. They may be different from one another, or may be the same integer.

The linker compound having the structure represented by General Formula (10) is a linker compound having one hydrocarbon derivative chain. Note that in General Formula (9), $n^2$ is not particularly limited, provided that it is an integer of not less than 1 but not more than 6.

The linker compound having the structure represented by General Formula (11) is a dimer of one hydrocarbon derivative chain. Note that in General Formula (11), $n^1$ is not particularly limited, provided that it is an integer of not less than 1 but not more than 6.

The "X" may have a structure of a multibranching moiety in which plural hydrocarbon derivative chains are bonded at an atom such as a carbon, nitrogen, or the like to form a branching structure, like in General Formula (7) or (8). In case where the "X" contains a plurality of hydrocarbon derivative chains, it is preferable that these hydrocarbon derivative chains have the same structure. However, these hydrocarbon derivative chains may have different structures, provided that they have an aromatic amino group at their ends.

As described above, the linker compound contained in the ligand conjugate according to the present invention contains a sulfur atom which can be bonded to the supporter for use in the protein analysis, and an amino group that can be bonded to a sugar molecule such as oligosaccharide chain, etc. Therefore, the linker compound is immobilized to the supporter for use in the protein analysis via a metal-sulfur bond such as Au—S bond. Thus, it is possible to firmly and easily bond the sugar molecule to the supporter via the linker compound.

Moreover, the linker compound may have a multibranched moiety. In the case where the linker compound has a multibranched moiety, the ends of the branches have an aromatic amino group(s). Therefore, the use of the ligand conjugate according to the present invention in which a sugar having a reducing end is introduced to the linker compound makes it possible to efficiently introduce a large number of sugar molecules on the surface of the supporter.

Further, an influence from the non-specific interaction between the linker compound and the protein is substantially ignorable. Thus, the use of the linker compound to the ligand conjugate according to the present invention makes it possible to evaluate the interaction between the sugar and the protein with good reproducibility.

The linker compound is, for instance, produced by the following production method. That is, the linker compound represented by General Formula (7), (8), (9), or (10) is produced by a condensation reaction of thioctic acid with an amine compound whose aromatic amino group end is protected with a protection group, and then removing the protection group from the aromatic amino group. Moreover, the linker compound represented by General Formula (11) is produced by a condensation reaction of a dimer of γ-mercapto lactate with two molecules of an amine compound whose aromatic amino group end is protected with a protection group, and then removing the protection group from the aromatic amino group end.

The thioctic acid has a structure represented by General Formula (15):

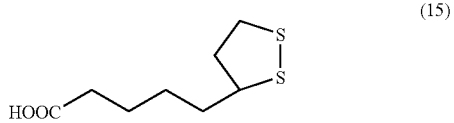
(15)

Moreover, the amine compound is not particularly limited, provided that the amine compound has an aromatic amino group end protected with a protection group.

The protection group is a substitute that is introduced to prevent the amino group of the aromatic amino group from being reacted in the condensation reaction. The protection group is not limited to particular one, and may be t-butoxycarbonyl group (—CHOC(CH$_3$)$_3$ group; hereinafter referred to as Boc group), benzyl group, arylcarbonate group (—COOCH$_2$CH═CH$_2$, Alloc group), or the like.

An example of the amine compound is a primary amine compound having a structure represented by General Formula (16):

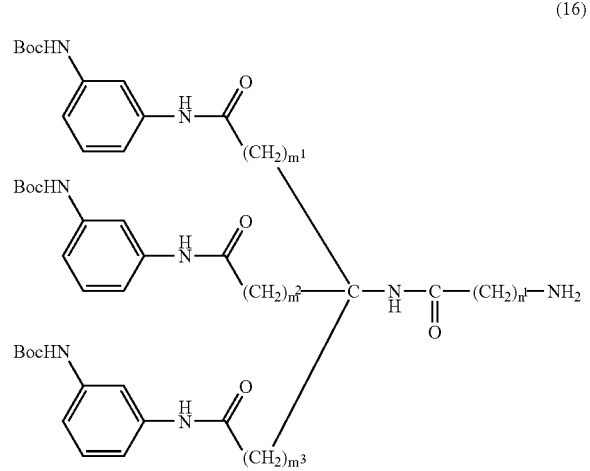
(16)

where $m^1$ to $m^3$ are independently integers of not less than 0 but not more than 6, and $n^1$ is an integer of not less than 1 or not more than 6. The linker compound represented by General Formula (7) is obtained by performing a condensation reaction of thioctic acid with the amine compound represented by General Formula (16), and then removing the protection group from the aromatic amino group end.

Another example of the amino compound is a secondary amine compound represented by General Formula (17):

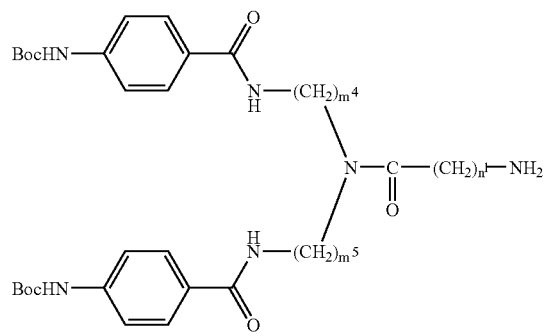
(17)

where $m^4$ and $m^5$ are independently integers of not less than 0 but not more than 6, and $n^1$ is an integer not less than 1 but not more than 6. The linker compound represented by General Formula (8) is obtained by performing a condensation reaction of thioctic acid with the amine compound represented by General Formula (17), and then removing the protection group from the aromatic amino group end. The synthesis scheme of the amino compound will be described later in Examples.

The condensation reaction of the amine compound with thioctic acid or γ-mercapto lactate condenses the carboxylic group (—COOH group) of thioctic acid or γ-mercapto lactate with the amino group (—NH$_2$ group) of the amine compound, thereby forming an amide bond. After the condensation reaction, the protection group is removed from the aromatic amino group end, so as to obtain the linker compound.

By introducing an oligosaccharide having a reducing end such as maltose, lactose, or the like to the linker compound prepared as above, the ligand conjugate according to the present invention is obtained. Concrete examples of the ligand conjugate according to the present invention encompass the following ligand conjugates.

A first ligand conjugate having a structure represented by General Formula (12), where X has a structure represented by General Formula (2), R' is a hydrogen (H), and R is maltose having the structure shown in Formula (18):

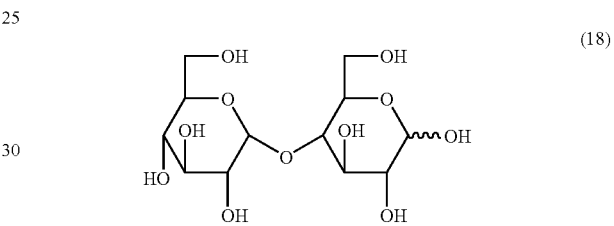
(18)

A second ligand conjugate having a structure represented by General Formula (12), where X has a structure represented by General Formula (2), R' is a hydrogen (H), and R is lactose having the structure shown in Formula (19):

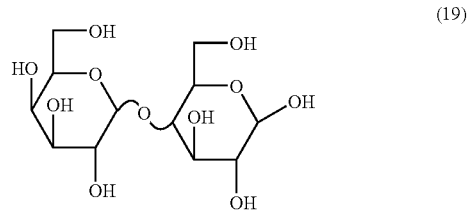
(19)

The first and second ligand conjugates have the linker compound having three hydrocarbon derivative chains, to each of which one oligosaccharide is introduced. In other words, the first ligand conjugate has three units of α-glucopyranose at its ends, whereas the second ligand compound has three units of β-galactopyranose at its ends. In General Formula (2), $m^1$ to $m^3$ are not particularly limited, provided that they are integers of not less than 0 but not more than 6. They may be different from one another, or some or all of them may be the same integer. Moreover, in General Formula (12), $n^1$ is not particularly limited, provided that it is an integer of not less than 1 but not more than 6.

A third ligand conjugate having a structure represented by General Formula (12), where X has a structure represented by General Formula (3), R' is a hydrogen (H), and R is maltose having the structure shown in Formula (18).

A fourth ligand conjugate having a structure represented by General Formula (12), where X has a structure represented by General Formula (3), R' is a hydrogen (H), and R is lactose having the structure shown in Formula (19).

The third and fourth ligand conjugates have the linker compound having two hydrocarbon derivative chains, to each of which one oligosaccharide is introduced. In other words, the third ligand conjugate has two units of α-glucopyranose at its ends, whereas the fourth ligand compound has two units of β-galactopyranose at its ends. In General Formula (3), $m^4$ and $m^5$ are not particularly limited, provided that they are integers of not less than 0 but not more than 6. They may be different from one another, or some or all of them may be the same integer. Moreover, in General Formula (12), $n^1$ is not particularly limited, provided that it is an integer of not less than 1 but not more than 6.

A fifth ligand conjugate having a structure represented by General Formula (13), where X has a structure represented by General Formula (4), R' is a hydrogen (H), and R is glucose. In General Formula (13), $n^2$ is not particularly limited, provided that it is an integer of not less than 1 but not more than 6.

A sixth ligand conjugate having a structure represented by General Formula (13), where X has a structure represented by General Formula (4), R' is a hydrogen (H), and R is maltose. In General Formula (13), $n^2$ is not particularly limited, provided that it is an integer of not less than 1 but not more than 6.

A seventh ligand conjugate having a structure represented by General Formula (14), where X has a structure represented by General Formula (4), R' is a hydrogen (H), and R is glucose. In General Formula (14), $n^1$ is not particularly limited, provided that it is an integer of not less than 1 but not more than 6.

An eighth ligand conjugate having a structure represented by General Formula (14), where X has a structure represented by General Formula (4), R' is a hydrogen (H), and R is maltose. In General Formula (14), $n^1$ is not particularly limited, provided that it is an integer of not less than 1 but not more than 6.

Further concrete examples of the ligand conjugate according to the present invention encompass seventeen ligand conjugates to which seventeen kinds of sugar chains are respectively introduced to the linker compound having the structure represented by General Formula (9), the seventeen kinds of sugar chains being shown below in Group (20):

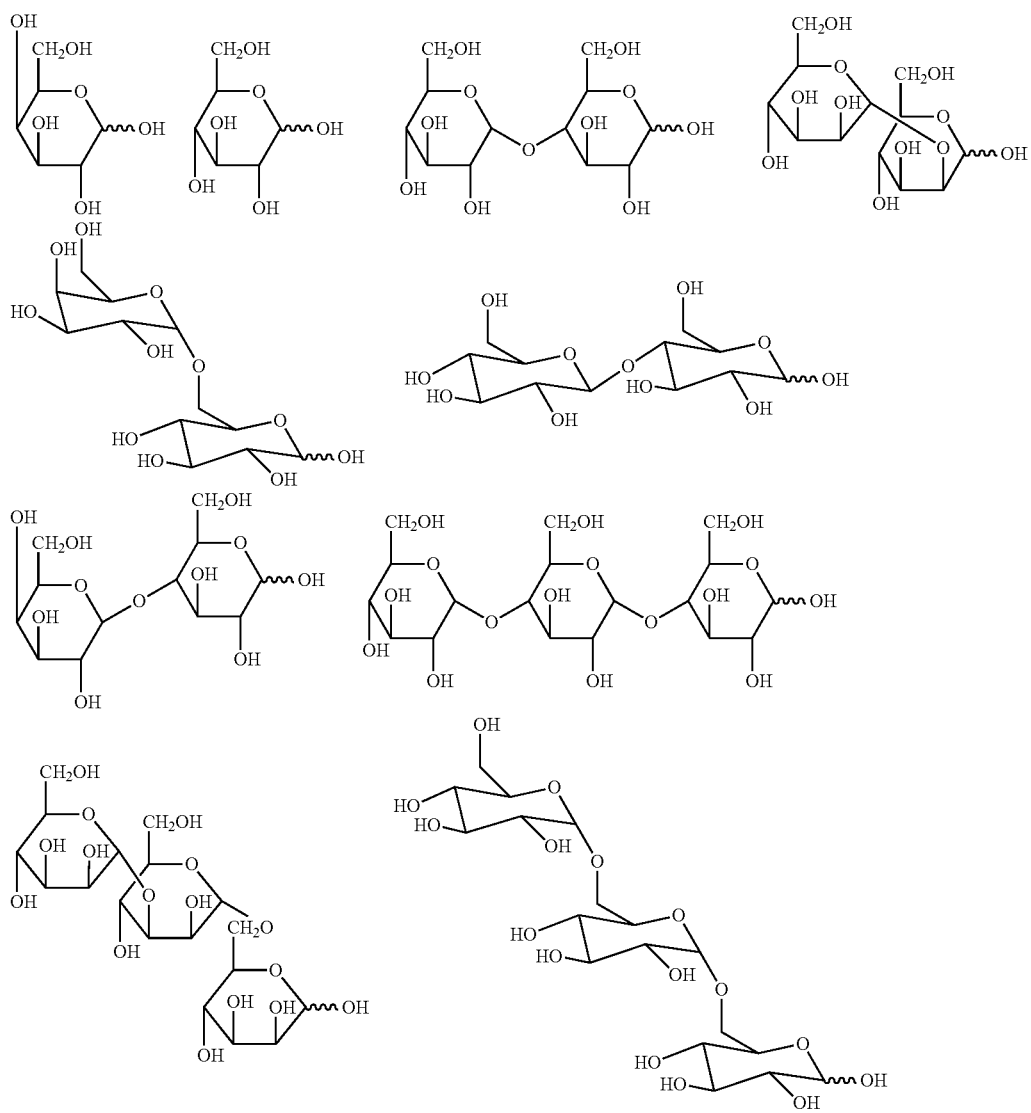

-continued

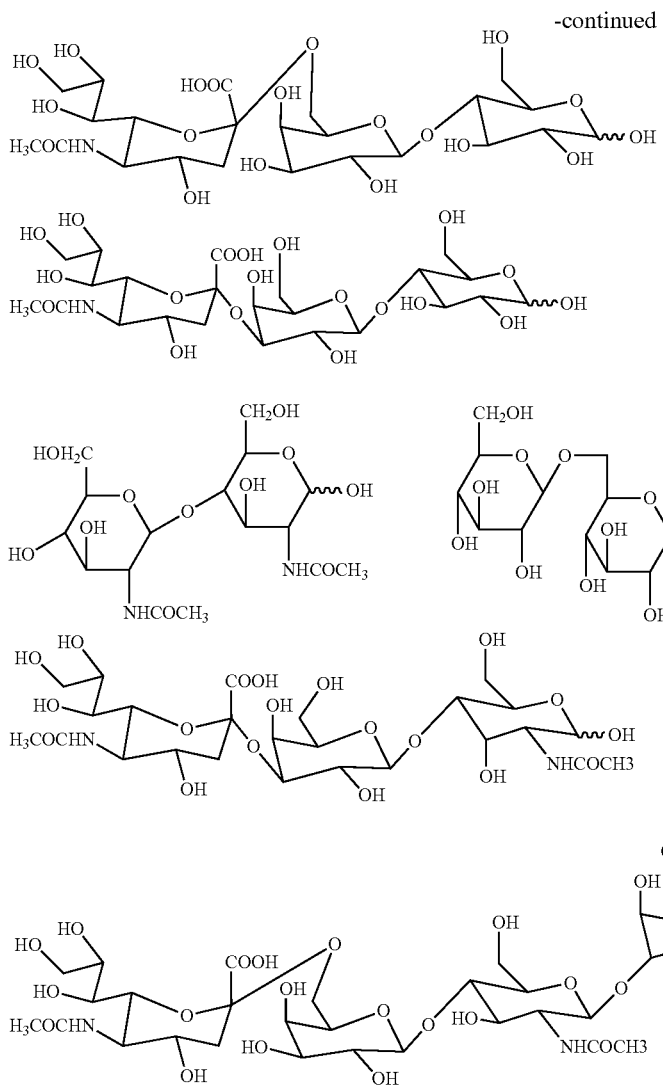

The ligand conjugates respectively contain the linker compound and any one of the sugar molecules. Therefore, the ligand conjugate can be bonded with the metal on the surface of the supporter for use in protein analysis via the metal-sulfur (S) bond, e.g., gold-sulfur (Au—S) bond. By this, it is possible to provide a ligand carrier in which a large number of sugar molecules are immobilized via the Au—S bond. Besides Au, the metal on the surface of the supporter may be Cu, Ag, Pt, or the like. However, Au is especially preferable.

Moreover, as described in Examples, it was confirmed that the ligand conjugates mentioned above show different interaction with proteins. That is, it is considered that these ligand conjugates can be effectively used for identification of unknown protein.

The oligosaccharide introduced in the ligand conjugate according to the present invention may be homooligosaccharide containing only one type of monosaccharide molecules, or heterosaccharide containing various type of monosaccharide molecules and/or a derivative(s) thereof. Moreover, various natural sugars obtained from the nature via isolation and purification, and synthesized sugars may be the oligosaccharide mentioned above. Moreover, the oligosaccharide may be an oligosaccharide obtained by breaking down a polysaccharide.

Moreover, the present invention encompasses ligand carriers in which a ligand conjugate of the present invention as described above is immobilized, via a metal-sulfur bond, onto the supporter having a metal on its surface. Application of the ligand carriers is not limited to protein analysis. It is possible to use the ligand carrier to analysis of interaction between a sugar molecule and a substance other than protein.

The introduction of the ligand conjugate to the supporter surface in the ligand carrier is carried out by allowing the supporter having a metal film on its surface to stand in contact with a ligand conjugate solution having the ligand conjugate so as to bond each S atom of the S—S bond in the ligand conjugate to the metal on the supporter via the metal-sulfur bond. Specifically, the supporter for use in protein analysis is immersed in the ligand conjugate solution for a predetermined time, or the ligand conjugate solution is introduced to the supporter (the supporter surface is washed with the ligand conjugate solution), thereby converting the S—S bond of the ligand conjugate (the linker compound contained in the ligand conjugate) to, e.g., the Au—S bond with gold on the supporter on the surface. By doing this, the ligand conjugate is immobilized on the supporter surface.

There is no particular limitation as to the solvent of the ligand conjugate solution. For example, methanol, water, dimethylacetoamide (DMAc), or a mixture solution thereof, etc. can be used as the solvent. Moreover, it is sufficient that immersing time period is in a range of 0.5 to 12 hours, and the ligand conjugate solution to be introduced is in an order of 1 µM to 1 mM.

As described above, the ligand conjugate of the present invention has a S—S bond. This makes it easier to immobilize the ligand conjugate to the surface of the supporter for use in protein analysis, and thus to introduce the sugar surface to the supporter.

The ligand carrier according to the present invention is applicable to analysis of interaction of a sugar molecule and, e.g., a substance other than protein. Specifically, the ligand carrier is applicable to SPR measurement, affinity chromatography, etc.

For example, the SPR measurement as a protein analysis may be carried out as follows. That is, the ligand carrier in which the ligand conjugate of the present invention is used as a supporter to which a metal film such as a gold film is deposited. The ligand carrier is caused to be in contact with protein. By standard methods known in the art, a resonance angle is measured using a surface plasmon resonance device. Thereby, a bonding behavior of the ligand carrier and the protein can be observed. The supporter (sensor chip) for use in the SPR measurement may be glass, plastic, or the like, for example. Especially, glass is preferable. The ligand carrier may be caused to be in contact with the protein by washing the surface of the ligand carrier with a solution in which a protein is dissolved in a running buffer. The running buffer may be a phosphate buffer solution or the like, for example.

As shown in Example later, it was confirmed that the ligand carrier of the present invention exhibited different interactions with respective proteins. Thus, the ligand carrier can be used for protein identification. That is, analysis of unknown protein can be carried out using the ligand carrier of the present invention in order to easily determine whether the protein is sugar-binding protein or not, and which type of protein it is. A chip set including at least two types of the ligand carriers to which the ligand conjugates are immobilized respectively is effective to more easily perform protein identification (especially identification of sugar-binding protein).

Here, the application of the ligand carrier of the present invention is explained. The ligand carrier of the present invention can be used as a sensor chip for use in measurement of intermolecular interaction (e.g., SPR measurement described below). That is, by using a first sensor chip in which a first ligand conjugate is immobilized on a supporter surface and a second sensor chip in which a second ligand conjugate is immobilized on a supporter surface, a difference between detection results of SPR measurement using the first sensor chip and the detection results of SPR measurement using the second sensor chip is detected. Thereby, the interaction of the sugar molecule can be observed.

These sensor chip may include ligand conjugates in which different sugar molecules are immobilized, or ligand conjugates in which the same sugar molecule is immobilized to different linker compounds. The different types of ligand conjugates may be the respective ligand conjugates mentioned above, for example. Moreover, it is preferable to select, from among the ligand conjugates mentioned above, ligand conjugates having the same linker compound structure but different oligosaccharide structure (e.g., the set of the first ligand conjugate and the second ligand conjugate, or the set of the third ligand conjugate and the fourth ligand conjugate).

In the SPR measurement, a protein or the like that specifically interacts with the sugar molecule of the first sensor chip is caused to react with the two sensor chips under the same measuring condition, thereby to observe the resonance angle of the two sensor chips. By detecting a difference between the resonance angle of the two sensor chips, it is possible to measure a specific interaction between the sugar molecule and the protein or the like.

Moreover, as to the substance to be observed for the interaction with the sugar molecule, the present invention is not limited to proteins.

The present invention is not limited to the case where two types of sensor chips are measured at the same time. It is possible to measure with more than two types of sensor chips, and the sensor chips may not be measured at the same time. Moreover, at least one of the sensor chips may be such that a sugar molecule is not introduced. For example, the at least one of the sensor chips may be such that only the linker compound is immobilized.

Such SPR measurement is carried out using at least two sensor chips having identical ligand conjugates with each other but different sugar molecules. Therefore, if the interactions caused by the at least two sensor chips are different, it will be observed that the sugar molecules causes the difference. Thus, using method including above measurement procedure, it is possible to reduce non-specific interaction between the sites other than sugar molecules and another substances and to observe the specific interaction between sugar molecules and another substances.

Furthermore, the SPR measurement may be carried out with two types of sensor chips in which ligand conjugates having the same sugar molecule but different linker compound structure. With such SPR measurement, it is possible to analyze bonding behaviors of a protein with sensor chips in which the number of sugar molecules present are different. An example of such a set of sensor chips is the set of the first ligand conjugate and the third ligand conjugate.

Moreover, mass spectroscopy may be carried out after the SPR measure that confirms a specific interaction between a sugar molecule and the other substance, thereby carrying out mass spectroscopy of the ligand carrier used in the SPR measurement and to which the protein is bonded. In this way, it is possible to identify the protein bonded on the sensor chip. The mass analysis may be carried out using a conventionally known mass spectrometer such as a matrix-assisted laser desorption/time of flight mass spectrometer (MALDI-TOF/MS), or the like in the conventional known manner.

Through the procedure mentioned above, it is possible to perform protein analysis using the ligand conjugate according to the present invention. That is, the protein analysis method according to the present invention comprises: preparing a ligand carrier by causing a ligand conjugate according to the present invention to be in contact with a supporter having a metal on its surface so as to immobilize the ligand conjugate on the supporter; causing the ligand carrier to be in contact with a solution containing a protein to be analyzed, so as to cause interaction, and then performing intermolecular interaction measurement such as SPR; and after the intermolecular interaction measurement, performing mass spectroscopy so as to identify the protein bonded to the ligand carrier.

In the protein analysis method, it is possible to perform protein analysis using two or more types of ligand carrier in which different ligand conjugates are respectively immobilized. By comparing the results from each types of the ligand carrier, it is possible to analyze the characteristics of the proteins.

EXAMPLES

Hereinafter, the synthesis of the ligand conjugate according to the present invention is described in details. Moreover, in the present Examples, SPR measurement and mass spectroscopy were carried out using synthesized ligand conjugates so as to analyze proteins. This will be also explained below.

Example 1

Synthesis of Ligand Conjugates (Compounds 1 to 4)

In the present Example, four ligand conjugates classified respectively as first to fourth ligand conjugates described in the embodiment were synthesized.

(1) Synthesis of First Ligand Conjugate (Compound 1)

A ligand conjugate (Compound 1), which was a first ligand conjugate mentioned above, was synthesized as follows, the ligand conjugate (compound 1) having a structure represented by General Formula (12), where $n^1$ was 1, X was represented by General Formula (2), R' was a hydrogen (H), and R is maltose shown by Formula (18), and $m^1$, $m^2$, and $m^3$ were 2.

As prepreparation of the synthesis of the ligand conjugate (compound 1), a linker compound A was synthesized, which had three branches each of which had an aromatic amino group end protected with a protection group.

Firstly, as shown in Formula (21), three units of t-butylacrylate (compound 6) were Michel-added to nitromethane (compound 5) under benzyltrimethylammonium hydroxide in dimethoxyethane of 65° C. to 70° C., thereby obtaining compound 7 at 91% yield. Next, under hydrogen atmosphere (6 kg/cm$^2$), the nitro group of compound 7 was reduced using Raney Ni in ethanol of 50° C., thereby obtaining compound 8 at a 98% yield.

After that, compound 8 was condensed with z-glycine of 1.1 equivalent in the presence of water-soluble carbodimide hydrochloride (in formula, EDC.HCl) of 1.1 equivalent, and 1-hydroxy-7-azapnezotriazol (in formula, HOAt) of 1.1 equivalent in CH$_2$Cl$_2$, thereby obtaining Z-glycine compound (compound 9).

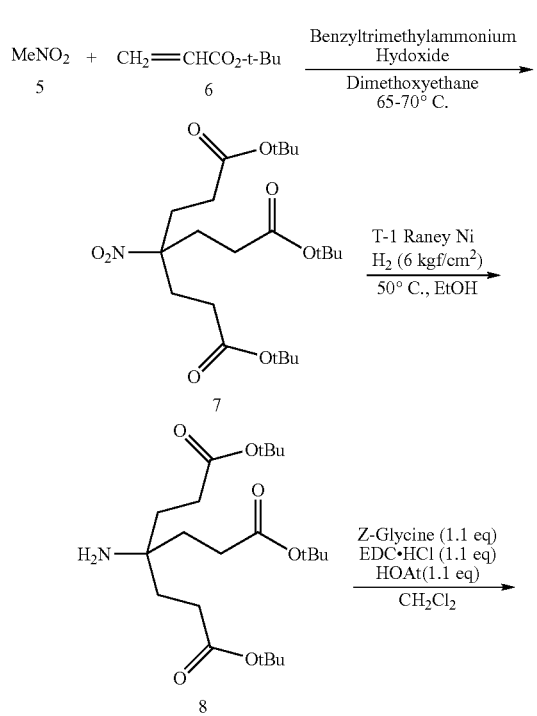

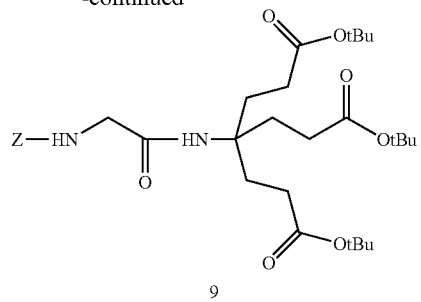

To explain more specifically, compound 8 was prepared as follows: In accordance with a method described in a literature (G. R. Newkome et al. OPPI BRIEFS, vol. 28, p 495, 1996), nitromethane (12.2 g, 200 mmol) was firstly dissolved in 50 mL of 1,2-dimethoxyethane and then heated to 65-70° C. Then, 40% benzyltrimethyl ammonium-methanol solution (2 mL) was added therein, thereby obtaining a nitromethane solution. Next, the nitromethane solution was heated to 75° C. and then t-butyl acrylate (90.8 mL, 620 mmol) was dropped therein slowly. After that, 40% benzyltrimethylammonium-methanol solution was added therein by pouring 1 mL thereof 4 times, and then stirred for 2.5 hours, thereby obtaining a nitromethane/t-butylacrylate reaction solution. The nitromethane/t-butylacrylate reaction solution was decanted to remove impurity therein, and concentrated. The residue thus obtained was dissolved in diethylether and washed with ice-cooled 10% hydrochloric acid, with saturated sodium hydrogen carbonate aqueous solution and then with water, twice each, thereby obtaining a residue solution. After that, the residue solution was dried with anhydrous sodium sulfate acting as a drying agent. After the drying agent was removed using Celite, the residue solution was concentrated under reduced pressure. The concentrated residue was dissolved in ethanol and recrystallized, thereby obtaining compound 7 (81.8 g, 91%), which was white needle crystal.

Then, the crystal of compound 7 (10 g, 22.4 mmol) and T−1 Raney Ni (6.0 g) were added to 50 mL of anhydrous ethanol, and stirred for 23 hours at 50° C. under hydrogen atmosphere of 6 kg/cm$^2$. Then, T−1 Raney Ni was filtered off using Celite, thereby obtaining a compound 7 reaction solution. The compound 7 reaction solution was concentrated under reduced pressure, thereby obtaining concentrated residue. The concentrated residue was purified via silica gel chromatography (solvent:chloroform/methanol=20/1), thereby obtaining compound 8 (yield 9.2 g, 98%).

More specifically, in a Z-glycine solution in which Z-glycine (1.26 g, 6.62 mol) and HOAt (0.90 g, 6.62 mmol), and EDC.HCl (1.27 g, 6.62 mmol) were dissolved in anhydrous dichloromethane (28 mL), a compound 8 solution in which compound 8 (2.50 g, 6.02 mmol) was dissolved in anhydrous dichloromethane (2 mL) was added and stirred for 36 hours at room temperature under argon atmosphere, thereby obtaining a Z-glycine/compound 8 reaction solution. To the Z-glycine/compound 8 reaction solution, dichloromethane and 10% citric acid solution were added. Then, extraction with dichloromethane was performed to obtain an organic layer. The organic layer was then washed with water, with saturated sodium hydrogen carbonate solution, and then with water, once each. The resultant was sequentially dried with anhydrous sodium sulfate acting as a drying agent. After the drying agent was filtered off, the resultant was concentrated under reduced pressure, thereby obtaining a concentrated residue. The concentrated residue was purified via silica gel chromatography (solvent:chloroform), thereby obtaining compound 9 (yield: 3.09 g, 85%), which was white solid.

ESI-MS (positive) analysis (flight-time mass spectrometer measurement) of compound 9 thus obtained showed that m/z (mass/charge) was 629.4 [(M+Na)+]. Moreover, nuclear magnetic resonance ($^1$H-NMR, 400 MHz, CDCl$_3$) analysis of compound 9 showed that δ7.37-7.26 (5H, m, Ph), 6.43 (1H, bs, CON$\underline{H}$C), 5.38 (1H, bs, Gly-N$\underline{H}$), 5.13 (2H, s, CH$_2$Ph), 3.78 (2H, d, J=7.7 Hz, Gly-C$\underline{H}_2$), 2.20 (6H, t, J=7.7 Hz, CC$\underline{H}_2$CH$_2$), 1.96 (6H, t, J=7.7 Hz, CCH$_2$C$\underline{H}_2$), 1.44 (27H, s, C$\underline{H}_3$). With this, the structure of compound 9 was confirmed. In addition, compound 9 has a molecular mass of 606.35.

Next, as shown in Formula (22), deprotection of t-butoxycarbonyl group (—COOC(CH$_3$)$_3$ group; tBu in Formula (22)) of compound 9 was carried out using trifluoro acetic acid (hereinafter, TFA) in a mixture solvent of CH$_2$Cl$_2$/H$_2$O=10/1, thereby obtained compound 10 with 95% yield.

After that, in the presence of pentafluorophenyldiphenylphosphate (FDPP in the formula) of 4.5 equivalent, diisopropylethylamine (DIPEA in the formula) of 11 equivalent, N,N-dimethylformaldehyde (DMF), compound 10 was condensed with m-phenylene diamine derivative (compound 11, 10 equivalent) whose amino group was protected with Boc group, thereby obtaining N-Boc amine derivative (compound 12) with 99% yield. Then, catalytic hydrogen reduction was carried out in methanol (MeOH in the formula) in the presence of Pd/C (palladium supported in activated carbon). After that, deprotection of benzyloxycarbonyl group (Z group in formula) of Z-glycine that had been condensed with compound 12 was carried out. Consequently, compound 13 was obtained with a 79% yield.

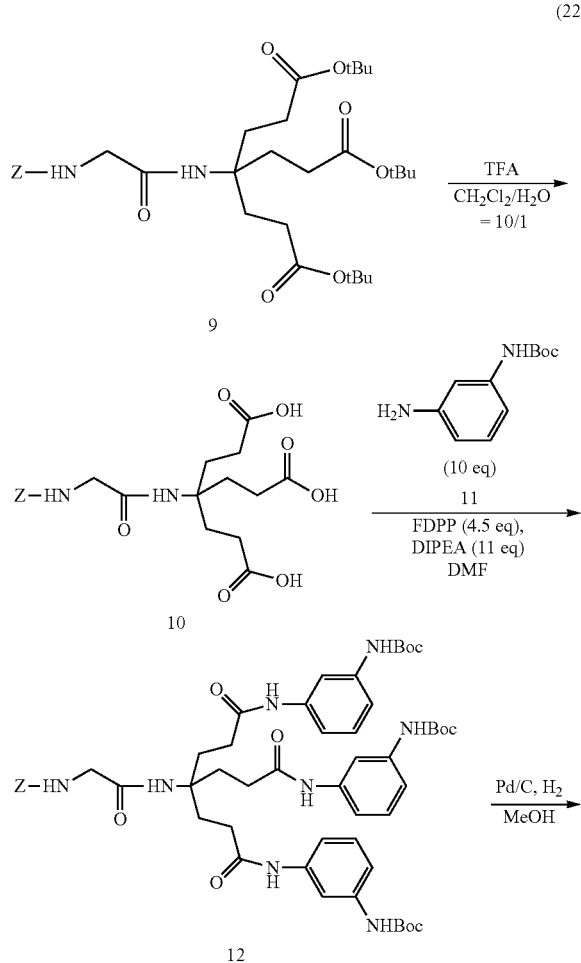

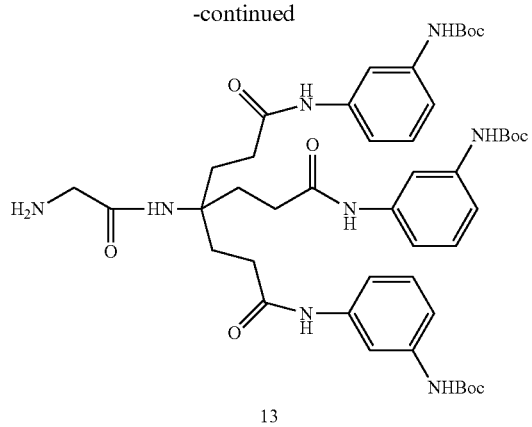

Specifically, compounds 10 to 13 were prepared as follows.

The preparation of compound 10 was carried out as below. Compound 9 (2.98 g, 4.90 mmol) was dissolved in dichloromethane (15 mL). After TFA (15 mL) and water (1.5 mL) was added therein at a temperature of −10° C., the mixture was stirred at room temperature for 1.5 hours, thereby obtaining the compound 9 reaction solution. Then, the compound 9 reaction solution under was concentrated under reduced pressure. Then, in an ice bath, 10% sodium hydroxide was added until pH 5 was obtained, and then concentrated hydrochloride was added until pH 2 was obtained, thereby precipitating white solid. The white solid thus obtained was washed with water, thereby obtaining Compound 10 (yield 2.04 g, 95%) in the form of white solid.

ESI-MS (negative) analysis of compound 10 thus obtained showed that m/z was 437.1 [(M−H)−]. Moreover, nuclear magnetic resonance ($^1$H-NMR, 400 MHz, d$_6$-DMSO) analysis of compound 10 showed that δ7.34-7.30 (6H, m, Ph, CON$\underline{H}$C), 7.15 (1H, s, Gly-N$\underline{H}$), 5.01 (2H, s, C$\underline{H}_2$Ph), 3.55 (2H, d, J=5.9 Hz, Gly-C$\underline{H}_2$), 3.33 (3H, brs, CO$_2\underline{H}$), 2.11 (6H, m, CC$\underline{H}_2$CH$_2$), 1.81 (6H, m, CCH$_2$C$\underline{H}_2$). These results confirmed the structure of compound 10. In addition, molecular mass of compound 10 was found to be 438.16.

The preparation of Compound 11 was carried out as follows. Firstly, m-phenylenediamine (0.50 g, 4.62 mmol) was dissolved in methanol (35 mL). Then, (Boc)$_2$O (1.06 mL, 4.62 mmol) and triethylamine (0.65 mL, 4.65 mmol) were added therein at 0° C., and then stirred at room temperature for 24 hours. After that, the resultant solution was concentrated under reduced pressure, thereby obtaining the concentrated residue. The concentrated residue was purified via silica gel chromatography (solvent:chloroform/acetone=10/1), thereby obtaining Compound 11 (yield 665 mg, 68%), which was white solid.

ESI-MS (positive) of Compound 11 showed that m/z was 231.2 [M+Na]+. $^1$H-NMR (400 MHz, CDCl$_3$) analysis of Compound 11 showed that δ7.02 (1H, t, J=8.0 Hz, aromatic), 6.95 (1H, bs, aromatic), 6.54 (1H, dd, J=2.0 Hz, J=8.0 Hz, aromatic), 6.41 (1H, bs, CON$\underline{H}$), 6.35 (1H, dd, J=2.2 Hz, J=7.9 Hz, aromatic), 3.66 (2H, bs, N$\underline{H}_2$), 1.50 (9H, s, t-butyl). These results confirmed the structure of Compound 11. In addition, Compound 11 was found to have a molecular mass of 208.12.

The preparation of Compound 12 was carried out as follows. Compound 10 (100 mg, 228 μmol), Compound 11 (475 mg, 2.28 mmol), FDPP (394 mg, 1.03 mmol), and diisopropylethylamine (447 μL, 2.57 mmol) were dissolved in anhydrous dimethylformamide (2 mL), and then stirred at room temperature for 29 hours under argon atmosphere. Then, ethyl acetate and water were added therein and extraction with ethyl acetate was conducted, so as to obtain an organic layer. The organic layer was washed with 0.5N hydrochloride, with water, with saturated sodium hydrogen carbonate aqueous solution, and then with saturated saline, once each, and then dried with anhydrous sodium sulfate acting as a drying agent, thereby obtaining dried reaction solution. After filtering off the drying agent therefrom, the drying reaction solution thus obtained was concentrated under reduced pressure, thereby obtaining concentrated residue. The concentrated residue was purified via silica gel chromatography (solvent:chloroform/acetone=3/1), thereby obtaining Compound 12 (yield 228 mg, 99%) in the form of white solid.

ESI-MS (positive) analysis of Compound 12 showed that m/z=1009.5 [(M+H)$^+$]. Moreover, $^1$H-NMR (400 MHz, CDCl$_3$) analysis of Compound 12 showed that δ8.75 (3H, s, NHCO$_2$tBu), 7.67 (3H, s, CONHPh), 7.30-6.95 (15H, m, aromatic, CH$_2$CONH), 6.52 (1H, bs, Gly-NH), 5.04 (2H, s, CH$_2$Ph), 3.71 (2H, d, J=5.0 Hz, Gly-CH$_2$), 2.23 (6H, m, CH$_2$CH$_2$CO), 1.97 (6H, m, CH$_2$CH$_2$CO), 1.47 (27H, s, t-butyl). These results confirmed the structure of Compound 12. In addition, Compound 12 was found to have a molecular mass of 1008.50.

Moreover, the preparation of Compound 13 was carried out as follows. Firstly, Compound 12 (200 mg, 198 μmol) was dissolved in methanol (3 mL). Then 10% Pd/C (62.3 mg) was added therein and stirred at room temperature for 15 hours. After Pd/C was filtered off therefrom, the resultant solution was concentrated under reduced pressure, thereby obtaining concentrated residue. The concentrated residue was then purified via silica gel chromatography, thereby obtaining Compound 13 (yield 136 mg, 78%) in the form of white solid.

ESI-MS (positive) analysis of Compound 13 showed that m/z was 875.5 [(M+H)$^+$]. Moreover, $^1$H-NMR (400 MHz, CDCl$_3$) of Compound 13 showed that δ 9.00 (3H, s, NHCO$_2$tBu), 7.57 (2H, s, NH$_2$), 7.35 (1H, bs, Gly-NH), 7.14-7.00 (15H, m, aromatic, CH$_2$CONH), 3.21 (2H, s, Gly-CH$_2$), 2.26 (6H, m, CH$_2$CH$_2$CO), 2.04 (6H, m, CH$_2$CH$_2$CO), 1.45 (27H, s, t-butyl). These results confirmed that structure of Compound 13. In addition, Compound 13 was found to have a molecular mass of 874.46.

Furthermore, as shown in Formula (23), in the presence of EDC.HCl of 1.0 equivalent, 1-hydroxybenzotriazole (HOBt in Formula (23)) of 1.0 equivalent, and CH$_2$Cl$_2$, Compound 13 was condensed with thioctic acid (Compound 14) of 1.0 equivalent, thereby obtaining a thioctic acid derivative (compound 15) with 75% yield.

The Boc group of Compound 15 thus obtained was removed under an acidic condition in the presence of trimethylsilylchloride (TMSCl in formula) and phenol (PhOH) in CH$_2$Cl$_2$, thereby obtaining Compound A, which was a linker compound having three hydrocarbon derivative chains, each of which had an aromatic amino group (Yield 32%).

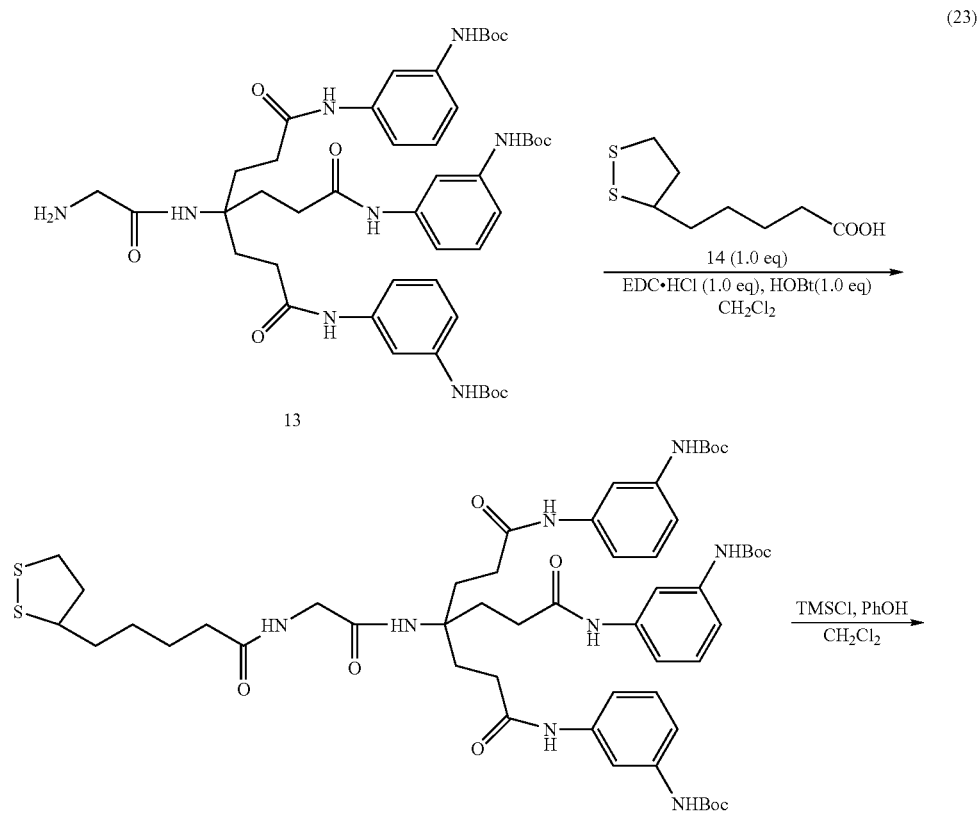

(23)

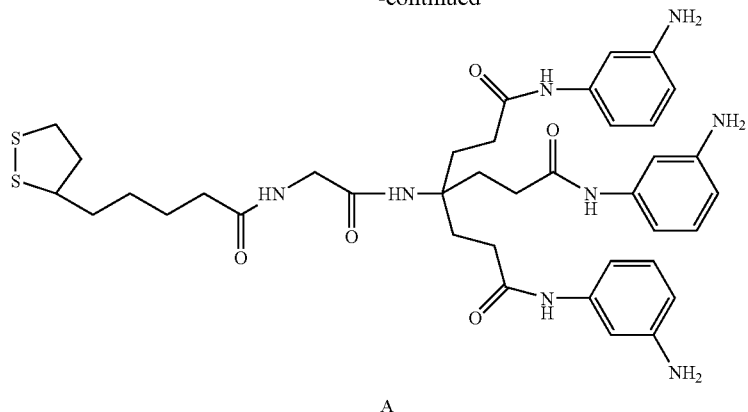

A

More specifically, the preparation of Compound 15 and Compound A was carried out as follows.

To obtain Compound 15, Compound 14 (23.6 mg, 114 mol) and HOBt (15.4 mg, 114 mmol) were dissolved in anhydrous dichloromethane (2.3 mL). Then, Compound 13 (250 mg, 6.02 mmol) was added therein at 0° C., and then stirred in argon atmosphere at room temperature for 36 hours in the dark. After that, 10% citric acid solution was added therein and extraction with chloroform was conducted. The organic layer thus obtained was washed with saturated sodium hydrogen carbonate solution and then dried with anhydrous sodium sulfate acting as a drying agent. After the drying agent was filtered off, the resultant was concentrated under reduced pressure, thereby obtaining concentrated residue. The concentrated residue was then purified via silica gel chromatography (solvent: hloroform/methanol=40/1), thereby obtaining Compound 15 (Yield: 91.0 mg, 75%).

ESI-MS (positive) analysis of Compound 15 showed that m/z was 1085.5 [(M+H)$^+$]. Moreover, $^1$H-NMR (400 MHz, CD$_3$Cl) analysis of Compound 15 showed that δ9.01 (3H, bs, NHCO$_2$tBu), 7.67 (3H, s, CONHPh), 7.31 (1H, bs, CON HCH$_2$), 7.27-7.00 (12H, m, aromatic), 3.71 (2H, bs, Gly-C H$_2$), 3.64-3.39 (1H, m, SSCH), 3.12-2.99 (2H, m, CH$_2$SS), 2.33 (1H, m, CH$_2$CH$_2$SS), 2.32 (6H, m, CCH$_2$CH$_2$CO), 2.20 (2H, m, CH$_2$CONHCH$_2$), 2.04 (6H, m, CCH$_2$CH$_2$CO), 1.82-1.73 (1H, m, CH$_2$CH$_2$SS), 1.62-1.47 (4H, m, C H$_2$(CH$_2$)$_2$CONH, (CH$_2$)$_2$CH$_2$CH$_2$CONH), 1.47 (27H, s, t-butyl), 1.39-1.25 (2H, m, CH$_2$CH$_2$(CH$_2$)$_2$CONH). These results confirmed the structure of Compound 15. In addition, Compound 15 was found to have a molecular mass of 1062.49.

Moreover, the preparation of Compound A was carried out as follows. Firstly, trimethylsilylchloride (0.25 mL, 2.64 mmol) was dissolved in dichloromethane (0.49 mL). Then, a phenol solution prepared by dissolving phenol (549 mg, 5.83 mmol) in dichrolomethane (1.46 mL) was added therein and stirred. Furthermore, Compound 15 (34.7 mg, 32.61 mmol) was added therein and stirred for 1.5 hours at room temperature in the dark, thereby obtaining a compound 15 reaction solution. Subsequently, chloroform was added to the compound 15 reaction solution. The organic layer thus obtained was washed with a saturated sodium hydrogen carbonate aqueous solution, thereby precipitating yellow solid. The precipitated yellow solid was dissolved in acetic acid and cooled down to 4° C. Then, aggregated solid was filtered off, thereby obtaining Compound A (Yield 7.mg, 32%) in the form of white solid.

ESI-MS (positive) analysis of Compound A showed that m/z was 763.6 [(M+H)$^+$]. Moreover, $^1$H-NMR (400 MHz, CDCl$_3$) analysis of Compound A showed that δ9.57 (3H, m, CONHPh), 7.97 (1H, m, CONHCH$_2$), 6.87(6H, m, aromatic), 6.67 (3H, d, J=7.7 Hz, aromatic), 6.21 (3H, d, J=7.7 Hz, aromatic), 4.98 (6H, bs, NH$_2$), 3.67 (2H, d, J=5.1 Hz, Gly-C H$_2$), 3.56 (1H, m, SSCH), 3.16-3.04 (2H, m, CH$_2$SS), 2.36 (1H, m, CH$_2$CH$_2$SS), 2.25 (6H, m, CCH$_2$CH$_2$CO), 2.19-2.07 (2H, m, CH$_2$CH$_2$CONHCH$_2$), 1.93 (6H, m, CCH$_2$CH$_2$CO), 1.83 (1H, m, CH$_2$CH$_2$SS), 1.50 (4H, m, CH$_2$(CH$_2$)$_3$CONH, (CH$_2$)$_2$CH$_2$CH$_2$CONH), 1.33 (2H, m, CH$_2$C H$_2$(CH$_2$)$_2$CONH). These results confirmed the structure of Compound A. In addition, Compound A was found to have a molecular mass of 762.33.

Next, using linker compound A thus obtained, a ligand conjugate (Compound 1) was prepared, the ligand conjugate (Compound 1) having a structure as represented in General Formula (12) where n$^1$ was 1, X was a structure represented by General Formula (2), and m$^1$, m$^2$, and m$^3$ were 2 was synthesized as shown in Formula (24):

(24)

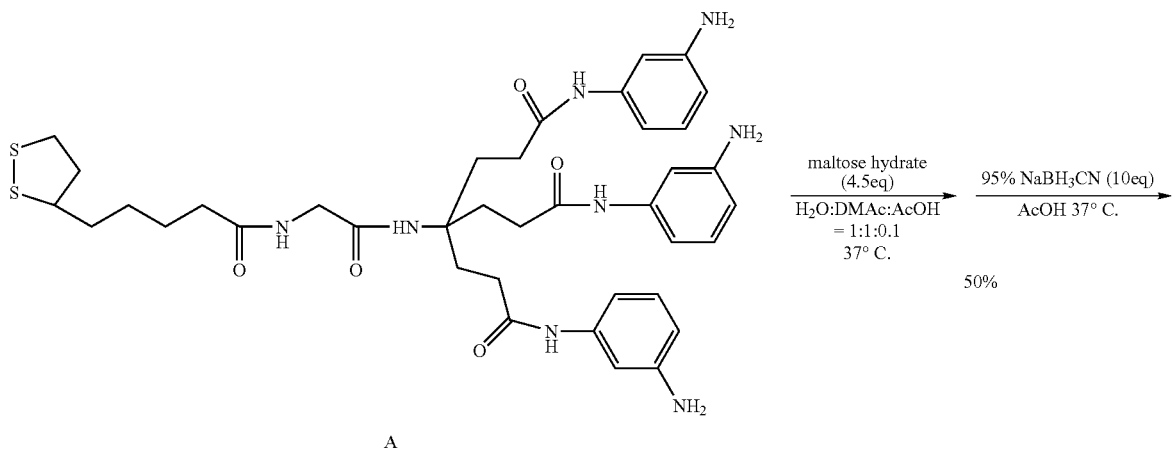

A

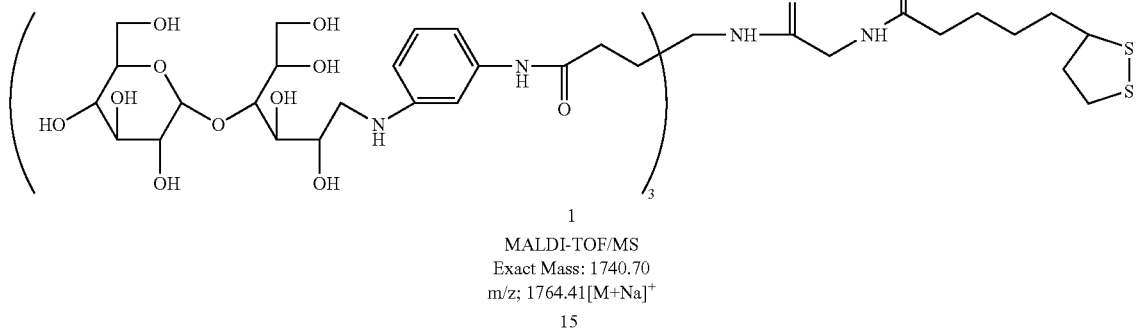

MALDI-TOF/MS
Exact Mass: 1740.70
m/z; 1764.41[M+Na]+

As shown in Formula (24), linker compound A thus obtained, and a commercially available maltose hydrate (4.5 equivalent), which was an oligosaccharide represented by Formula (18) were dissolved in a mixture solvent of $H_2O$/dimethylacetoamide (DMAc in formula)/acetic acid (AcOH)=1/1/0.1. Then, Schiff base was formed at pH 4 to 4.5 and a temperature of 37° C. Then, AcOh was added to the solvent. After 95% $NaBH_3CN$ of 10 equivalent was added therein, reductive amination was carried out at pH 3 to 4.5 and a temperature of 37° C. Then, the resultant was purified via gel filtration chromatography using Sphadex G-50 (Amersham biosystems), and subjected to desalting, thereby obtaining Compound 1, which was a ligand conjugate having three units of α-glucopyranose at its ends. The identification of Compound 1 was conducted via MALDI-TOF/MS and NMR.

MALDI-TOF/MS of Compound 1 showed that m/z was 1764.414 [(M+Na)+]. Further, $^1$H-NMR spectrometer (600 MHz, $D_2O$) showed that δ7.01 (3H, dd, J=8.2, 8.2 Hz, aromatic), 6.70 (3H, s, aromatic), 6.58 (3H, d, J=8.2 Hz, aromatic), 6.44 (3H, d, J=8.2 Hz, aromatic), 4.90 (3H, d, J=3.4 Hz, H-1'×3), 3.79-3.73 (6H, m, H-2×3, H-5×3), 3.71-3.66 (6H, m, H-3×3, H-5'×3), 3.64 (3H, dd, J=2.1, 12.4 Hz, H-6a'×3), 3.59 (3H, dd, J=4.8, 12.4 Hz, H-6b'×3), 3.59-3.52 (3H, m, H-6×3), 3.54-3.51 (6H, m, H-4×3, H-3'×3), 3.43 (3H, dd, J=6.9, 12.4 Hz, H-6b×3), 3.39-3.34 (1H, m, $CH_2$CH($CH_2$—)(S—)), 3.37 (3H, dd, J=3.4, 9.6 Hz, H-2'×3), 3.25 (3H, dd, J=9.6, 9.6 Hz, H-4'×3), 3.11 (3H, dd, J=4.8, 13.7 Hz, H-1a×3), 3.01 (3H, dd, J=7.7, 13.7 Hz, H-1b×3), 2.98-2.86 (2H, m, —$SCH_2$—), 2.27-2.23 (6H, m, —$CH_2CH_2$CO—×3), 2.19-2.14 (1H, m, —$SCH_2$CH_2(1H)—), 2.10 (2H, t, J=7.6 Hz, —NHCO$CH_2CH_2$—), 1.98-1.94 (6H, m, —$CH_2$CH_2CO—×3), 1.72-1.65 (1H, m, —$SCH_2$CH_2(1H)—), 1.43-1.36 (2H, m, —CO$CH_2$CH_2CH_2CH_2—), 1.39-1.29 (2H, m, —COCH_2CH_2CH_2CH_2—), 1.19-1.13 (2H, m, —COCH_2CH_2$CH_2$CH_2—). These results confirmed the structure of Compound 1. In addition, this Compound 1 was found to have a molecular mass of 1740.70.

(2) Synthesis of Second Ligand Conjugate (Compound 2)

A ligand conjugate (Compound 2), which was a second ligand conjugate, was synthesized as follows, the ligand conjugate (compound 2) having a structure represented by General Formula (12) where $n^1$ was 1, X was a structure represented by General Formula (2), R' was a hydrogen (H), and R was lactose shown in Formula (19), and $m^1$, $m^2$, and $m^3$ were 2.

The synthesis of the ligand conjugate (Compound 2) was carried out as follows. Firstly, linker compound A was synthesized as described above for the synthesis of the first ligand conjugate.

Subsequently, from the obtained linker compound A, the linker compound (Compound 2) was synthesized as shown in Formula (25), the ligand conjugate (compound 2) having a structure represented by General Formula (12) where $n^1$ was 1, X was a structure represented by General Formula (2), R' was a hydrogen (H), and R was lactose shown in Formula (19), and $m^1$, $m^2$, and $m^3$ were 2.

(25)

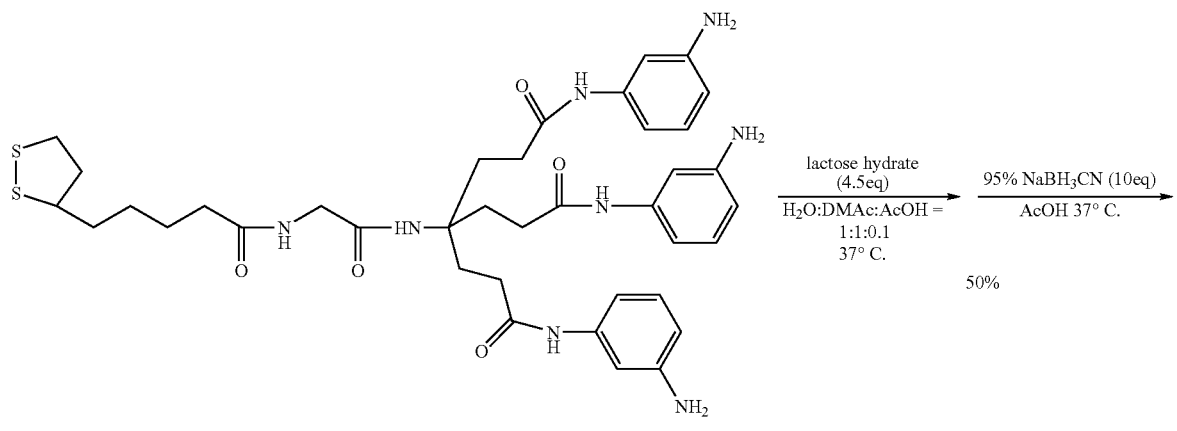

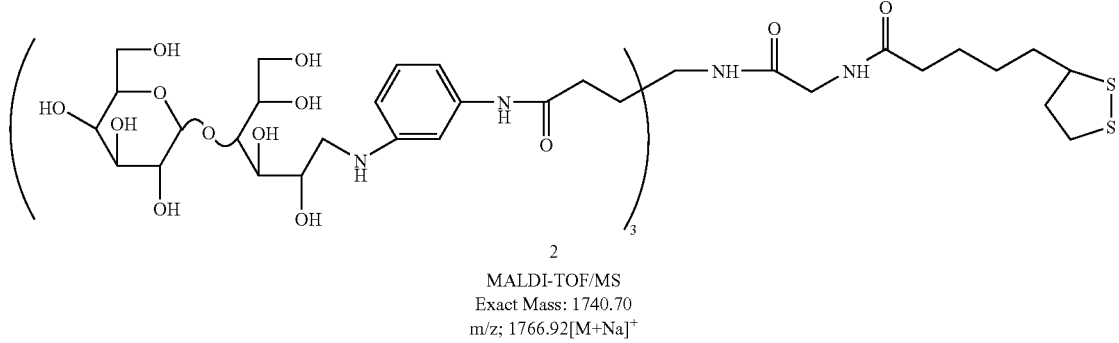

MALDI-TOF/MS
Exact Mass: 1740.70
m/z; 1766.92[M+Na]⁺

As shown in Formula (25), linker compound A thus obtained as above and a commercially available lactose hydrate (4.5 equivalent), which was an oligosaccharide represented by Formula (19) were dissolved in a mixture solvent of H₂O/dimethylacetoamide (DMAc in formula)/acetic acid (AcOH)=1/1/0.1. Then, Schiff base was formed at pH 4 to 4.5 and a temperature of 37° C. Then, AcOH was added to the solvent. After 95% NaBH₃CN of 10 equivalent was added therein, reductive amination was carried out at pH 3 to 4.5 and a temperature of 37° C. Then, the resultant was purified via gel filtration chromatography using Sphadex G-50 (Amersham biosystems), and subjected to desalting, thereby obtaining Compound 2, which was a ligand conjugate having three units of β-galactopyranose at its ends. The identification of Compound 2 was conducted via MALDI-TOF/MS and NMR.

MALDI-TOF/MS of Compound 2 showed that m/z was 1766.92 [(M+Na)⁺]. Further, ¹H-NMR spectroscopy (600 MHz, D₂O) showed that δ 6.99 (3H, dd, J=7.9, 8.2 Hz, aromatic), 6.70 (s, 3H, aromatic), 6.61 (3H, d, J=7.9 Hz, aromatic), 6.43 (3H, d, J=8.2 Hz, aromatic), 4.27 (3H, d, J=7.6 Hz, H-1'×3), 3.90-3.85 (3H, m, H-2×3), 3.74-3.70 (3H, m, H-5'×3), 3.69-3.66 (3H, m, H-4×3), 3.68-3.62 (3H, m, H-6a'× 3), 3.65-3.62 (3H, m, H-3×3), 3.57 (3H, br, H-4'×3), 3.53 (3H, dd, J=5.8, 11.7 Hz, H-6b'×3), 3.47-3.43 (6H, m, H-6×3), 3.41 (3H, m, J=3.1, 10.0 Hz, H-3'×3), 3.38 (3H, brt, J=5.8 Hz, H-5×3), 3.35 (3H, dd, J=7.6, 10.0 Hz, H-2'×3), 3.36-3.29 (1H, m, CH₂CH(CH₂—)(S—)), 3.12 (3H, brd, J=10.7 Hz, H-1ax 3), 2.91 (3H, dd, J=7.6, 12.0 Hz, H-1b×3), 2.90-2.83 (2H, m, —SCH₂—), 2.23-2.16 (6H, m, —CH₂CH₂CO—×3), 2.18-2.10 (1H, m, —SCH₂CH₂(1H)—), 2.06 (2H, t, J=5.8 Hz, —NHCOCH₂CH₂—), 1.95-1.89 (6H, m, —CH₂CH₂CO—×3), 1.68-1.59 (1H, m, —SCH₂CH₂(1H)—), 1.41-1.30 (2H, m, —COCH₂CH₂CH₂CH₂—), 1.32-1.22 (2H, m, —COCH₂CH₂CH₂CH₂—), 1.15-1.08 (2H, m, —COCH₂CH₂CH₂CH₂—). These results confirmed the structure of Compound 2. In addition, Compound 2 was found to have a molecular mass of 1740.70.

(3) Synthesis of Third Ligand Conjugate (Compound 3)

A ligand conjugate (Compound 3), which was a third ligand conjugate, was synthesized as below, the ligand conjugate having a structure represented by General Formula (12), where n¹ was 1, X was a structure represented by General Formula (3), R' was a hydrogen, R was maltose as shown in Formula (18), and m⁴ and m⁵ were 2.

As a pre-preparation of the synthesis of the ligand conjugate (Compound 3), linker compound B having two branches, each of which had an aromatic amino group end protected with a protection group was synthesized.

As shown in Formula (26), amino benzoic acid derivative (B-2), in which an amino group of an amino benzoic acid (B-1) was protected with a Boc group, and diethylenetriamine (B-3) were condensed with HOBt and EDC-HCL, thereby obtaining diamido compound with a yield of 79%. The diamido compound (B-4) was reacted with glycine whose amino group was protected with Z group, using, in DMF, FDPP as a condensing agent, thereby to obtain (B-5) with a yield of 75%. The Z group was removed by catalytic hydrogen reduction, thereby obtaining (B-6). After that, (B-6) was condensed with thioctic acid (B-7), thereby obtaining (B-8) with a yield of 97%. Finally, the Boc group was removed by TFA, thereby obtaining, with a yield of 95%, linker compound B having two units of aromatic amino group.

(26)

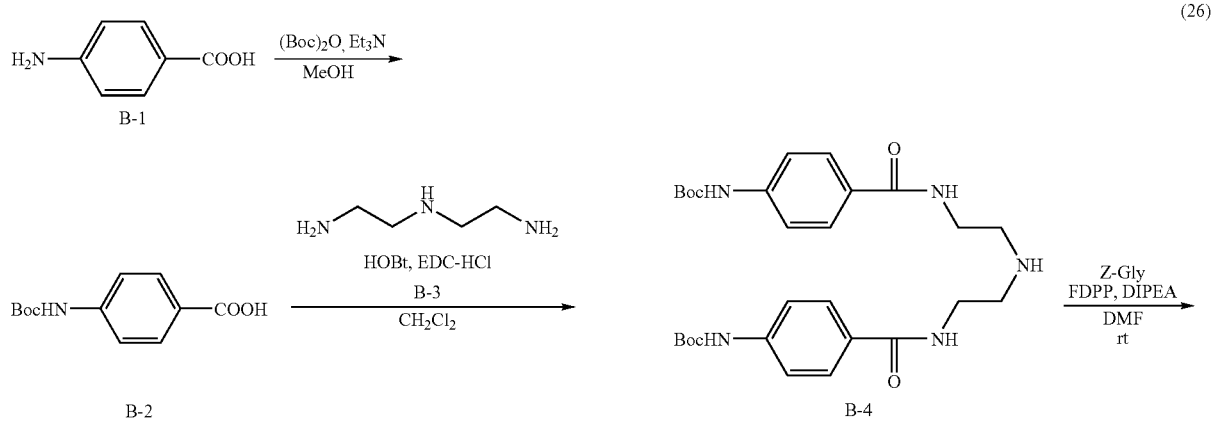

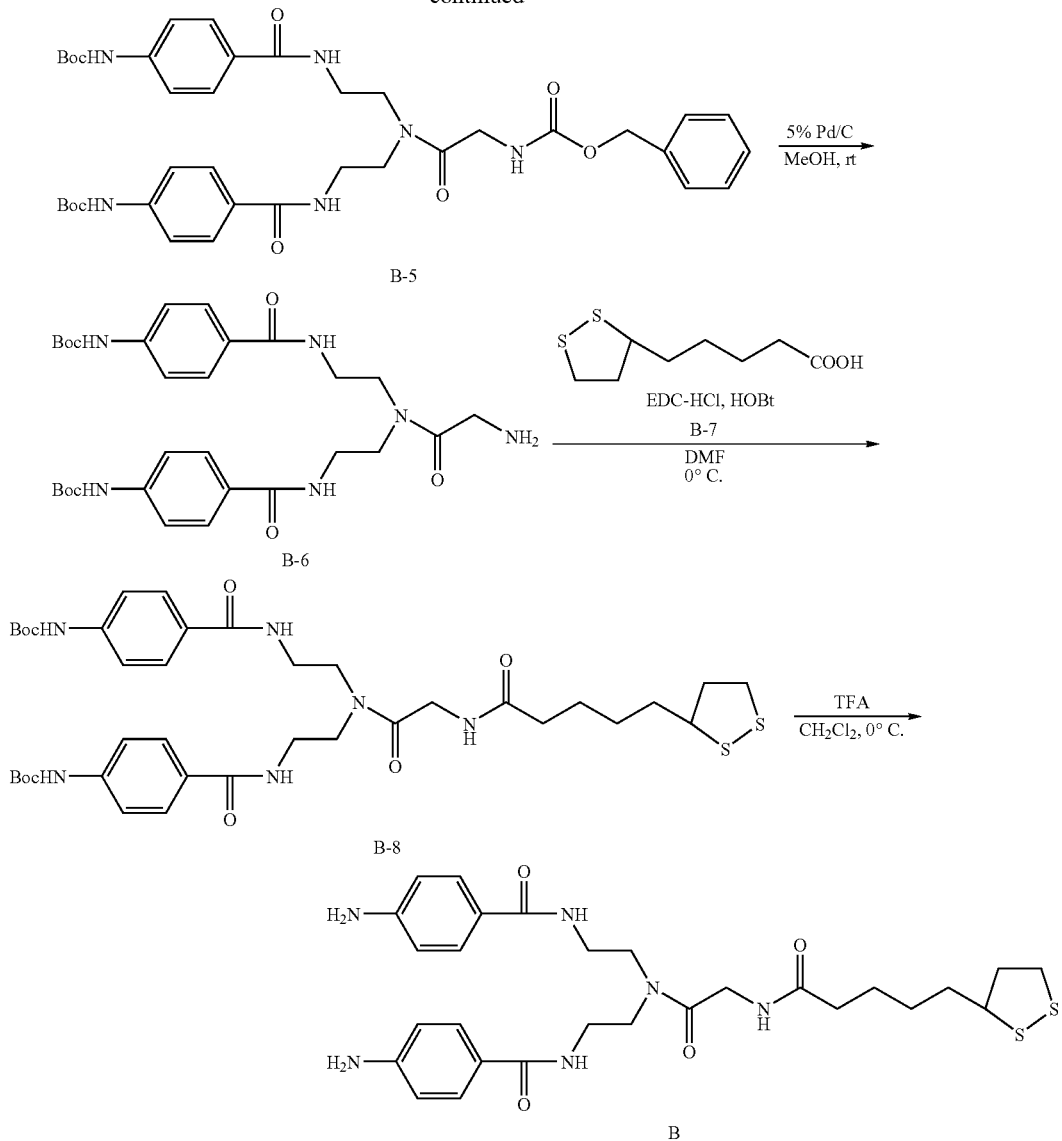

More specifically, Compound B-2 was obtained as follows. 4-amino benzoic acid (B-1) (2.00 g, 14.6 mmol) was dissolved in 140 mL of methanol. Then, (Boc)$_2$O (6.7 mL, 29.1 mmol) and triethylamine (3.06 mL, 21.9 mmol) were added therein and stirred for 16 hours at room temperature. The reaction solution was concentrated under reduced pressure, thereby obtaining a residue. Hexane and saturated sodium hydrogen carbonate aqueous solution (50 mL) was added to the residue thereby performing extraction to obtain a water layer. The water layer was mixed with 10% sodium citric acid aqueous solution until pH 4 was obtained, thereby precipitating out white solid. The thus obtained solid was dissolved in ethyl acetate and washed with water. The resultant was concentrated under reduced pressure. The residue from the concentration was recrystallized in ethyl acetate-hexane, thereby obtaining Compound B-2 (3.25 g, Yield: 91.3%) in the form of colorless crystals.

$^1$H-NMR (270 MHz, CD$_3$OD) analysis of the thus obtained Compound B-2 showed that δ9.24 (1H, s, NH), 7.96 (2H, d, J=8.9 Hz, aromatic), 7.55 (2H, d, J=8.6 Hz, aromatic), 1.56 (9H, s, t-butyl). Moreover, ESI-MS (negative) analysis of Compound B-2 showed that m/z was 236.20 [(M−H)$^-$].

These results confirmed the structure of Compound B-2. In addition, Compound B-2 was found to have a molecular mass of 237.25.

Next, Compound B-2 (1.30 g, 5.46 mmol), HOBt (0.738 g, 5.46 mmol), and EDC.HCl (1.05 g, 5.46 mmol) were dissolved in anhydrous dichloromethane (30 mL), and then stirred for 50 minutes at 0° C. under the argon atmosphere. Into the solution thus prepared, diethylenetriamine (B-3) (0.283 mL, 2.60 mmol) was added and stirred over night at room temperature in the dark, thereby obtaining white crystal. The white crystal was separated by filtration and then recrystallized in methanol, thereby to obtain Compound B-4 (1.23 g, Yield: 87.4%) in the form of white crystal.

$^1$H-NMR (400 MHz, CD$_3$OD) analysis of Compound B-4 thus obtained showed that δ7.77-7.74 (4H, d, J=8.67 Hz, aromatic), 7.50-7.48 (4H, d, J=8.57 Hz, aromatic), 3.70-3.66 (4H, m, J=5.19 Hz, NCH$_2$CH$_2$NHCO), 3.34-3.28 (4H, m, J=5.61 Hz, NCH$_2$CH$_2$NHCO), 1.53 (18H, s, t-butyl). Moreover, ESI-MS (positive) analysis of Compound B-4 showed that m/z was 542.64 [(M+H)$^+$]. This confirmed the structure of Compound B-4. In addition, Compound B-4 was found to have a molecular mass of 541.60.

Next, Compound B-4 (1.03 g, 1.85 mmol), Z-glycine (0.430 g, 2.04 mmol) and FDPP (1.07 mg, 2.78 mmol) were dissolved in anhydrous dimethylformamide (8 mL). Then, diisopropylethylamine (0.36 mL, 2.78 mmol) was added therein, and stirred for 20 hours at room temperature under argon atmosphere, to obtain a reaction solution. This reaction solution was concentrated under reduced pressure, thereby obtaining a residue. The residue was dissolved in chloroform thereby to obtain an organic layer. The organic layer was washed with 10% citric acid, and then with saturated sodium hydrogen carbonate aqueous solution. After the washing, the organic layer was dried using anhydrous sodium sulfate. After the drying agent was filtered off, the filtrate was concentrated under reduced pressure. The residue of the concentration was purified via silica gel chromatography (50 g, chloroform: acetone=1:2), thereby obtaining Compound B-5 (1.02 g, Yield: 75.0%) in the form of white solid.

$^1$H-NMR (400 MHz, CDCl$_3$) analysis of Compound B-5 showed that δ7.88 (1H, bs, NHCOPh), 7.73-7.66 (10H, m, NHCOPh, aromatic), 7.56 (1H, bs, NHCOPh), 7.38 (4H, d, J=8.4 Hz, COPhNH), 7.34-7.29 (8H, m, aromatic), 5.37 (1H, bs, Gly-NH), 5.00 (2H, s, PhCH$_2$), 3.64 (4H, m, NCH$_2$CH$_2$NH, NCH$_2$CH$_2$NH), 3.49, 3.47 (4H, m, NCH$_2$CH$_2$NH), 3.43, 3.27, 3.17 (6H, bt, bt, bt, NCH$_2$CH$_2$NH), 1.50, 1.49 (36H, s, s, t-butyl). ESI-MS (positive) of Compound B-5 showed that m/z was 755. 36 [(M+Na)$^+$]. This confirmed the structure of Compound B-5. In addition, Compound B-5 was found to have a molecular mass of 732.32.

Next, Compound B-5 (0.193 g, 0.264 mmol) was dissolved in methanol (3 mL). After 10% Pd/C (120 mg) was added therein, the solution was stirred for 3 hours under hydrogen atmosphere. After Pd/C was filtered out, the filtrate was concentrated under reduced pressure, thereby obtaining Compound B-6 (0.230 g, Yield: 94.4%) in the form of white solid.

$^1$H-NMR (400 MHz, d$_6$-DMSO) analysis of Compound B-6 thus obtained showed that δ9.54 (4H, d, J=9.5 Hz, COPhNH), 8.58, 8.53, 8.46 (4H, bs, bs, bs, NHCOPh), 8.10 (2H, bs, NH$_2$), 7.56 (1H, bs, NHCOPh), 7.76-7.73 (8H, m, aromatic), 7.53-7.48 (8H, m, aromatic), 4.39, 4.24 (4H, bs, bs, CONCH$_2$), 3.80 (2H, bs, CH$_2$NH$_2$), 3.42-3.33 (16H, m, NCH$_2$CH$_2$NH, NCH$_2$CH$_2$NH), 1.46, 1.45 (36H, s, s, t-butyl). ESI-MS (positive) analysis of Compound B-6 showed that m/z was 599.33 [(M+H)$^+$]. This confirmed the structure of Compound B-6. In addition, Compound B-6 was found to have a molecular mass of 598.39.

Subsequently, thioctic acid (B-7) (41.0 mg, 0.200 mmol), HOBt (35.0 mg, 0.200 mmol) and EDC.HCl (42.1 g, 0.200 mmol) was dissolved in dimethylformamide (3 mL), and then stirred for 1.5 hours at 0° C. in the dark under nitrogen atmosphere, thereby preparing a dimethylformamide solution. Then, Compound B-6 (0.1 g, 0.167 mmol) was dissolved in dimethylformamide (2 mL) and then dropped into the dimethylformamide solution, and then stirred for 19 hours at room temperature. Chloroform was added in the reaction solution thus obtained and extraction was performed to obtain an organic layer. The organic layer was washed with 10% citric acid aqueous solution and saturated sodium hydrogen carbonate aqueous solution, and then dried using anhydrous sodium sulfate. After the drying agent was filtered off, the filtrate was concentrated under reduced pressure. The residue of the concentration was purified via silica gel chromatography (50 g, chloroform:methanol=7:1), thereby obtaining Compound B-8 (0.128 g, Yield: 97.0%) in the form of white solid.

$^1$H-NMR (400 MHz, CDCl$_3$) analysis of Compound B-8 thus obtained showed that δ7.76-7.69 (11H, m, NHCOPh, aromatic), 7.55 (1H, bs, NHCOPh), 7.45-7.35 (9H, m, aromatic, COPhNH), 7.13, 7.00, 6.97 (3H, bs, bs, bs, COPhNH), 5.83 (1H, bs, Gly-NH), 4.04 (2H, bs, Gly-CH$_2$), 3.73-3.66 (4H, m, CONCH$_2$), 3.54-3.46 (11H, m, NCH$_2$CH$_2$NH, NCH$_2$CH$_2$NH, SSCHCH$_2$), 3.41, 3.29, 3.22(6H, bs, bs, bs, NCH$_2$CH$_2$NH), 3.16-3.03 (2H, m, CH$_2$SSCH), 2.39 (1H, m, CH$_2$CH$_2$SS), 2.02 (2H, t, J=6.9 Hz, CH$_2$CH$_2$CH$_2$CONH), 1.84 (1H, m, CHCH$_2$SS), 1.58-1.52 (4H, m, CH$_2$CH$_2$CH$_2$CONH, CH$_2$CH$_2$CH$_2$CONH), 1.51, 1.49 (18H, s, s, t-butyl), 1.35 (2H, m, CH$_2$CH$_2$CH$_2$CH$_2$CONH). ESI-MS (positive) analysis of Compound B-8 showed that m/z was 809.33 [(M+Na)$^+$]. This confirmed the structure of Compound B-8. In addition, Compound B-8 was found to have a molecular mass of 787.30.

Compound B-8 (0.128 g, 0.16 mmol) was dissolved in dichloromethane (1 mL). After TFA (2 mL) was added therein, the solution was stirred for 1.5 hours at 0° C. in the dark, and then concentrated under reduced pressure, thereby obtaining a residue. The residue was dissolved in methanol and neutralized through a column Dowex Marathon A (OH$^-$ form), and then concentrated under reduced pressure, thereby obtaining Compound B (89.3 mg, Yield: 95.2%) in the form of yellow solid.

$^1$H-NMR (400 MHz, d$_6$-DNSO) of Compound B thus obtained showed that δ8.20, 8.07 (2H, m, NHCOPh), 7.83 (1H, t, J=5.5 Hz, Gly-NH), 6.51-6.48 (8H, m, aromatic), 5.57 (8H, d, J=14.3 Hz, PhNH$_2$), 4.34, 4.12 (4H, bs, bs, CONCH$_2$), 3.82 (2H, bs, Gly-CH$_2$), 3.64-3.55 (1H, m, SSCHCH$_2$), 3.50-3.32 (16H, band, NCH$_2$CH$_2$NH, NCH$_2$CH$_2$NH), 3.18-3.04 (2H, m, CH$_2$SSCH), 2.38 (1H, m, CH$_2$CH$_2$SS), 2.02 (2H, t, J=7.1 Hz, CH$_2$CH$_2$CH$_2$CONH), 1.85 (1H, m, CH$_2$CH$_2$SS), 1.57-1.47 (4H, m, CH$_2$CH$_2$CH$_2$CONH, CH$_2$CH$_2$CH$_2$CH$_2$CONH), 1.35 (2H, m, CH$_2$CH$_2$CH$_2$CONH). Moreover, ESI-MS (positive) analysis of Compound B showed that m/z was 587.24 [(M+H)$^+$]. This confirmed the structure of Compound B. In addition, Compound B was found to have a molecular mass of 586.24.

Using linker compound B thus obtained, a linker conjugate (compound 3) was synthesized as shown in Formula (27), the linker conjugate (compound 3) having a structure represented by General Formula (12), where $n^1$ was 1, X had a structure represented by General Formula (3), R' was a hydrogen (H), R was maltose shown in Formula (18), and $m^4$ and $m^5$ were 2.

(27)

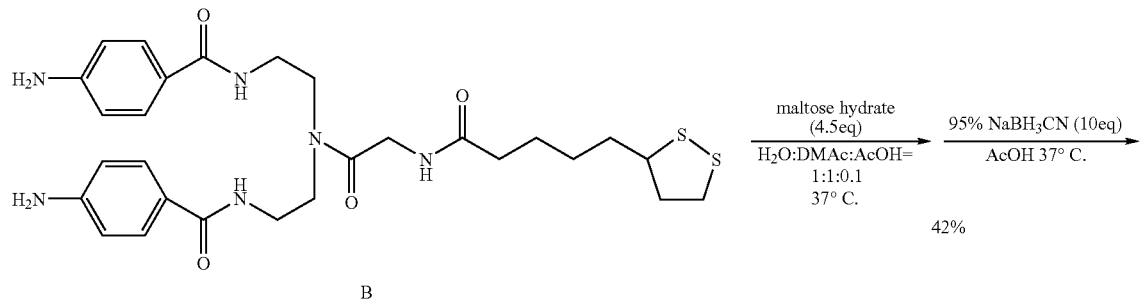

B

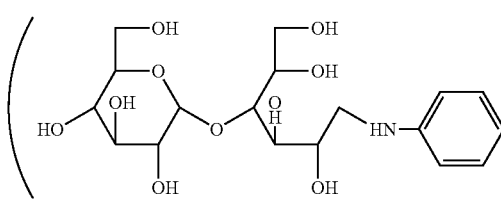
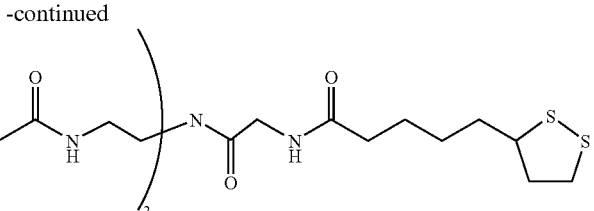

-continued

3
MALDI-TOF/MS
Exact Mass: 1238.48
Mol, Wt; 1239.36

As shown in Formula (27), linker compound B thus obtained above and a commercially-available maltose hydrate (4.5 equivalent), which was an oligosaccharide represented by Formula (18), were dissolved in a mixture solvent of $H_2O$/dimethylacetoamide (DMAc in the formula)/acetic acid (AcOH)=1/1/0.1. After forming a Shiff base at pH of 4 to 4.5 and a temperature of 37° C., AcOH was added to the solvent. Then, 10 equivalent of 95% $NaBH_3CN$ was added therein. After that, reductive amination was conducted at pH of 3 to 4.5 and a temperature of 37° C. Then, the resultant compound was purified by gel filtration chromatography using Sephadex G-50 (Amersham Biosystems) and then subjected to desalting thereby obtaining Compound 3, which was a ligand conjugate that has two units of α-glucopyranose at its ends. Identification of Compound 3 was carried out by MALDI-TOF/MS and NMR.

MALDI-TOF of Compound 3 showed that m/z was 1239.36-[(M+H)$^+$]. $^1$H-NMR spectroscopy (600 MHz, $D_2O$) showed that δ7.39 (2H, d, J=8.2 Hz, aromatic), 7.38 (2H, d, J=8.2 Hz, aromatic), 6.56 (2H, d, J=8.2 Hz, aromatic), 6.55 (2H, d, J=8.2 Hz, aromatic), 4.91 (2H, d, J=3.4 Hz, H-1'×2), 3.84 (2H, s, —NHCOC$\underline{H_2}$NH—), 3.83-3.78 (2H, m, H-2×2), 3.75 (2H, dd, J=4.1, 6.9 Hz, H-5×2), 3.72 (2H, dd, J=2.7, 4.8 Hz, H-3×2), 3.69 (2H, dd, J=4.1, 4.8 Hz, H-4×2), 3.69-3.66 (2H, m, H-5×2), 3.64 (2H, dd, J=2.1, 12.4 Hz, H-6a'×2), 3.58 (2H, dd, J=4.8, 12.4 Hz, H-6b'×2), 3.55-3.51 (2H, m, H-6a× 2), 3.53 (2H, dd, J=8.9. 9.6 Hz, H-3'×2), 3.47-3.40 (8H, m, —CONHC$\underline{H_2}$C$\underline{H_2}$N—×2), 3.44-3.41 (2H, m, H-6b×2), 3.37 (2H, dd, J=3.4, 9.6 Hz, H-2'×2), 3.37-3.30 (1H, m, $CH_2CH$ $(CH_2—)(S—)$), 3.23 (2H, dd, J=8.9, 10.3 Hz, H-4'×2), 3.20 (3H, dd, J=4.8, 13.7 Hz, H-1a×2), 3.12 (2H, dd, J=8.2, 13.7 Hz, H-1b×2), 3.00-2.89 (2H, m, —SC$\underline{H_2}$—), 2.22-2.15 (1H, m, —SCH$_2$C$\underline{H_2}$(1H)—), 1.98 (2H, t, J=6.9 Hz, —NHCO C$\underline{H_2}$CH$_2$—), 1.72-1.64 (1H, m, —SCH$_2$C$\underline{H_2}$(1H)—), 1.45-1.37 (1H, m, —COCH$_2$CH$_2$CH$_2$C$\underline{H_2}$(1H)—), 1.35-1.23 (3H, m, —COCH$_2$C$\underline{H_2}$CH$_2$CH$_2$—, —COCH$_2$CH$_2$CH$_2$ C$\underline{H_2}$(1H)—), 1.09-1.02 (2H, m, —COCH$_2$CH$_2$C$\underline{H_2}$CH$_2$—). These results confirmed the structure of Compound 3. In addition, Compound 3 was found to have a molecular mass of 1238.48.

(4) Synthesis of Fourth Ligand Conjugate (Compound 4)

A ligand conjugate (Compound 4), which was a fourth ligand conjugate, was synthesized as below, the ligand conjugate having a structure represented by General Formula (12), where $n^1$ was 1, X had a structure represented by General Formula (3), R' was a hydrogen (H), R was lactose represented by General Formula (19), $m^4$ and $m^5$ were 2.

As a pre-preparation of the synthesis of the ligand conjugate (Compound 4), linker compound B having two branches, each of which had an aromatic amino group end protected with a protection group was synthesized. Next, the ligand conjugate (Compound 4) was synthesized using the thus obtained linker compound B as shown in Formula (28), the ligand conjugate having a structure represented by General Formula (12), where $n^1$ was 1, X had a structure represented by General Formula (3), R' was a hydrogen (H), R was lactose represented by General Formula (19), and $m^4$ and $m^5$ were 2.

(28)

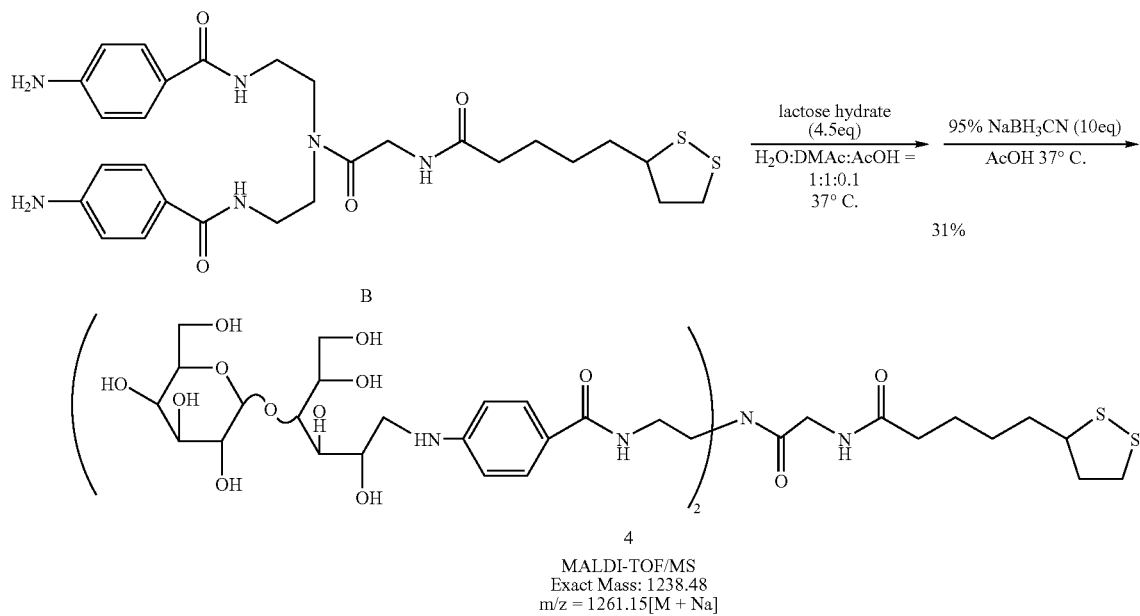

4
MALDI-TOF/MS
Exact Mass: 1238.48
m/z = 1261.15[M + Na]

As shown in Formula (28), linker compound B thus obtained and a commercially-available lactose hydrate (4.5 equivalent), which was an oligosaccharide represented by Formula (19), were dissolved in a mixture solvent of $H_2O$/dimethylacetoamide (DMAc in formula)/acetic acid (AcOH)=1/1/0.1. Then, Schiff base was formed at pH 4 to 4.5 and a temperature of 37° C. Then, AcOH was added to the solvent. After 95% $NaBH_3CN$ of 10 equivalent was added therein, reductive amination was carried out at pH 3 to 4.5 and a temperature of 37° C. Then, the resultant was purified via gel filtration chromatography using Sphadex G-50 (Amersham biosystems), and subjected to desalting, thereby obtaining Compound 4, which was a ligand conjugate having two units of β-galactopyranose at its ends. The identification of Compound 4 was conducted via MALDI-TOF/MS and NMR.

MALDI-TOF/MS of compound 4 showed that m/z was 1261.15-[(M+Na)$^+$]. Moreover, $^1$H-NMR spectroscopy (600 MHz, $D_2O$) showed that δ 7.40 (2H, d, J=8.9 Hz, aromatic), 7.39 (2H, d, J=8.9 Hz, aromatic), 6.59 (2H, d, J=8.9 Hz, aromatic), 6.58 (2H, d, J=8.9 Hz, aromatic), 4.30 (d, 1H, J=7.6 Hz, H-1'), 4.29 (1H, d, J=7.6 Hz, H-1'), 3.93-3.89 (2H, m, H-2×2), 3.84 (2H, s, —CONH$\underline{CH_2}$NH—), 3.74-3.71 (2H, m, H-5'×2), 3.71-3.69 (4H, m, H-4×2, H-4'×2), 3.69-3.66 (2H, m, H-3×2), 3.65 (2H, dd, J=3.0, 11.7 Hz, H-6a'×2), 3.53 (2H, dd, J=5.5, 11.7 Hz, H-6b'×2), 3.48-3.42 (12H, m, H-5×2, H-3'×2, —CONH$\underline{CH_2CH_2}$N-×2), 3.41-3.39 (4H, m, H-6×2), 3.37-3.32 (1H, m, $CH_2\underline{CH}(CH_2-)(S-)$), 3.35 (2H, dd, J=7.6, 8.9 Hz, H-2'×2), 3.23 (2H, dd, J=4.1, 13.7 Hz, H-1a× 2), 3.04 (2H, dd, J=7.6, 13.7 Hz, H-1b×2), 3.01-2.90 (2H, m, —$SCH_2$—), 2.23-2.16 (1H, m, —$SCH_2\underline{CH_2}$(1H)—), 1.99 (2H, t, J=6.9 Hz, —$NHCOCH_2CH_2$—), 1.73-1.66 (1H, m, —$SCH_2\underline{CH_2}$(1H)—), 1.46-1.39 (1H, m, —$COCH_2CH_2CH_2\underline{CH_2}$(1H)—), 1.35-1.30 (1H, m, —$COCH_2CH_2CH_2CH_2$(1H)—), 1.32-1.26 (2H, m, —$COCH_2\underline{CH_2}CH_2CH_2$—), 1.11-1.04 (2H, m, —$COCH_2CH_2\underline{CH_2}CH_2$—). These results confirmed the structure of Compound 4. In addition, Compound 4 was found to have a molecular mass of 1238.48.

Example 2

SPR Measurement and Mass Spectroscopy for Protein Analysis

In Example 2, binding properties between sugar chains and proteins were analyzed using the ligand conjugates prepared in Example 1 by SPR measurement and mass spectroscopy. The analysis was carried out as follows.

In FIG. 1, steps of the protein analysis in the present Example were denoted as steps 1 to 12. In FIG. 1, Steps 1 to 7 are steps for preparing a ligand carrier (sensor chip) by immobilizing a ligand conjugate (any of Compounds 1 to 4) onto a surface of a supporter coated with gold (Au). The steps carried out after Step 8 at which the ligand carrier was allowed to stand in contact with a solution containing a protein to be analyzed are steps for carrying out the SPR measurement. Furthermore, the steps carried out after Step 10 for washing the surface of the supporter with water are for identifying the protein via mass spectroscopy (MS).

In the present Example, the SPR measurement was conducted by using SPR-8B manufactured by Nippon laser electronics Co. The mass spectroscopy was carried out by using voyager RP-DE, which was a matrix-assisted laser desorption/time of flight mass spectrometer (MALDI-TOF/MS), made by Applied Biosystems.

The five proteins were analyzed, namely Concanavalin A (hereinafter, abbreviated as ConA), PSA, and LCD which are lectin proteins that can be bonded with glucopyranose, and RCA and PNA, which are lectin proteins that can be bonded with galactopyranose. Bovine serum albumin (BSA) was used as negative control.

Firstly, following Steps 1 to 7 in FIG. 1, 4 types of ligand carriers were prepared, on each of which Compound 1 to 4 were respectively immobilized. Next, protein solutions were prepared by respectively dissolving the 5 lectin proteins mentioned above and BSA in PBS buffer. Then, Step 8 in FIG. 1 was carried out so as to allow the respective ligand carriers to stand in contact with the respective protein solutions, in order that interaction might occur. Next, the SPR measurement was carried out so as to analyze the bonging between the ligand carriers and the proteins.

Figure 2:
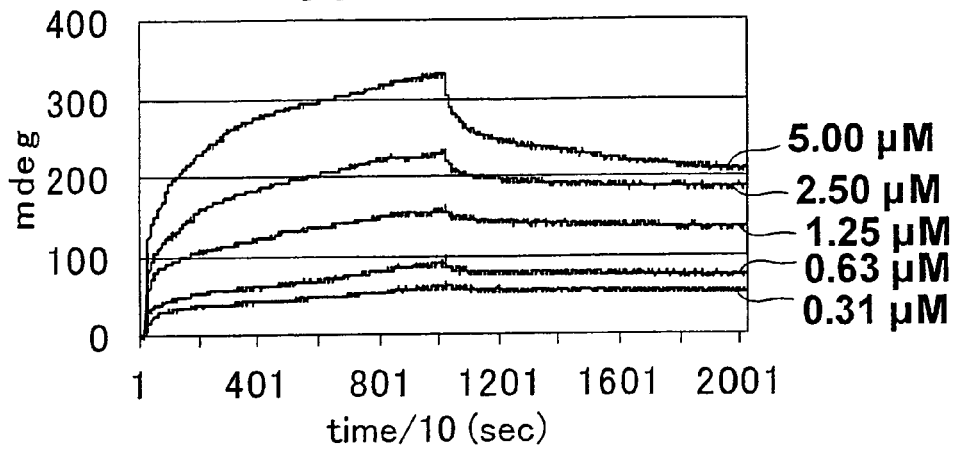
FIG. 2(a) is a graph illustrating results of analysis on bonding behavior of ConA, using a sensor chip on which a ligand conjugate having two molecules of α-glucopyranose was immobilized.
FIG. 2(b) is a graph illustrating results of analysis on bonding behavior of PSA, using a sensor chip on which a ligand conjugate having two molecules of α-glucopyranose was immobilized.
FIG. 2(c) is a graph illustrating results of analysis on bonding behavior of LCA, using a sensor chip on which a ligand conjugate having two molecules of α-glucopyranose was immobilized.
Figure 2:
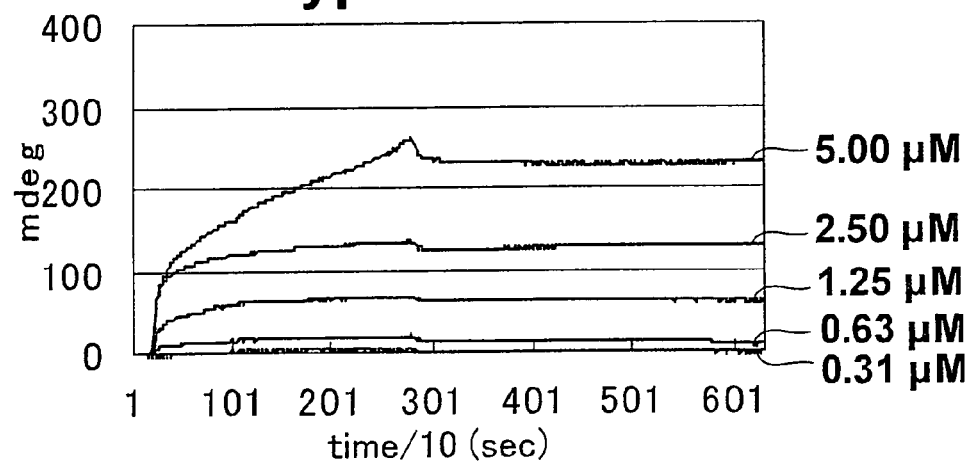
Figure 2:
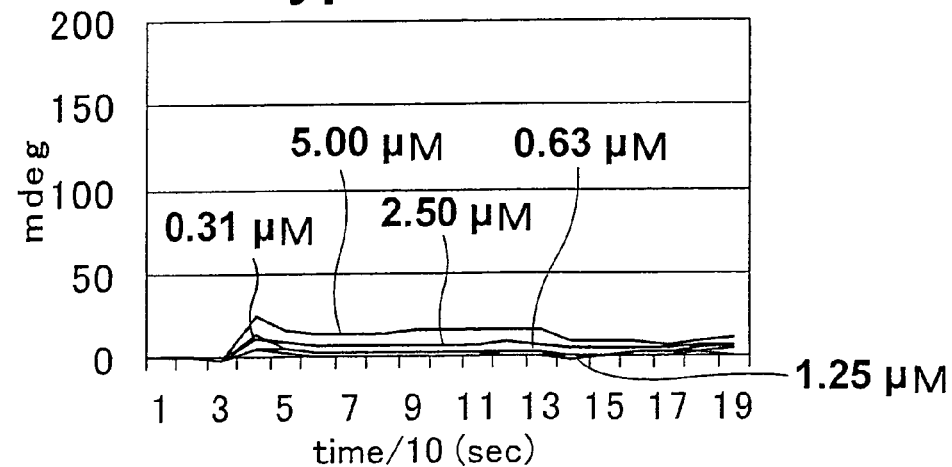
Figure 3:
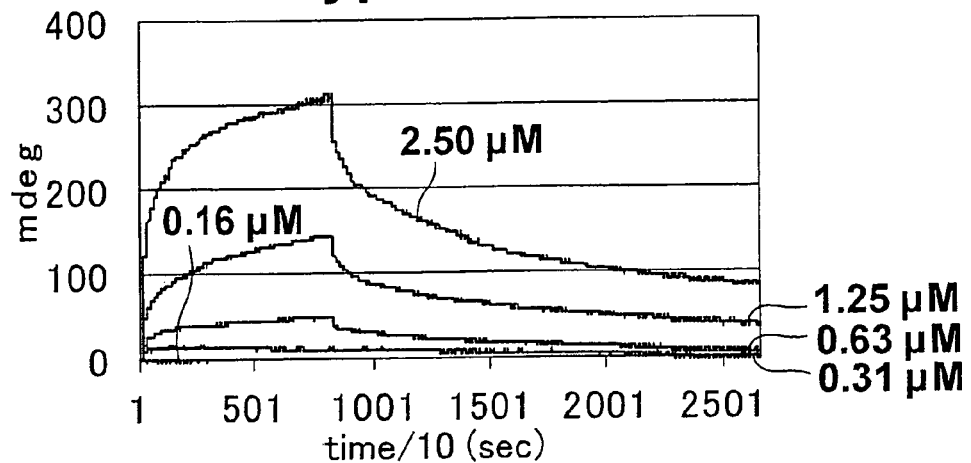
FIG. 3(a) is a graph illustrating results of analysis on bonding behavior of ConA, using a sensor chip on which a ligand conjugate having three molecules of α-glucopyranose was immobilized.
FIG. 3(b) is a graph illustrating results of analysis on bonding behavior of PSA, using a sensor chip on which a ligand conjugate having three molecules of α-glucopyranose was immobilized.
FIG. 3(c) is a graph illustrating results of analysis on bonding behavior of LCA, using a sensor chip on which a ligand conjugate having three molecules of α-glucopyranose was immobilized.
Figure 3:
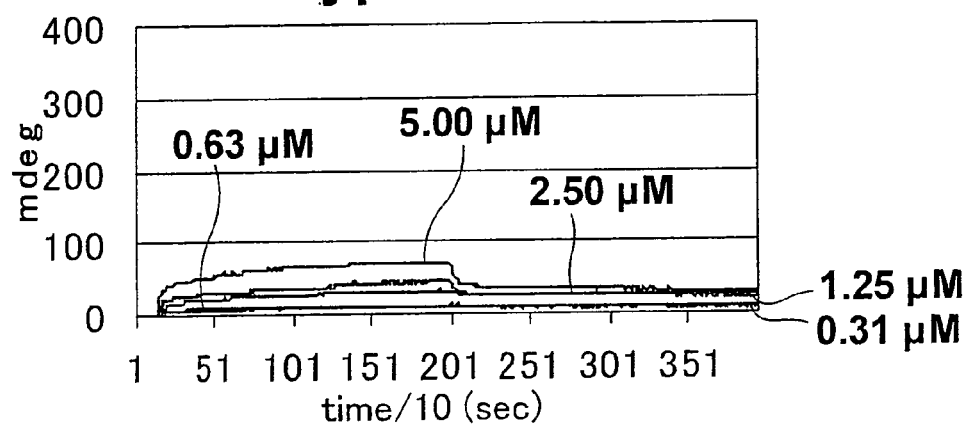
Figure 3:
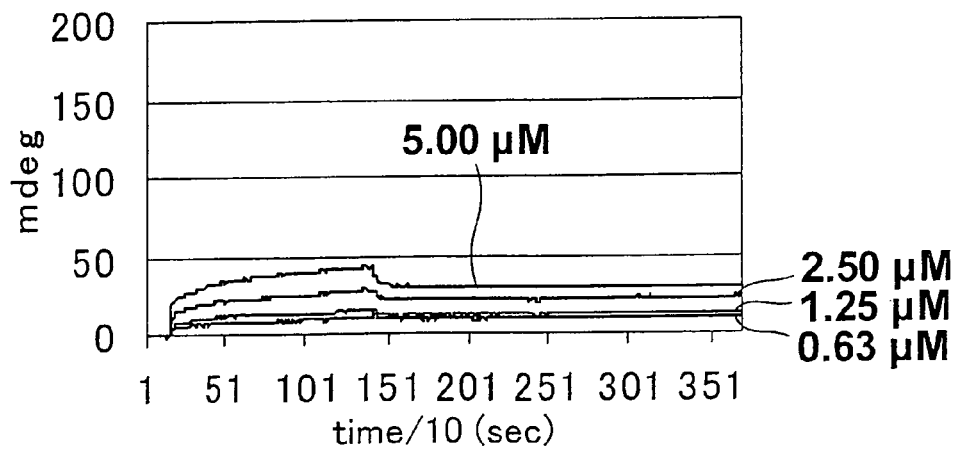

FIGS. 2 and 3 and Table 1 shows results of bonding behaviors of the lectin proteins with respect to the ligand carriers (sensor chips) on which α-glucopyranose was immobilized. FIG. 2 shows the results for the sensor chip on which the ligand conjugate of Compound 3 (Di-valent type) was immobilized. FIG. 3 shows the results for the sensor chip on which the ligand conjugate of Compound 1 (Tri-valent type) was immobilized. Both in FIGS. 2 and 3, (a) shows the bonding behavior of ConA, (b) shows the bonding behavior of PSA, and (c) shows the bonding behavior of LCA.

TABLE 1

|  | Di-Valent Type | | | Tri-Valent Type | | |
| --- | --- | --- | --- | --- | --- | --- |
|  | $K_D$ | $K_a$ | $K_d$ | $K_D$ | $K_a$ | $K_d$ |
| Con A | 11.33 | 0.45 | 0.51 | 4.34 | 1.95 | 0.85 |
| PSA | 8.58 | 0.87 | 0.75 | 9.86 | 2.34 | 1.01 |
| LCA | No bonding | | | 6.04 | 2.40 | 1.45 |
| RCA | No bonding | | | No bonding | | |
| PNA | No bonding | | | | | |

$K_D$: Dissociation Constant (μM)
$K_a$: Assosication Rate Constant ($M^{-1}s^{-1} \times 10^4$)
$K_d$: Dissosicaiton Rate Constant ($s^{-1} \times 10^1$)

As understood from FIGS. 2 and 3, ConA and PSA showed similar bonding behaviors for both the sensor chips regardless of the difference in the structures of the linker portions of the ligand conjugates. However, LCA could bond with Compound 1, which was a ligand conjugate having three units of sugar molecules, but not with Compound 3, which was a ligand conjugate having two units of sugar molecules. Even though it is not illustrated here, it was found that the negative control BSA did not bind with the chips to which Compound 1 or 3 was immobilized.

Moreover, in Table 1, the bonding behaviors of the respective proteins are shown collectively. It was observed that the lectin proteins that can bind with α-glucose was specifically bonded. Further, it was possible to calculate out binding constant for the lectin proteins that can bind with α-glucose. The calculation showed that dissociation constant ($K_D$) for Tri-valent ligand bonding substance was equivalent to or smaller than that for Di-valent ligand bonding substance. Thus, it was understood that an increase in the number of sugar chains per ligand conjugate leads to a greater binding activity.

Figure 4:
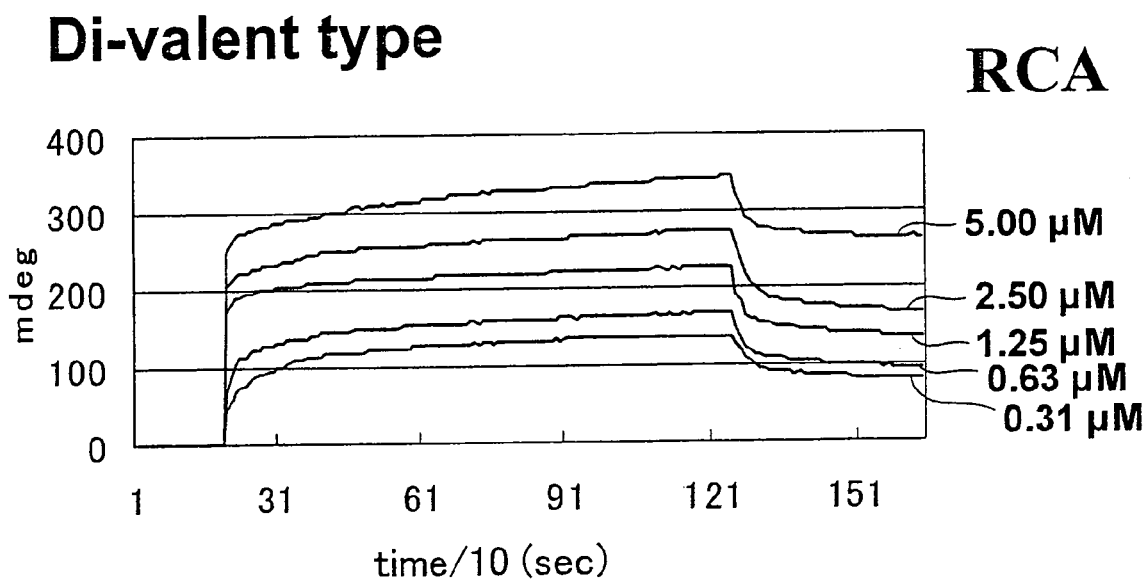
FIG. 4(a) is a graph illustrating results of analysis on bonding behavior of RCA, using a sensor chip on which a ligand conjugate having two molecules of β-galactopyranose was immobilized.
FIG. 4(b) is a graph illustrating results of analysis on bonding behavior of PNA, using a sensor chip on which a ligand conjugate having two molecules of β-galactopyranose was immobilized.
Figure 4:
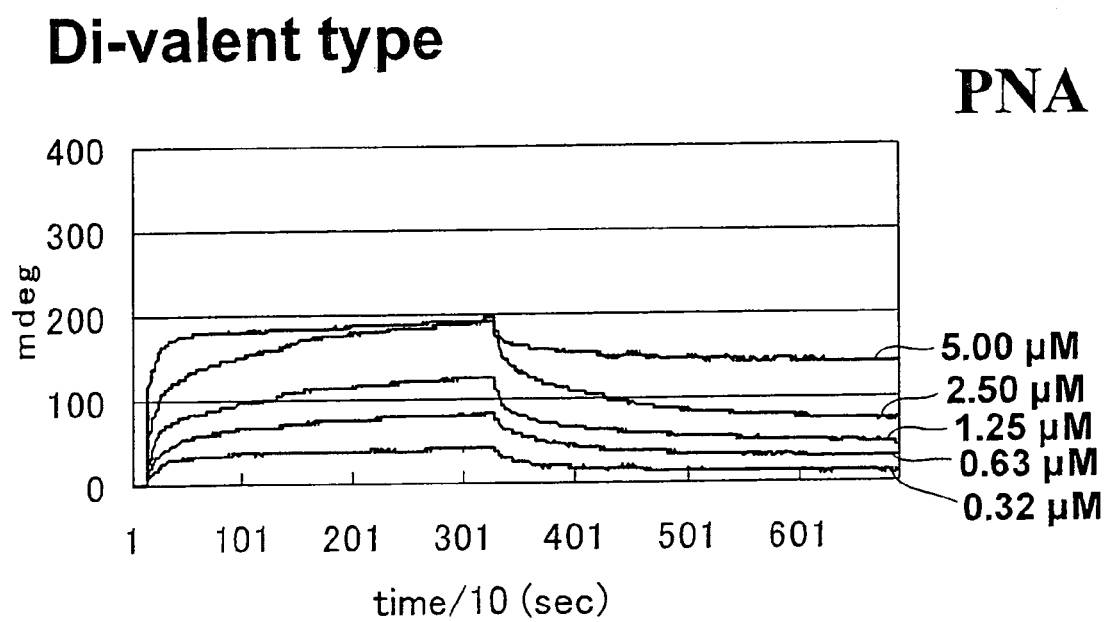
Figure 5:
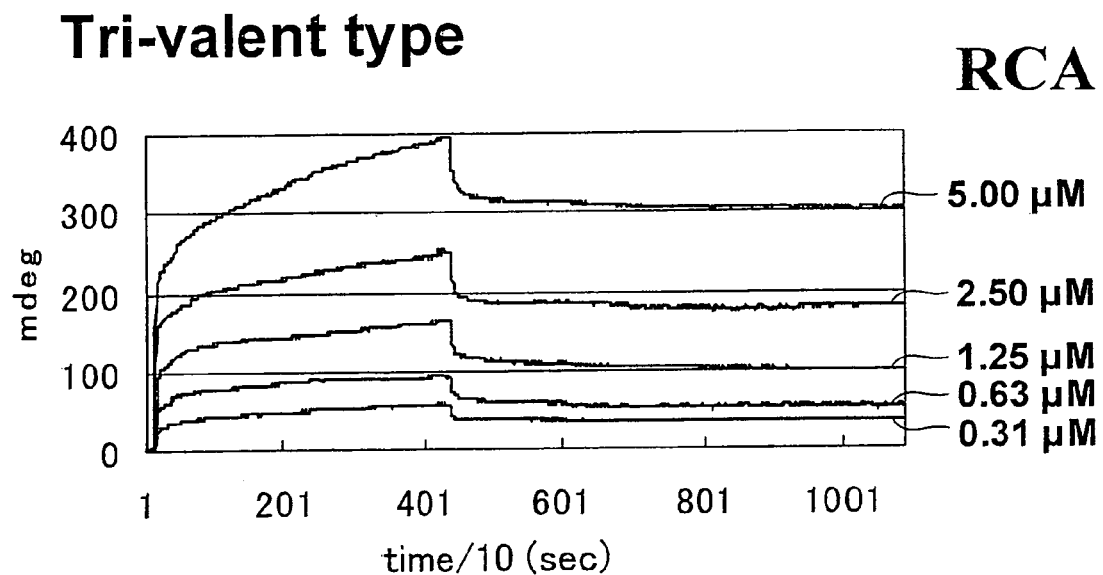
FIG. 5(a) is a graph illustrating results of analysis on bonding behavior of RCA, using a sensor chip on which a ligand conjugate having three molecules of β-galactopyranose was immobilized.
FIG. 5(b) is a graph illustrating results of analysis on bonding behavior of PNA, using a sensor chip on which a ligand conjugate having three molecules of β-galactopyranose was immobilized.
Figure 5:
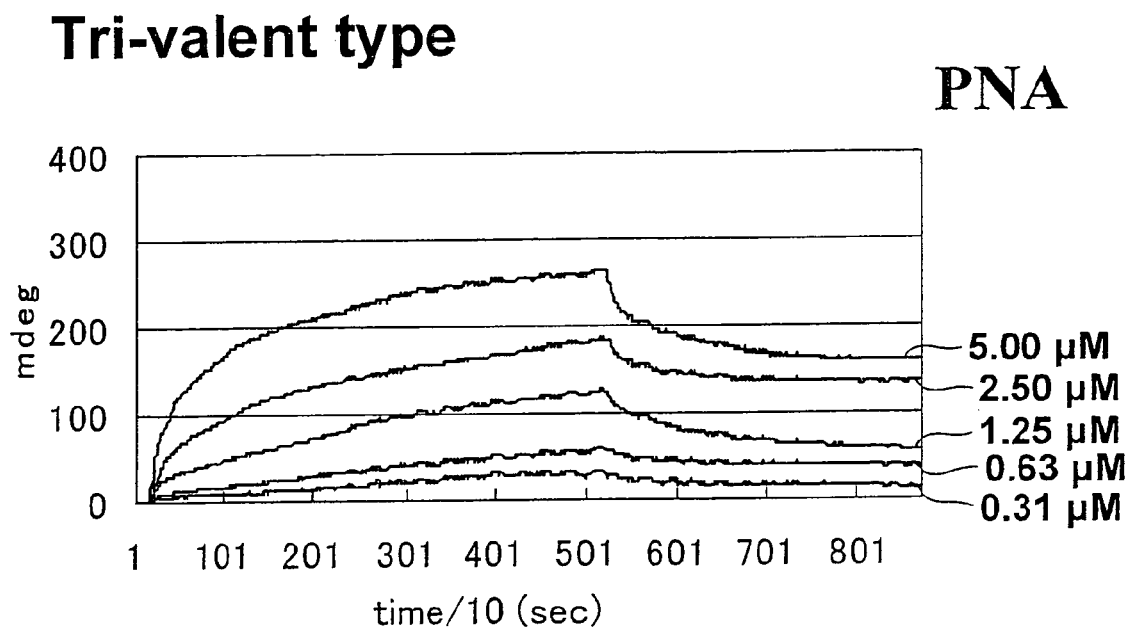

FIGS. 4 and 5 and Table 2 show bonding behaviors of the lectin proteins with respect to the ligand carriers (sensor chips) on which β-galactopyranose was immobilized. FIG. 4 shows the results for the sensor chip on which the ligand conjugate of Compound 4 (Di-valent type) was immobilized. FIG. 5 shows the results for the result for the sensor chip on which the ligand conjugate of Compound 2 (Tri-valent type) was immobilized. Both in FIGS. 4 and 5, (a) shows the bonding behavior of RCA, and (b) shows the bonding behavior of PNA.

TABLE 2

| | Di-Valent Type | | | Tri-Valent Type | | |
|---|---|---|---|---|---|---|
| | $K_D$ | $K_a$ | $K_d$ | $K_D$ | $K_a$ | $K_d$ |
| Con A | No bonding | | | *1 | | |
| PSA | No bonding | | | No bonding | | |
| LCA | No bonding | | | No bonding | | |
| RCA | 12.23 | 0.74 | 0.61 | 7.79 | 0.52 | 0.41 |
| PNA | 4.95 | 1.71 | 0.85 | 5.83 | 1.98 | 1.15 |

$K_D$: Dissociation Constant (μM)
$K_a$: Assosication Rate Constant ($M^{-1}s^{-1} \times 10^4$)
$K_d$: Dissosicaiton Rate Constant ($s^{-1} \times 10^1$)
*1: Non-specific adsorption independent of protein concentrain was observed As understood from FIGS. 4 and 5, RCA and PNA showed similar bonding behaviors for both the sensor chips regardless of the difference in the structures of the linker portions of the ligand conjugates. Even though it is not illustrated here, it was found that the negative control BSA did not bind with the chips to which Compound 2 or 4 was immobilized.

Moreover, in Table 2, the bonding behaviors of the respective proteins are shown collectively. It was observed that the lectin proteins that can bind with β-glucose was specifically bonded. Further, it was possible to calculate out binding constant for the lectin proteins that can bind with β-galactose. Moreover, non-specific bonding behavior of ConA independent of the concentration of the proteins was observed when the chip with Compound 3 was used. The calculation showed that dissociation constant ($K_D$) for Tri-valent ligand bonding substance was equivalent to or smaller than that for Di-valent ligand bonding substance. Thus, it was understood that an increase in the number of sugar chains per ligand conjugate leads to a greater binding activity.

From these results, it was understood that the bonding activity of proteins with respect to sugar chains would be different depending on how many sugar chains are present. It was shown that the sugar chain bonding properties of lectin proteins could be measured with this system.

Further, the ligand carriers that the SPR measurement confirmed their bonding with the proteins were further analyzed with the mass spectrometer after Steps 9 and 10. Thereby the proteins bonded with the ligand carriers were identified. In the mass spectroscopy, molecular mass of the sample was measured with the mass spectrometer after the sample was treated such that a matrix solution (saturated αCHAA or sinapic acid) was placed on the part at which the bonding was measured, and dried.

After conducting the series of steps to confirm the bonding behavior between a ligand carrier and a protein, the bonding between the ligand carrier and the protein was dissociated at Step 11, and washing with PBS buffer was carried out at Step 12. After that, Steps 8 to 10 were repeated with another protein solution, and then the SPR measurements and mass spectroscopy were carried out. This was repeated for each ligand carrier and protein.

Figure 6:
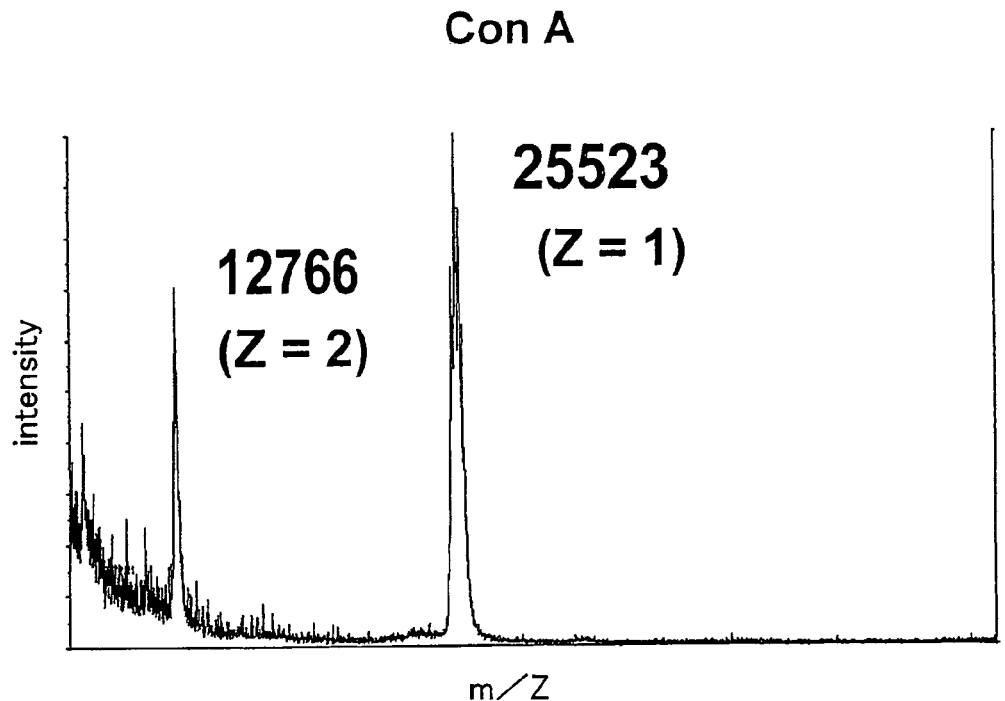
FIG. 6(a) is a chart illustrating a result of mass spectroscopy of ConA bound on a sensor chip.
FIG. 6(b) is a chart illustrating a result of mass spectroscopy of PNA bound on a sensor chip.
Figure 6:
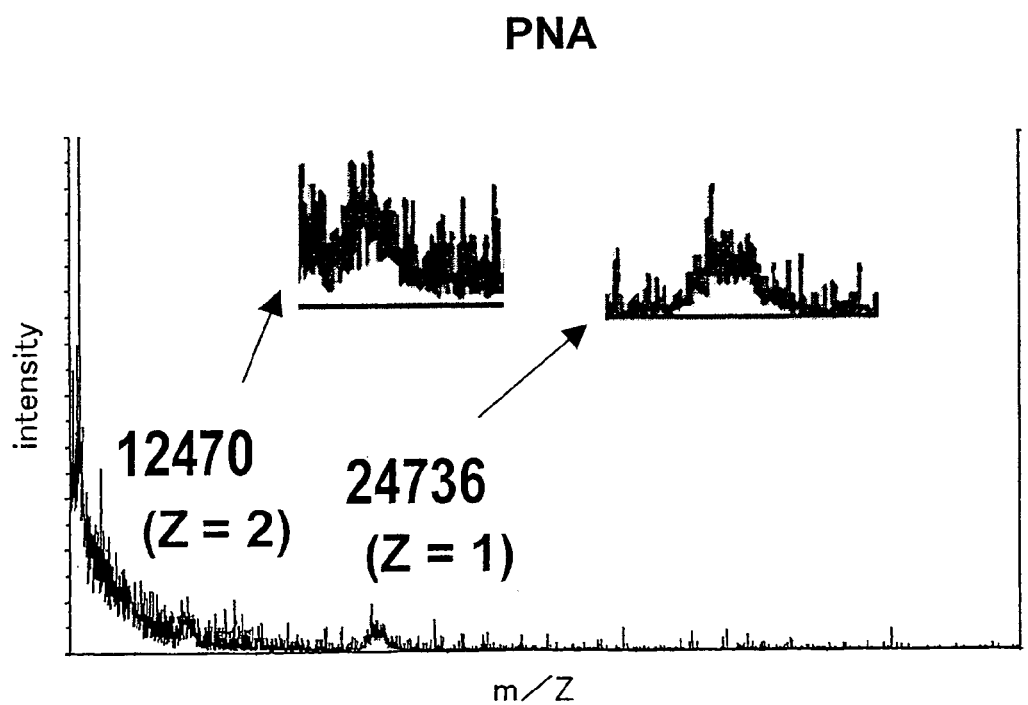

The results of the mass spectroscopy are shown in FIG. 6 and Table 3. FIG. 6(*a*) shows the result of the analysis for ConA, meanwhile FIG. 6(*b*) shows the result of the analysis for PNA.

TABLE 3

| Lectin Protein | Molecular weight | Found (m/z) |
|---|---|---|
| Con A | 104000 ($\alpha_4$) | 25523 (α chain) |
| | 25572 (α) | |
| PSA | 50000 ($\alpha_4\beta_2$) | 5801 (α chain) |
| | 6000 (α) | 19210 (β chain) |
| | 18000 (β) | |
| LCA | 46000 ($\alpha_2\beta_2$) | 5742 (α chian) |
| | 5710 (α) | 8594 (β chain, 2+) |
| | 17572 (β) | |
| PNA | 98000 ($\alpha_4$) | 24736 (αchain) |
| | 24500 (α) | |
| RCA | 120000 ($\alpha_2\beta_2$) | Not Detected |
| | 31000 (α) | |
| | 32000 (β) | |

As shown in FIGS. 6(*a*) and 6(*b*), ion peaks were found that correspond molecular masses of monovalent or divalent ions corresponding to subunits that constitute the respective proteins.

Moreover, Table 3 shows the results for the other lectin proteins. Ion peaks were found in the vicinity of the molecular masses of monovalent or divalent ions corresponding to the subunits of the lectin proteins. However, for RCA, the mass spectrometer used could not detect the ion peak of the subunit of RCA because the subunit of RCA had a large molecular mass of 30,000 or more Dalton. It was predicted that the ion peak could be detected by using an MALDI-TOF/MS apparatus of a higher performance.

The mass spectroscopy found the molecular masses corresponding to the bound lectin proteins, except RCA, whereby the lectin proteins were successfully identified.

As descried above, it was confirmed that proteins could be identified accurately by the protein analysis via SPR analysis and mass spectroscopy using the ligand conjugate according to the present invention. Moreover, the results of the present Example confirmed that the bonding activity between the sugar chains and proteins would be different even between ligand carries having identical sugar chains at their ends when there was a difference therebetween in terms of the number of the sugar chains present. That is, the protein analysis according to the present invention is deemed to be applicable to analysis on the relationship between the number of sugar chains and the bonding activity of the proteins. Any existing method cannot detect the relationship between the number of sugar chains and the bonding activity of the proteins. So, the present invention will be deemed to be more useful, when considering the analysis on the relationship between the number of sugar chains and the bonding activity of the proteins.

Example 3

Synthesis of Ligand Conjugates (Compounds 21 and 22)

In the present Example, ligand conjugates classified as fifth and sixth ligand conjugates explained in the embodiment were synthesized. That is, a ligand conjugate (Compound 21), which was a fifth ligand conjugate, was synthesized as below, the ligand conjugate having a structure represented by General Formula (13), where $n^2$ was 4, X had a structure represented by General Formula (4), R' was a hydrogen (H), and R was glucose. Further, a ligand conjugate (Compound 22), which was a sixth ligand conjugate, was synthesized as below, the ligand conjugate having a structure represented by General Formula (13), where $n^2$ was 4, X had a structure represented by General Formula (4), R' was a hydrogen (H), and R was maltose.

[Analysis Method, Reagents]

$^1$H-NMR spectroscopy was carried out with JEOL-Delta 600 Spectrometer. Chemical shift for CDCl$_3$ was indicated by δ value using tetramethylsilane (0.00 ppm) as reference material, while chemical shift for D$_2$O was indicated by δ value using DHO (4.65 ppm) as reference material. The mass spectroscopy was carried out using PerSeptive Biosystem Mariner™ Biospectroscopy Workstation. Silica gel column chromatography was carried out with Silicagel 60 (Merck, 0.040 to 0.063 mm). Thin layer chromatography was carried out using Precoated Silicagel 60 F254 (Merck, 0.5 mm). All reagents and anhydrous solvents were purchased from Kanto Chemical Co., Ltd.

(1) Synthesis of Compound 16

The synthesis of Compound 16 is described below referring to Formula (29):

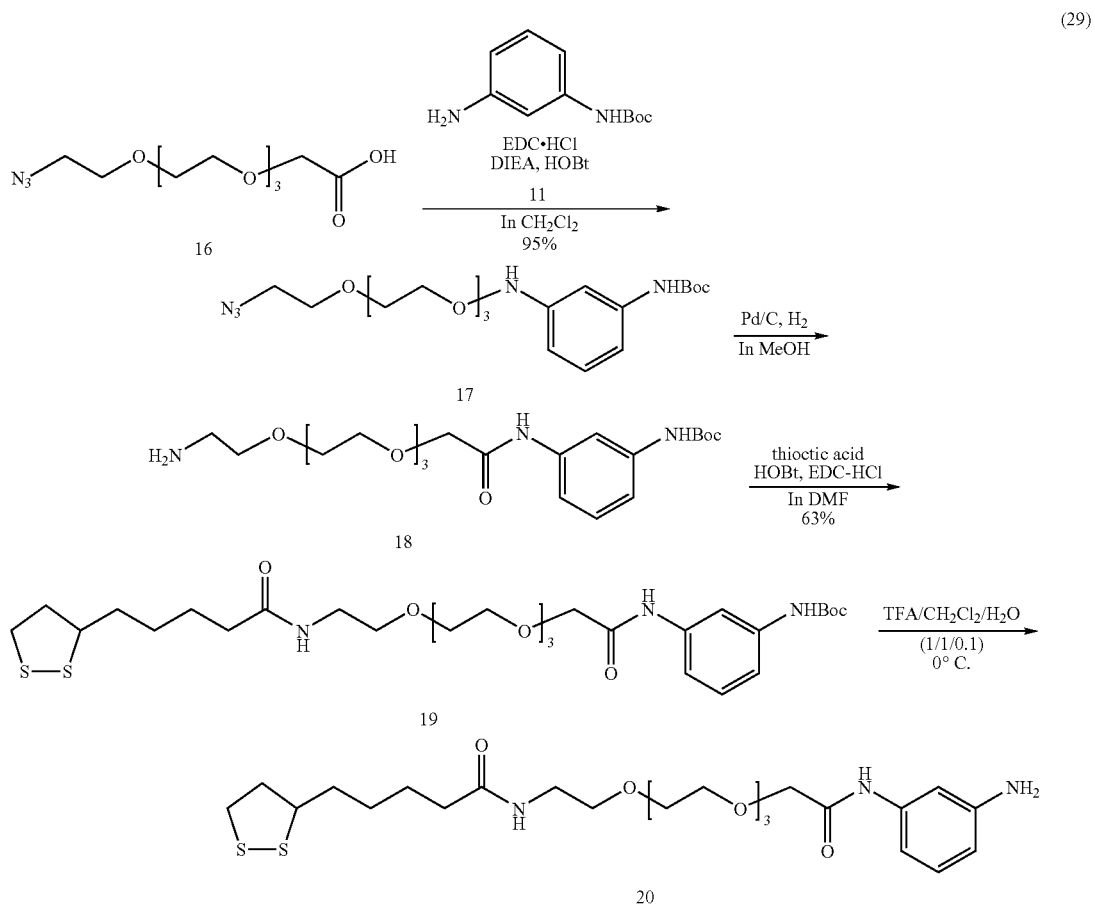

Firstly, Compound 16 of Formula (29) was synthesized as below.

Bis [2-(2-hydroxyethoxy)ethyl]ether (14.57 ml, 80 mmol) and BF$_3$.Et$_2$O (252 ml, 2 mmol) were dissolved in 50 ml of anhydrous dichloromethane. Then diazoethyl acetate (1.8 ml, 17.35 mmol) was dropped therein at 0° C. After that, the resultant was stirred for 70 minutes at room temperature. After 20 ml of saturated ammonium chloride aqueous solution was added into the reaction solution, the reaction solution was extracted with dichloromethane, and then dried with anhydrous magnesium sulfate. After the drying agent was filtered out, the filtrate was concentrated under reduced pressure thereby to obtain a concentrated residue. The concentrated residue was purified via chromatography (600 g, hexane:ethyl acetate=1:3), thereby obtaining ethyl compound (2.26 g, Yield: 47%) in the form of colorless liquid.

The ethyl compound (2.15 g, 7.66 mmol) and DMAP (41.7 mg, 337 mmol) were dissolved in 8 ml of anhydrous pyridine. Into the solution thus prepared, a solution in which p-toluene sulfonic chloride (1.75 g, 9.19 mmol) was dissolved in 8 ml of anhydrous dichloromethane was dropped at 0° C., and stirred for three hours at room temperature. Dichloromethane and ice water were added into the reaction solution, the reaction solution was extracted with dichloromethane. The organic layer thus obtained was washed with saturated sodium hydrogen carbonate aqueous solution, with water, and with saturated saline, once each. Then, the organic layer was dried with anhydrous magnesium sulfate. After the drying agent was filtered out, the filtrate was concentrated under reduced pressure, thereby to obtain concentrated residue. The concentrated residue was purified via chromatography (100 g, chloroform: acetone=4:1), thereby obtaining tosyl compound (2.59 g, Yield: 78%) in the form of yellow liquid.

The tosyl compound (1.01 g, 2.31 mmol) and sodium azide (1.53 g, 2.31 mmol) were dissolved in 50 ml of anhydrous dimethylformamide, and then stirred at 120° C. for 10 hours under nitrogen atmosphere in the dark. The reaction solution was extracted with chloroform. The organic layer thus obtained was washed with water and with saturated saline, once each, and then dried with anhydrous magnesium sulfate. After the drying agent was filtered out, the filtrate was concentrated under reduced pressure, thereby to obtain a concentrated residue. The concentrated residue was purified via chromatography (10 g, chloroform:acetone=2:1), thereby obtaining azide compound (638 mg, Yield: 90%) in the form of yellow liquid.

The azide compound (614 mg, 2.01 mmol) was dissolved in 24 ml of methanol. After 4.3 ml of 1N NaOH was added therein at 0° C. in the dark, the resultant solution was stirred at room temperature for 21 hours. The reaction solution thus obtained was concentrated under reduced pressure, thereby obtaining a concentrated residue. After chloroform was added to the concentrated residue, 1N HCl was added therein until pH 2 was obtained. Then, extraction with chloroform was carried out. The organic layer was washed once with saturated saline, and then dried with anhydrous magnesium sulfate. After the drying agent was filtered out, the filtrate was concentrated under reduced pressure, thereby obtaining Compound 16 (549 mg, Yield: 90%) in the form of colorless liquid.

$^1$H-NMR (400 MHz, CDCl$_3$) analysis of Compound 16 showed that δ6.19 (1H, bs, CO$_2$H), 4.16 (2H, s, OCH$_2$CO$_2$H), 3.75-3.64 (12H, m, OCH$_2$CH$_2$O), 3.68 (2H, m, N$_3$CH$_2$CH$_2$), 3.41 (2H, t, J=5.1 Hz, N$_3$CH$_2$). Moreover, ESI-MS (negative) analysis of Compound 6 showed that m/z was 328.14 [(M+Na)$^+$]. This confirmed the structure of Compound 6. In addition, Compound 16 was found to have a molecular mass of 277.13.

(2) Synthesis of Compound 17

Compound 16 (228 mg, 0.823 mmol) was dissolved in anhydrous dichloromethane (4 ml). Then, at room temperature, HOBt (135 mg, 0.987 mmol), EDC.HCl (192 mg, 0.987 mmol), and then at 0° C. Compound 11 (205 mg, 0.987 mmol) were added therein and then stirred for 20 hours in the dark. The reaction solution thus obtained was concentrated under reduced pressure thereby obtaining a concentrated residue. The concentrated residue was then extracted with chloroform. The organic layer thus obtained was washed with 10% citric acid, and with saturated sodium hydrogen carbonate aqueous solution, once each, and then dried with anhydrous magnesium sulfate acting as a drying agent. After the drying agent was filtered out, the filtrate was concentrated under reduced pressure, thereby obtaining a concentrated residue. The concentrated residue was purified via silica gel chromatography (80 g, chloroform:methanol=10:1), thereby obtaining Compound 17 (367 mg, Yield: 95%) in the form of yellow oily material. ESI-MS (positive) analysis of Compound 17 showed that m/z was 490.24 [(M+Na)$^+$]. This confirmed the structure of Compound 3. In addition, Compound 17 was found to have a molecular mass of 467.24.

(3) Synthesis of Compound 18

Compound 17 (29 mg, 0.062 mmol) was dissolved in methanol (3 ml). After 10% Pd/c (5.0 mg) was added therein, the solution thus obtained was stirred for 9 hours under hydrogen atmosphere. After Pd/C was filtered out, the filtrate was concentrated under reduced pressure, thereby obtaining a concentrated residue. The concentrated residue was purified via silica gel chromatography (1.5 g, chloroform:methanol=7:1), thereby obtaining Compound 18 (22 mg, Yield: 82%) in the form of yellow oily material. ESI-MS (positive) analysis of Compound 18 showed that m/z was 442.27 [(M+H)$^+$]. This confirmed the structure of Compound 18. In addition, Compound 18 was found to have a molecular mass of $C_{21}H_{35}N_3O_7$:441.25.

(4) Synthesis of Compound 19

Thioctic acid (12.6 mg, 0.061 mmol) was dissolved in anhydrous dimethylformamide (2 ml). Then, HOBt (8.3 mg, 0.061 mmol), and EDC.HCl (11.8 mg, 0.061 mmol) were sequentially added therein under argon atmosphere. After having brought the temperature back to room temperature, the solution thus obtained was stirred for 2 hours in the dark. Compound 18 (22.4 mg, 0.051 mmol) was dissolved in anhydrous dimethylformamide (2 ml), and then stirred for 1 day at room temperature in the dark. After toluene was added in the reaction solution, the reaction solution was concentrated. The organic layer thus obtained was washed sequentially with 10% citric acid, and then with saturated sodium hydrogen carbonate aqueous solution, and dried with anhydrous magnesium sulfate. After the drying agent was filtered out, the filtrate was concentrated under reduced pressure, thereby obtaining a concentrated residue. The concentrated residue was purified via silica gel column chromatography (3 g, chloroform:methanol=10:1), thereby obtaining Compound 19 in the form of yellow oil material. Yield was 27 mg (84%). ESI-MS (positive) analysis of Compound 19 showed that m/z was 652.28 [(M+Na)$^+$]. This confirmed the structure of Compound 19. In addition, Compound 19 was found to have a molecular mass of 629.28.

(5) Synthesis of Compound 20

Compound 19 (31 mg, 0.050 mmol) was dissolved in dichloromethane (2 ml). At a temperature of 0° C., TFA (147 μl) was added and stirred for 3 hours at this temperature. After being concentrated, the reaction solution was azeotropically boiled with toluene, thereby obtaining a concentrated residue. The concentrated residue was dissolved in dichloromethane. After triethylamine aqueous solution was added therein thereby to adjust the water phase to pH 8, the organic phase was dried with anhydrous magnesium sulfate. After the drying agent was filtered out, the filtrate was concentrated under reduced pressure. The concentrated residue thus obtained was purified via silica gel column chromatography (10 g, chloroform:methanol=5:1), thereby obtaining Compound 20 in the form of yellow oily material. Yield was 26.1 mg (59%). $^1$H-NMR spectroscopy (600 MHz, CDCl$_3$) analysis of Compound 20 showed that δ7.17 (s, 1H, aromatic), 7.1 (dd, 1H, J=8.6, 8.3 Hz aromatic), 6.91 (d, 1H, J=8.2 Hz aromatic) 6.45 (d, 1H, J=8.2 Hz aromatic) 4.1 (s, 2H, —OCH$_2$CONH—), 3.78-3.49 (m, 15H, ethylene glycol chain, CH$_2$CH(CH$_2$—)(S—)), 3.41 (q, 2H, J=5.5 Hz, —CONHCH$_2$CH$_2$O—), 3.16 (m, 1H, —SCH$_2$(1H)—), 3.08 (m, 1H, —SCH$_2$(1H)—), 2.46-2.44 (m, 1H, —SCH$_2$CH$_2$(1H)—), 2.13-2.10 (t, 2H, J=7.6 Hz, —NHCOCH$_2$CH$_2$—), 1.92-1.88 (m, 1H, —SCH$_2$CH$_2$(1H)—), 1.43-1.40 (m 4H, —COCH$_2$CH$_2$CH$_2$—), 1.26-1.24 (m, 2H, —COCH$_2$CH$_2$CH$_2$CH$_2$—). ESI-MS (positive) analysis of Compound 20 showed that m/z was 552.31 [(M+Na)$^+$]. From this, the structure of Compound 20 was confirmed. In addition, Compound 20 was found to have a molecular mass of 529.23.

(6) Synthesis of Ligand Conjugate (Compound 21)

The synthesis of a ligand conjugate (compound 21) is explained below referring to Formula (30):

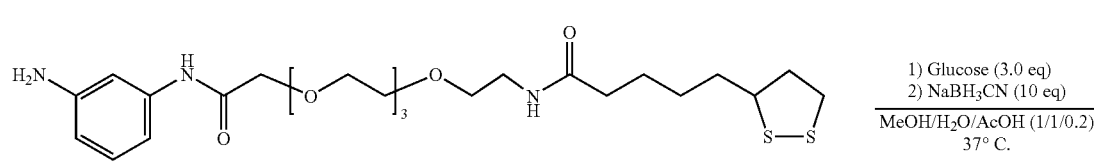

(30)

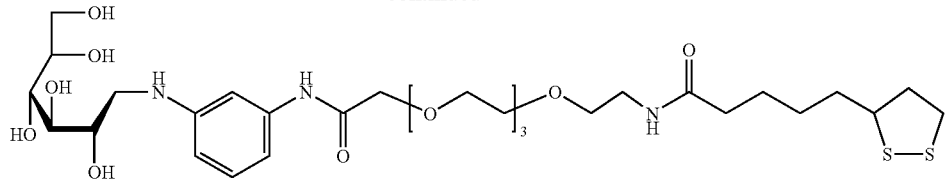

21

Compound 20 (15.5 mg, 29.3 μmol) and glucose (5.8 mg, 32.2 μmol) were dissolved in DMAc/water (1:1, 1 ml). After acetic acid (200 μl) was added therein, the reaction solution thus obtained was allowed to stand for 2 days at 37° C. After that, sodium cyanoborohydride (5.5 mg, 87.9 μmol) was added therein, the reaction solution was allowed to stand for another 6 days at 37° C. Then, the reaction solution was concentrated thereby obtaining a residue. The residue was purified via ODS column chromatography (Chromatorex ODS, 30 g, methanol/water=50/50). Thereby, Compound 21 was obtained in the form of white solid with a yield of 4.54 mg (22%).

$^1$H-NMR spectroscopy (600 MHz, D$_2$O) analysis of Compound 21 showed that δ 7.17 (s, 1H, aromatic), 7.1 (dd, 1H, J=8.6, 8.3 Hz aromatic), 6.91 (d, 1H, J=8.2 Hz aromatic) 6.45 (d, 1H, J=8.2 Hz aromatic) 4.1 (s, 2H, —OC$\underline{H}_2$CONH—), 3.80-3.76 (m, 1H, H-2), 3.68-3.35 (m, 19H, ethylene glycol chain, H-3, H-6a, H-5, H-4, H-6b), 3.20-3.10 (m, 2H, H-1-a, C$\underline{H}_2$CH(CH$_2$—)(S—)), 3.05-2.94 (m,1H,H-1b, —SC$\underline{H}_2$), 2.28-2.23 (m, 1H, —SCH$_2$C$\underline{H}_2$(1H)—), 2.13-2.10 (t, 2H, J=7.6, 6.9 Hz, —NHCOC$\underline{H}_2$CH$_2$—), 1.78-1.69 (m, 1H, —SCH$_2$C$\underline{H}_2$(1H)—), 1.53-1.36 (m 4H, —COCH$_2$C$\underline{H}_2$CH$_2$C$\underline{H}_2$—), 1.20-1.10 (m, 2H, —COCH$_2$CH$_2$C$\underline{H}_2$CH$_2$—). MALDI-TOF-MS analysis of Compound 21 showed that m/z 694.66 was [(M+H)$^+$]. These confirmed the structure of Compound 21. In addition, Compound 21 was found to have a molecular mass of 693.30.

(7) Synthesis of Ligand Conjugate (Compound 22)

The synthesis of a ligand conjugate (compound 22) is explained below referring to Formula (31):

Then, the reaction solution was allowed to stand for another 120 hours at 37° C. Then, the reaction solution was concentrated. The residue thus obtained as purified via ODS column chromatography (Chromatorex ODS, 30 g, methanol/water=50/50). Thereby, Compound 22 was obtained in the form of white solid with a yield of 2.36 mg (16%).

$^1$H-NMR spectroscopy (600 MHz, D$_2$O) analysis of Compound 22 showed that δ7.07-7.04 (t, 1H, J=8.2, Hz, aromatic), 6.76 (s, 1H, aromatic), 6.63 (d, 1H, J=8.2 Hz, aromatic), 6.48 (dd, 1H, J=2.1, 6.2 Hz, aromatic), 4.91 (d, 1H, J=4.1 Hz, H-1), 4.1 (s, 2H, —OC$\underline{H}_2$CONH—), 3.82-3.78 (m, 1H, H-2),3.75-3.34(m,24H, ethylene glycol chain H-2', H-5', H-5, H-6'a, H-6' b, H-6a, H-6b, H-3, H-3', H-4') 3.25 (m, 1H, CH$_2$C$\underline{H}$(CH$_2$—)(S—)),3.18-3.11(m, 3H, H1'b, —CONH C$\underline{H}_2$CH$_2$O—),3.07-2.93(m, 3H, H1'a, —SC$\underline{H}_2$),2.29-2.20 (m, 1H, —SCH$_2$C$\underline{H}_2$(1H)—), 2.05-1.96 (t, 2H, J=7.6, 6.9 Hz, —NHCOC$\underline{H}_2$CH$_2$—), 1.76-1.69 (m, 1H, —SCH$_2$CH$_2$(1H)—), 1.52-1.31 (m 4H, —COCH$_2$C$\underline{H}_2$CH$_2$C$\underline{H}_2$—), 1.18-1.10 (m, 2H, —COCH$_2$CH$_2$C$\underline{H}_2$CH$_2$—). MALDI-TOF-MS analysis of Compound 22 showed that m/z was 878.39 [(M+Na)$^+$]. These confirmed the structure of Compound 22. In addition, Compound 22 was found to have a molecular mass of 855.35.

Example 4

Synthesis of Ligand Conjugates (Compounds 26 and 27)

In the present Example, ligand conjugates classified as seventh and eighth ligand conjugates explained in the

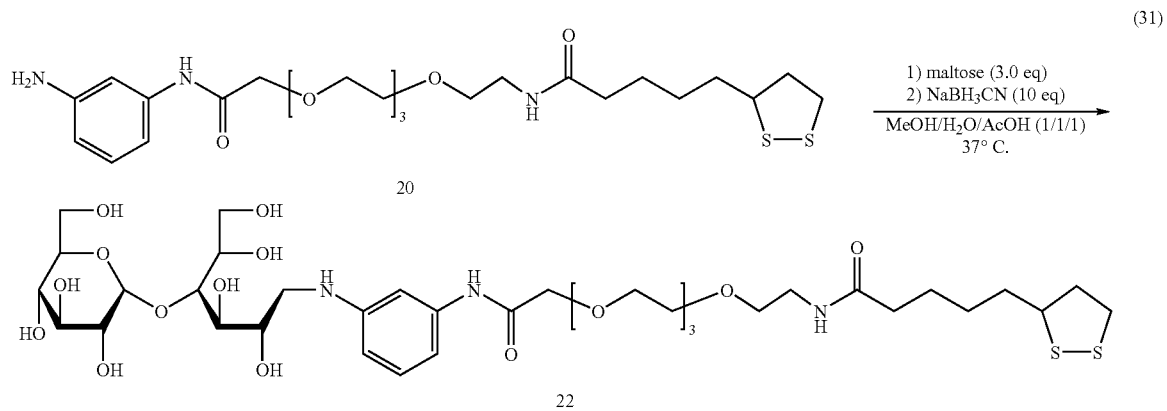

Compound 20 (9.0 mg, 17.0 μmol) and maltose (5.8 mg, 17.0 μmol) were dissolved in methanol/water (1:1, 1 ml). After acetic acid (50 μl) was added therein, the solution thus obtained was allowed to stand for 24 hours at 37° C. Into the reaction solution thus obtained, acetic acid (450 μl) and sodium cyanoborohydride (3.2 mg, 51.0 μmol) were added.

embodiment were synthesized. That is, a ligand conjugate (Compound 26), which was a seventh ligand conjugate, a fifth ligand conjugate, was synthesized as below, the ligand conjugate having a structure represented by General Formula (14), where n$^1$ was 3, X had a structure represented by General Formula (4), R' was a hydrogen (H), and R was glucose.

Further, a ligand conjugate (Compound 26), which was an eighth ligand conjugate, was synthesized as below, the ligand conjugate having a structure represented by General Formula (14), where $n^1$ was 3, X had a structure represented by General Formula (4), R' was a hydrogen (H), and R was maltose.

Note that the analysis method, reagents, etc. are same as in Example 3.

(1) Synthesis of Compound 24

The synthesis of Compound 24 is described below referring to Formula (32):

Na)$^+$]. This confirmed the structure of Compound 24. In addition, Compound 24 was found to have a molecular mass of 618.25.

(2) Synthesis of Compound 25

Compound 24 (103 mg, 11.67 mmol) was dissolved in dichloromethane (2 ml). Then, TFA (247 µl) was added therein at 0° C., and then stirred for 1 hour at this temperature. After being concentrated, the reaction solution thus obtained was azeotropically boiled with toluene. The concentrated residue thus obtained was dissolved in ethyl acetate. After the

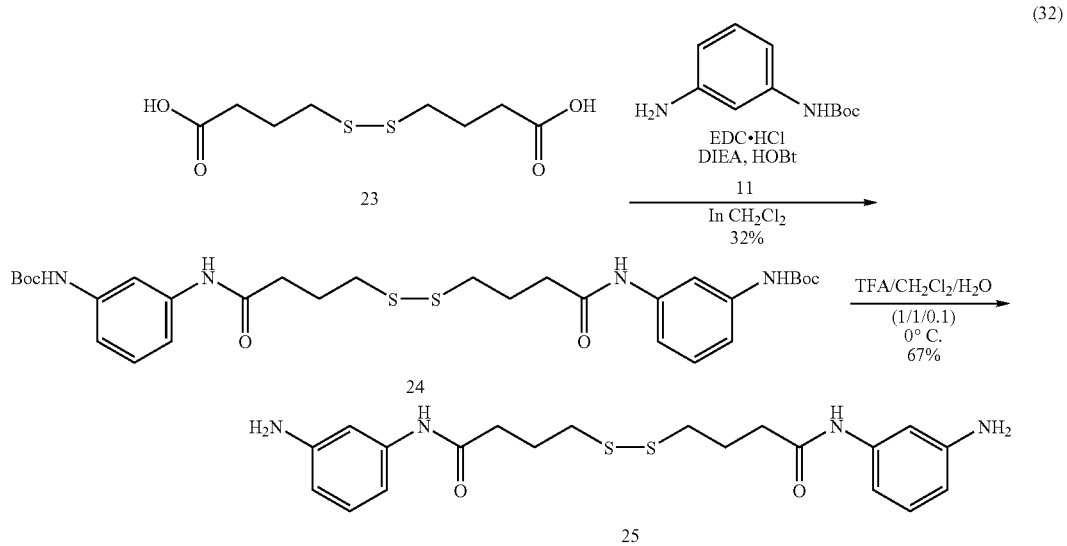

(32)

A dimer of γ-mercapto lactate (Compound 23) (344 mg, 1.44 mmol) was dissolved in anhydrous dichloromethane (25 ml). Then, HOBt (359 mg, 2.64 mmol), EDC.HCl (508 mg, 2.64 mmol), N-Boc-phenylene diamine (Compound 11) (502 mg, 2.4 mmol) were sequentially added therein at room temperature under argon atmosphere, and then stirred for 17 hours in the dark. The reaction solution thus obtained was concentrated under reduced pressure thereby obtaining a concentrated residue. The concentrated residue was extracted with chloroform. The organic layer thus obtain was washed once with 10% citric acid, and with saturated sodium hydrogen carbonate aqueous solution, and then dried with anhydrous magnesium sulfate. After the drying agent was filtered out, the filtrate was concentrated under reduced pressure, thereby obtaining a concentrated residue. The concentrated residue was purified via silica gel chromatography (50 g, toluene:ethyl acetate=5:1), thereby obtaining Compound 24 (220 mg, Yield: 30%) in the form of yellow oily material. ESI-MS of Compound 24 showed that m/z was 641.25 [(M+ water phase was adjusted to pH 8 by adding triethylamine aqueous solution, the organic phase was dried with anhydrous magnesium sulfate. After the drying agent was filtered off, the organic layer was concentrated under reduced pressure, thereby obtaining a concentrated residue. The concentrated residue was purified via silica gel column chromatography (5 mg, chloroform:acetone=5:1) thereby obtaining Compound 25 in the form of yellow oily material. Yield was 46.8 mg (67%). $^1$H-NMR spectroscopy (600 MHz, CDCl$_3$) analysis of Compound 25 showed that δ 6.93-6.89 (m, 2H, aromaric), 6.71-6.68 (d, 1H, J=8.4 Hz, aromaric), 6.37-6.35 (d, 1H, J=8.4 Hz, aromaric), 2.66 (t, 2H, J=6.6 Hz, O=C—C$\underline{H}_2$), 2.36 (t, 2H, J=7.2 Hz, C$\underline{H}_2$—S), 1.98-1.94 (m, 2H, J=6.6 Hz, 14.4 Hz, CH$_2$C$\underline{H}_2$CH$_2$). ESI-MS (positive) of Compound 25 showed that m/z was 419.06 [(M+H)$^+$]. From this, the structure of Compound 25 was confirmed. In addition, Compound 25 was found to have a molecular mass of 418.15.

(3) Synthesis of Ligand Conjugate (Compound 26)

The synthesis of a ligand conjugate (Compound 26) is described below referring to Formula (33):

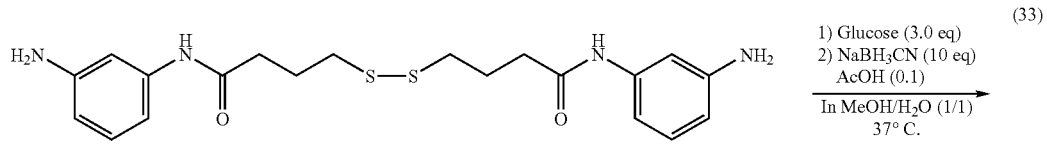

(33)

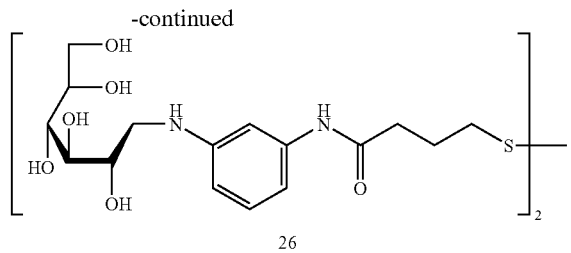

26

Compound 25 (5.04 mg, 12 μmol) and glucose (4.79 mg, 26 μmol) were dissolved in methanol/water (1:1, 1 ml). After acetic acid (50 μl) was added therein, the solution thus obtained was allowed to stand for 4 hours at 37° C. After acetic acid (950 μl), methanol/water (1:1, 1 ml), sodium cyanoborohydride (5.14 mg, 72 μmol) were added therein, the solution was allowed to stand for another 72 hours at 37° C. Then, the reaction solution thus obtained was concentrated, thereby obtaining a residue. The residue was purified via column chromatography (50 g, methanol/water=50/50) using LH-20. Thereby, Compound 26 was obtained in the form of white solid with a yield of 2.58 mg (29%).

$^1$H-NMR spectroscopy (600 MHz, $D_2O$) test of Compound 26 showed that δ 6.94 (t, 1H, J=7.8 Hz, aromaric), 6.66 (s, 1H, aromaric), 6.55 (d, 1H, J=8.4 Hz, aromaric), 6.37 (d, 1H, J=9.6 Hz, aromaric), 3.714-3.707 (m, 1H, J=4.2 Hz), 3.58-3.51 (m, 3H), 3.44-3.37 (m, 2H,), 3.10-3.07 (m, 2H, J=8.4 Hz, 13.8 Hz), 2.56-2.50 (m, 2H, O=C—C$\underline{H}_2$), 2.24 (t, 2H, J=3.6 Hz, C$\underline{H}_2$—S), 1.83-1.81 (m, 2H, CH$_2$C$\underline{H}_2$CH$_2$). MALDI-TOF-MS analysis of Compound 26 showed that m/z was 747.21[(M+H)$^+$]. These confirmed the structure of Compound 26. In addition, Compound 26 was found to have a molecular mass of 746.29.

(4) Synthesis of Ligand Conjugate (Compound 27)

The synthesis of a ligand conjugate (Compound 27) is described below referring to Formula (34):

Compound 25 (5.1 mg, 12 μmol) and maltose (9.2 mg, 26 μmol) were dissolved in methanol/water (1:1, 1 ml). After acetic acid (50 μl) was added therein, the solution thus obtained was allowed to stand for 4 hours at 37° C. After acetic acid (950 μl), methanol/water (1:1, 1 ml), sodium cyanoborohydride (5.22 mg, 72 μmol) were added therein, the solution was allowed to stand for another 120 hours at 37° C. Then, the reaction solution thus obtained was concentrated, thereby obtaining a residue. The residue was purified via column chromatography (50 g, methanol/water=50/50) using LH-20. Thereby, Compound 27 was obtained in the form of white solid with a yield of 2.74 mg (21%).

$^1$H-NMR spectroscopy (600 MHz, $D_2O$) test of Compound 26 showed that δ7.04 (t, 1H, J=4.2 Hz, aromaric), 6.77 (s, 1H, aromaric), 6.64 (d, 1H, J=7.8 Hz, aromaric), 6.54 (d, 1H, J=8.4 Hz, aromaric), 4.93 (d, 1H, J=3.6 Hz), 3.82-3.78 (m, 2H), 3.75-3.70 (m, 3H), 3.63-3.56 (m, 3H), 3.48 (dd, 1H, J=6.6 Hz, 11.4 Hz), 3.41-3.39 (m, 1H) 3.27 (t, 1H, J=9.0 Hz), 3.18 (s, 3H), 3.08-3.06 (m, 1H), 2.65 (t, 2H, 4.8 Hz, O=C—C$\underline{H}_2$), 2.34 (t, 2H, J=7.2 Hz, C$\underline{H}_2$—S), 1.91 (t, 2H, J=7.2 Hz, CH$_2$C$\underline{H}_2$CH$_2$). MALDI-TOF-MS analysis of Compound 27 showed that m/z was 1093.27 [(M+Na)$^+$]. These confirmed the structure of Compound 27. In addition, Compound 27 was found to have a molecular mass of 1070.39.

Example 5

Ligand conjugates were synthesized, which had a structure represented by General Formula (9) where n$^1$ and q were 0, and contained sugar chains shown in group (20) respectively. The analysis method, reagents, etc. are the same as in Example 4.

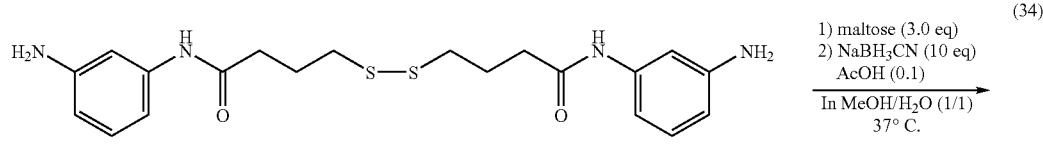

25

(34)

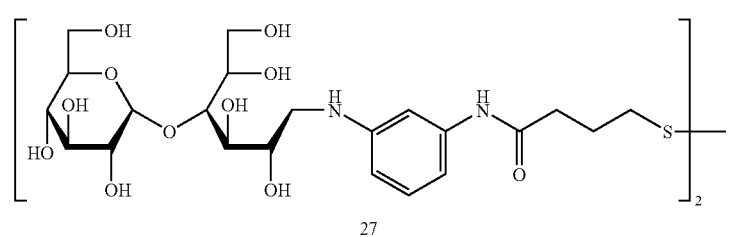

27

(1) Synthesis of Ligand Conjugate (Compound 30)

The procedure of synthesis of a ligand conjugate (Compound 30) is described below referring to Formula (35):

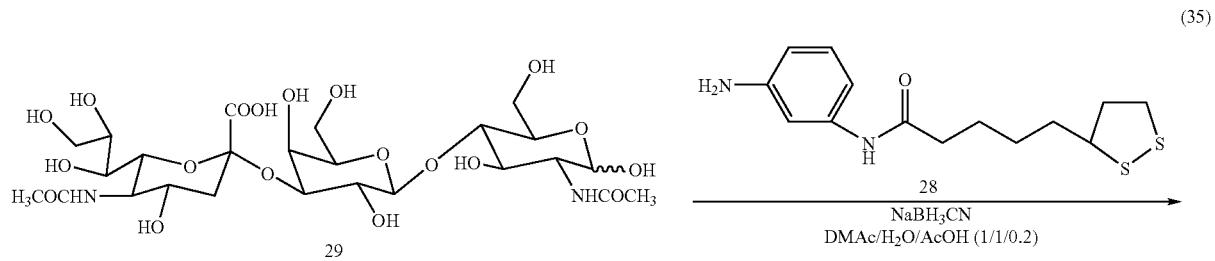

(35)

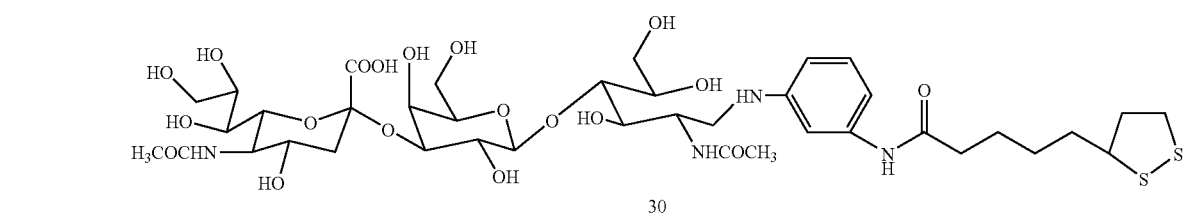

Compound 28 (2.47 mg, 8.24 μmol) and sialic acid-containing trisugar (Compound 29, 5.11 mg, 7.57 μmol) were dissolved in dimethylacetoamide/water (1:1, 1.0 ml). After acetic acid (100 μl) was added therein, the solution thus obtained was allowed to stand for 10 hours at 37° C. After sodium cyanoborohydride (1.55 mg, 24.7 mol) was added therein, the reaction solution thus obtained was allowed to stand for another 72 hours at 37° C. After the reaction solution was mixed with 3 ml of acetone and quenched for unreacted sodium cyanoborohydride, the reaction solution was concentrated. The thus obtained residue was purified by sequentially performing (1) column chromatography using Chromtorex ODS, (2) HPCL (column: DAISO SP-120-5-ODS-BP), and (3) chromatography using Sephadex G-25. Thereby, Compound 30 was obtained in the form of white solid with a yield of 2.31 mg (32%).

Figure 7:
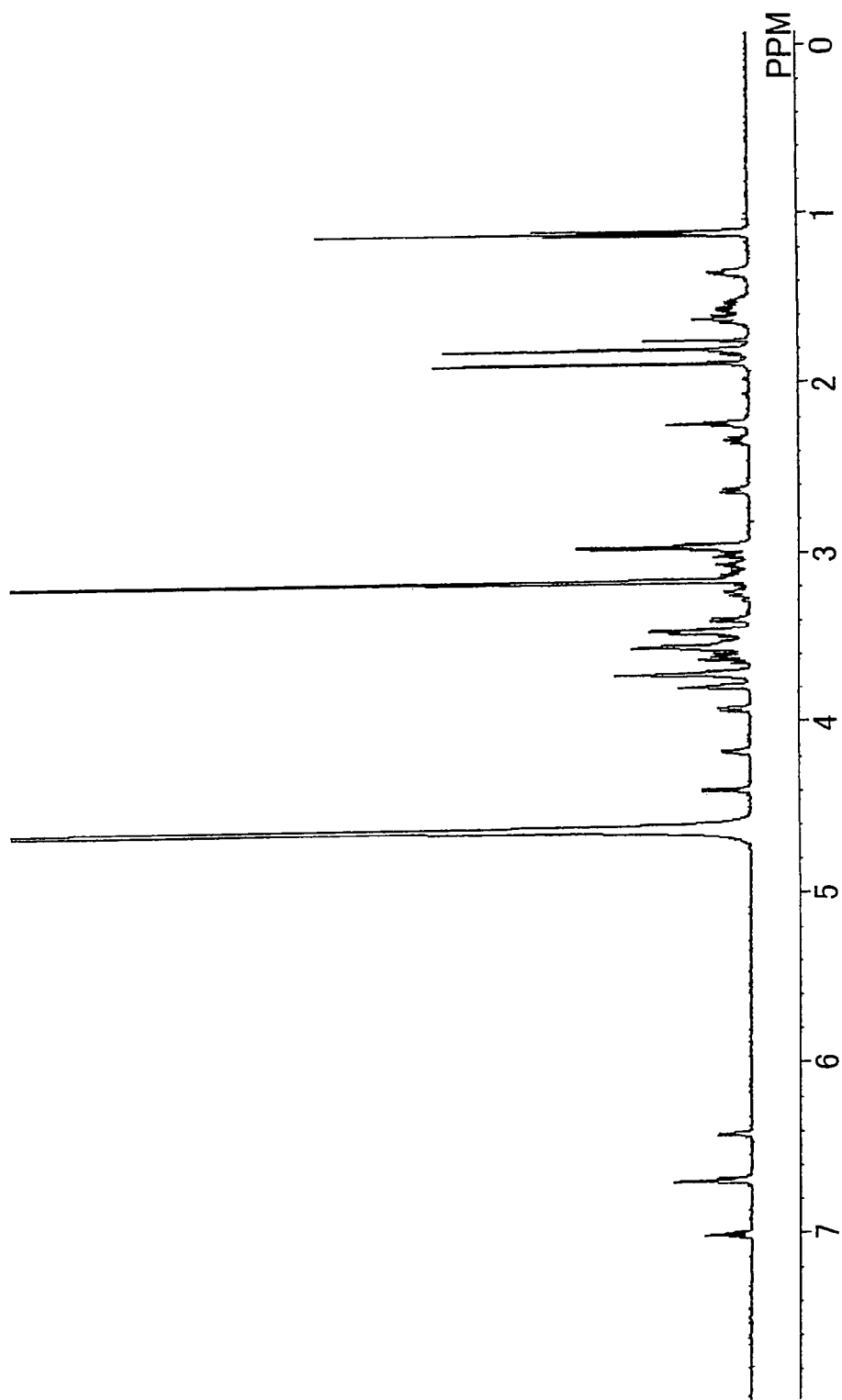
FIG. 7 is a chart of $^1$H-NMR spectroscopy analysis of a ligand conjugate (Compound 30).

$^1$H-NMR spectroscopy (600 MHz, $D_2O$) analysis of Compound 30 was conducted, thereby obtaining the chart in FIG. 7. MALDI-TOF-MS analysis of Compound 30 showed that m/z was 977.5 [(M+Na)$^+$]. This confirmed the structure of Compound 30. In addition, Compound 30 was found to have a molecular mass of 954.34.

(2) Synthesis of Ligand Conjugate (Formula (36))

The ligand conjugate shown in Formula (36) was synthesized in the same manner as in (1).

Figure 8:
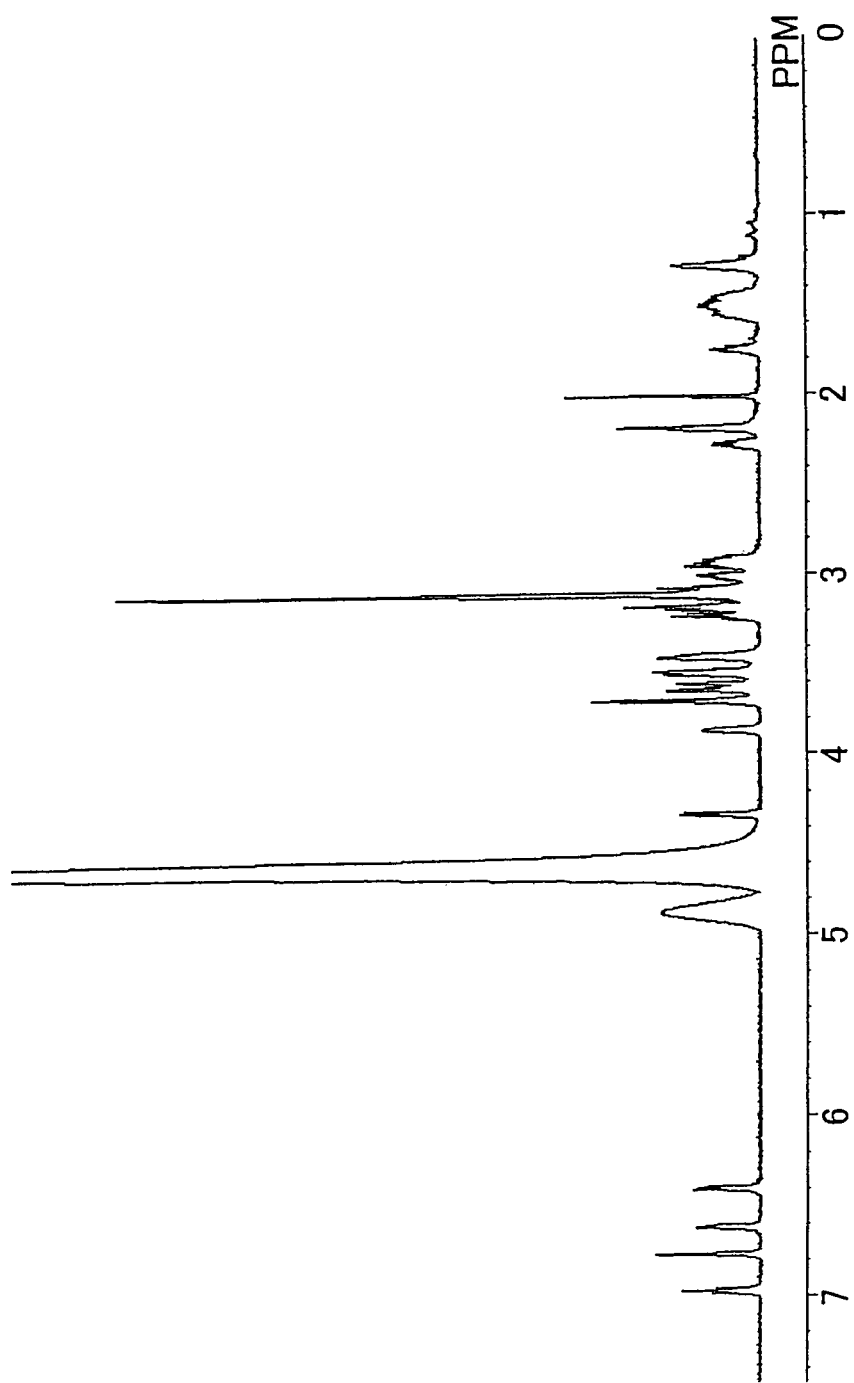
FIG. 8 is a chart of $^1$H-NMR spectroscopy analysis of a ligand conjugate (Formula (36)).

$^1$H-NMR spectroscopy of the ligand conjugate was conducted, thereby obtaining the chart shown in FIG. 8. This confirmed the structure of the ligand conjugate shown in Formula (36).

(3) Synthesis of Ligand Conjugate (Formula (37))

The ligand conjugate shown in Formula (37) was synthesized in the same manner as in (1).

Figure 9:
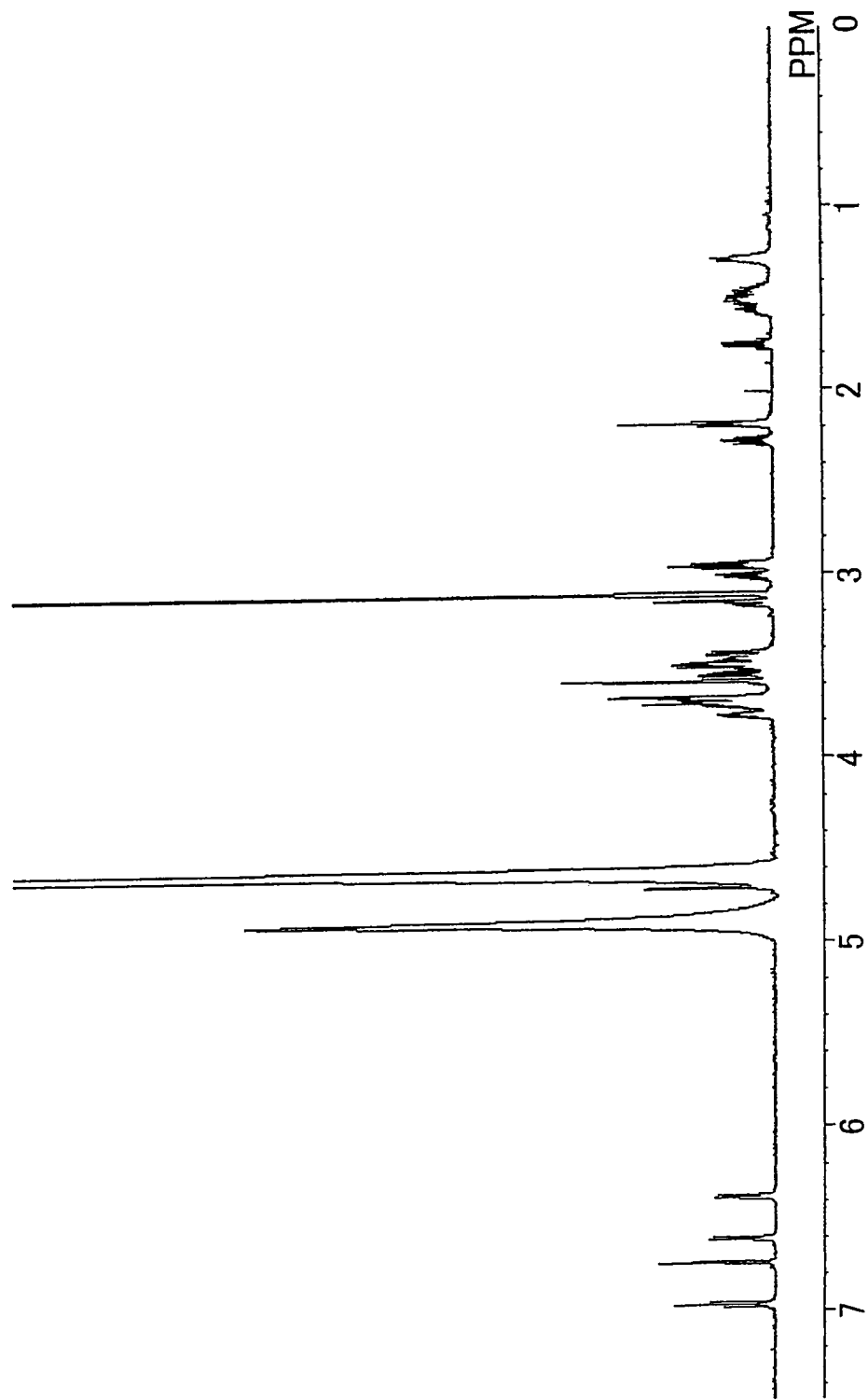
FIG. 9 is a chart of $^1$H-NMR spectroscopy analysis of a ligand conjugate (Formula (37)).

$^1$H-NMR spectroscopy of the ligand conjugate was conducted, thereby obtaining the chart shown in FIG. 9. This confirmed the structure of the ligand conjugate shown in Formula (37):

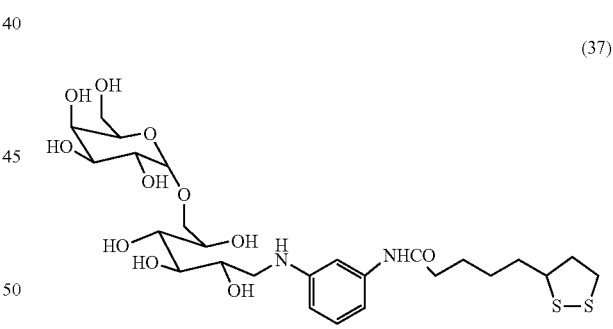

(37)

(4) Synthesis of Ligand Conjugate (Formula (38))

The ligand conjugate shown in Formula (38) was synthesized in the same manner as in (1).

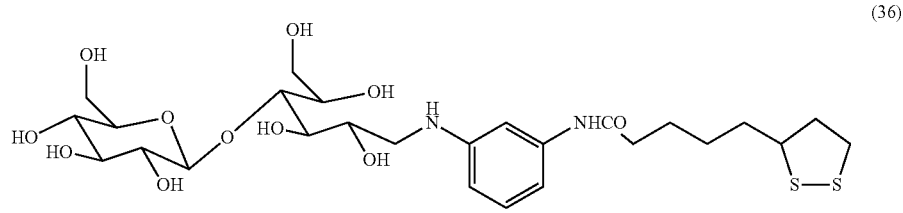

(36)

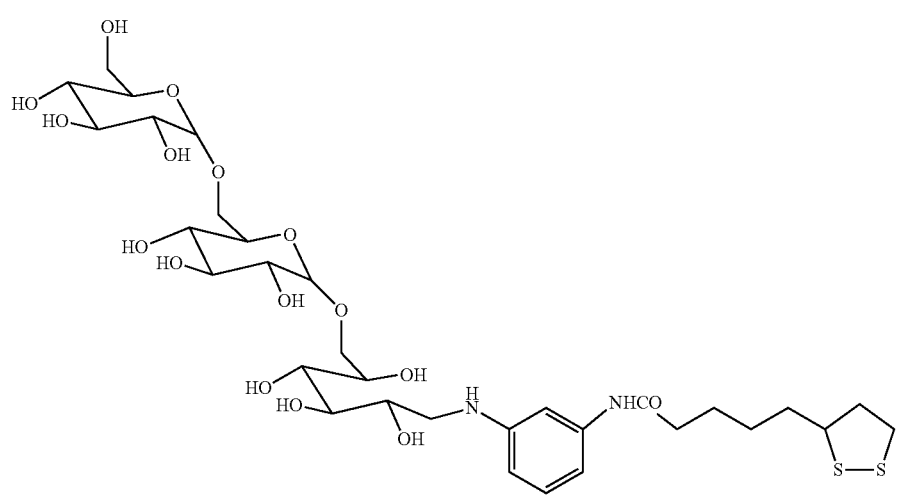

(38)

Figure 10:
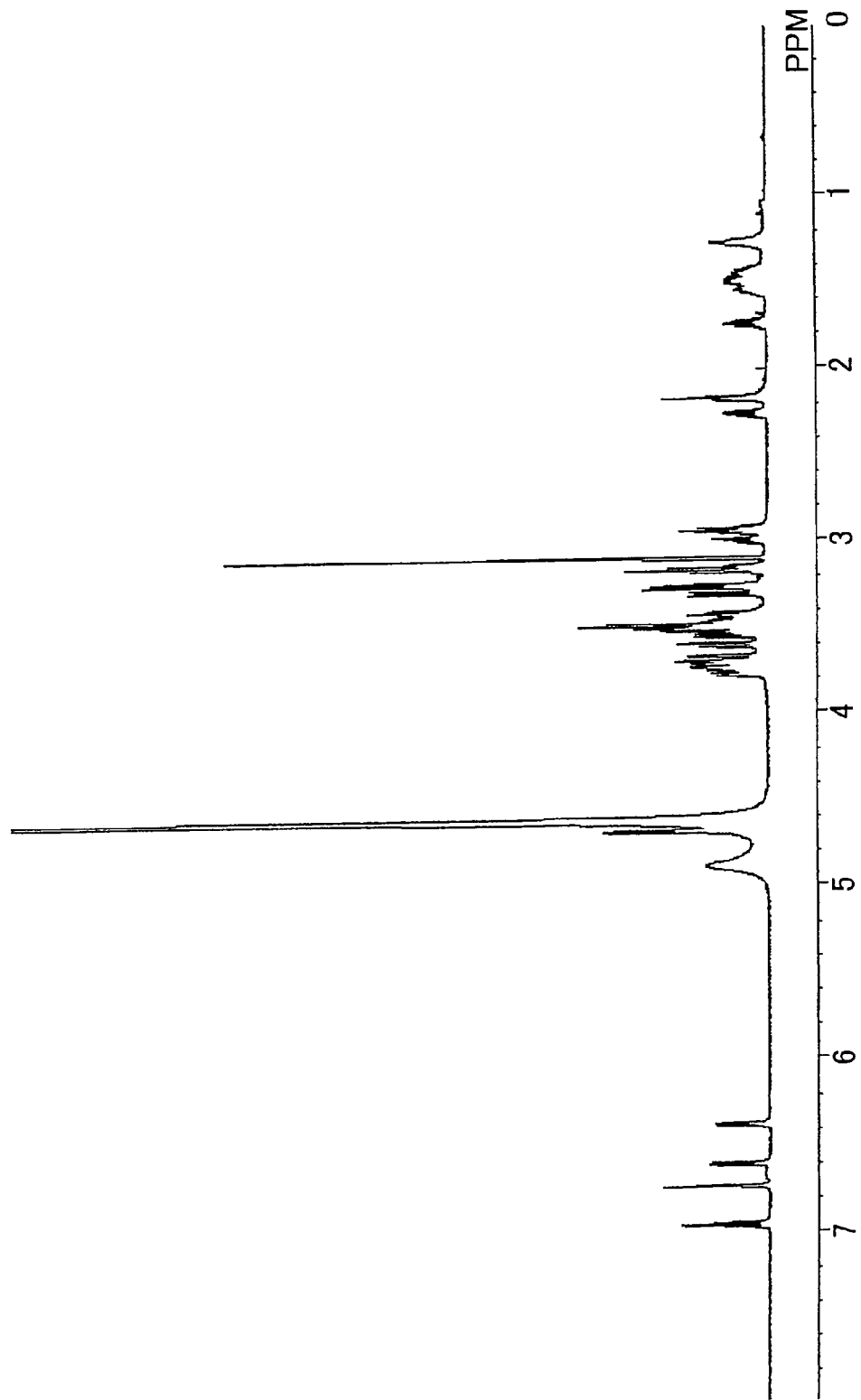
FIG. 10 is a chart of $^1$H-NMR spectroscopy analysis of a ligand conjugate (Formula (38)).

¹H-NMR spectroscopy of the ligand conjugate was conducted, thereby obtaining the chart shown in FIG. 10. This confirmed the structure of the ligand conjugate shown in Formula (38).

(5) Synthesis of Ligand Conjugate (Formula (39))

The ligand conjugate shown in Formula (39) was synthesized in the same manner as in (1).

Figure 11:
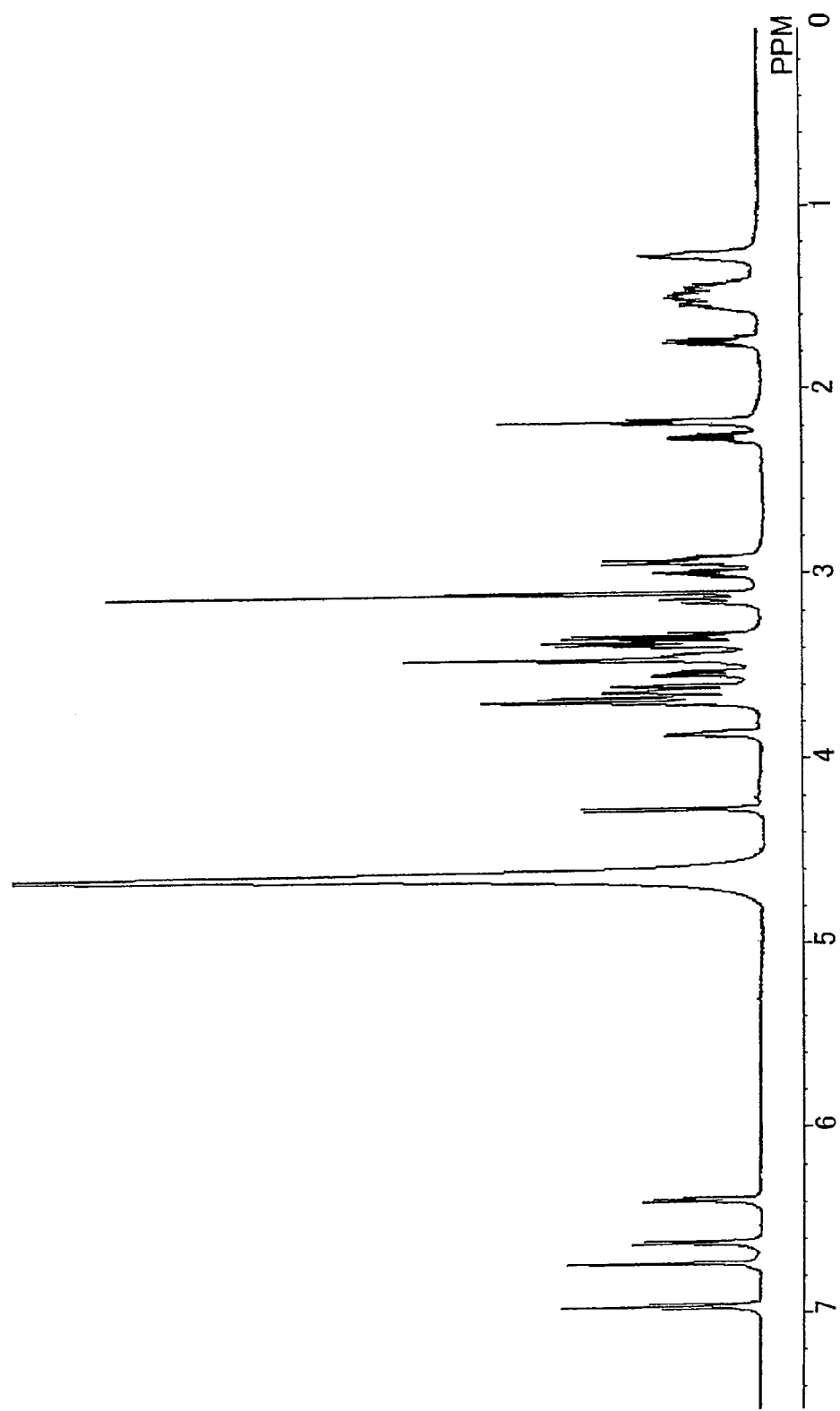
FIG. 11 is a chart of $^1$H-NMR spectroscopy analysis of a ligand conjugate (Formula (39)).

¹H-NMR spectroscopy of the ligand conjugate was conducted, thereby obtaining the chart shown in FIG. 11. This confirmed the structure of the ligand conjugate shown in Formula (39):

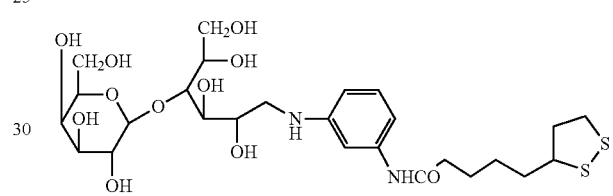

(39)

(6) Synthesis of Ligand Conjugate (Formula (40))

The ligand conjugate shown in Formula (40) was synthesized in the same manner as in (1).

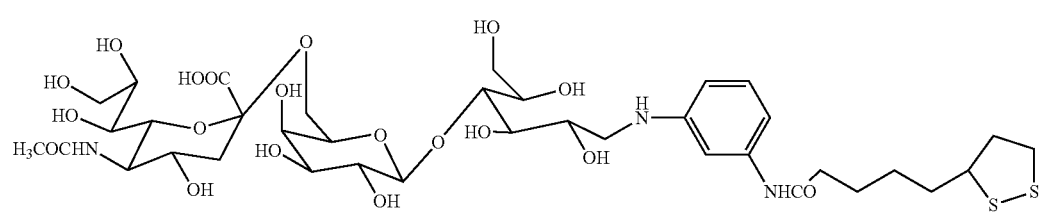

(40)

Figure 12:
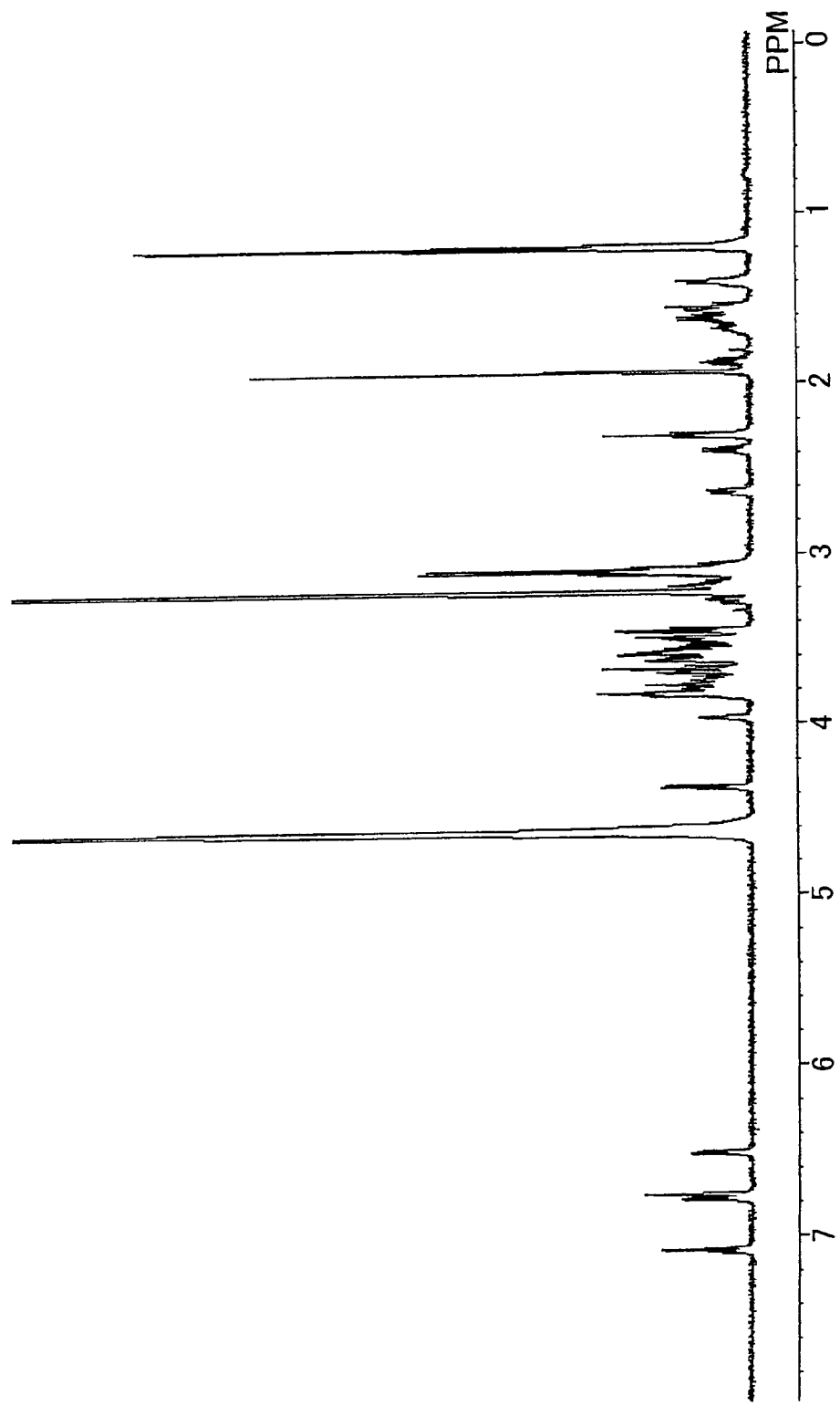
FIG. 12 is a chart of $^1$H-NMR spectroscopy analysis of a ligand conjugate (Formula (40)).

¹H-NMR spectroscopy of the ligand conjugate was conducted, thereby obtaining the chart shown in FIG. 12. This confirmed the structure of the ligand conjugate shown in Formula (40).

(7) Synthesis of Ligand Conjugate (Formula (41))

The ligand conjugate shown in Formula (41) was synthesized in the same manner as in (1).

Figure 13:
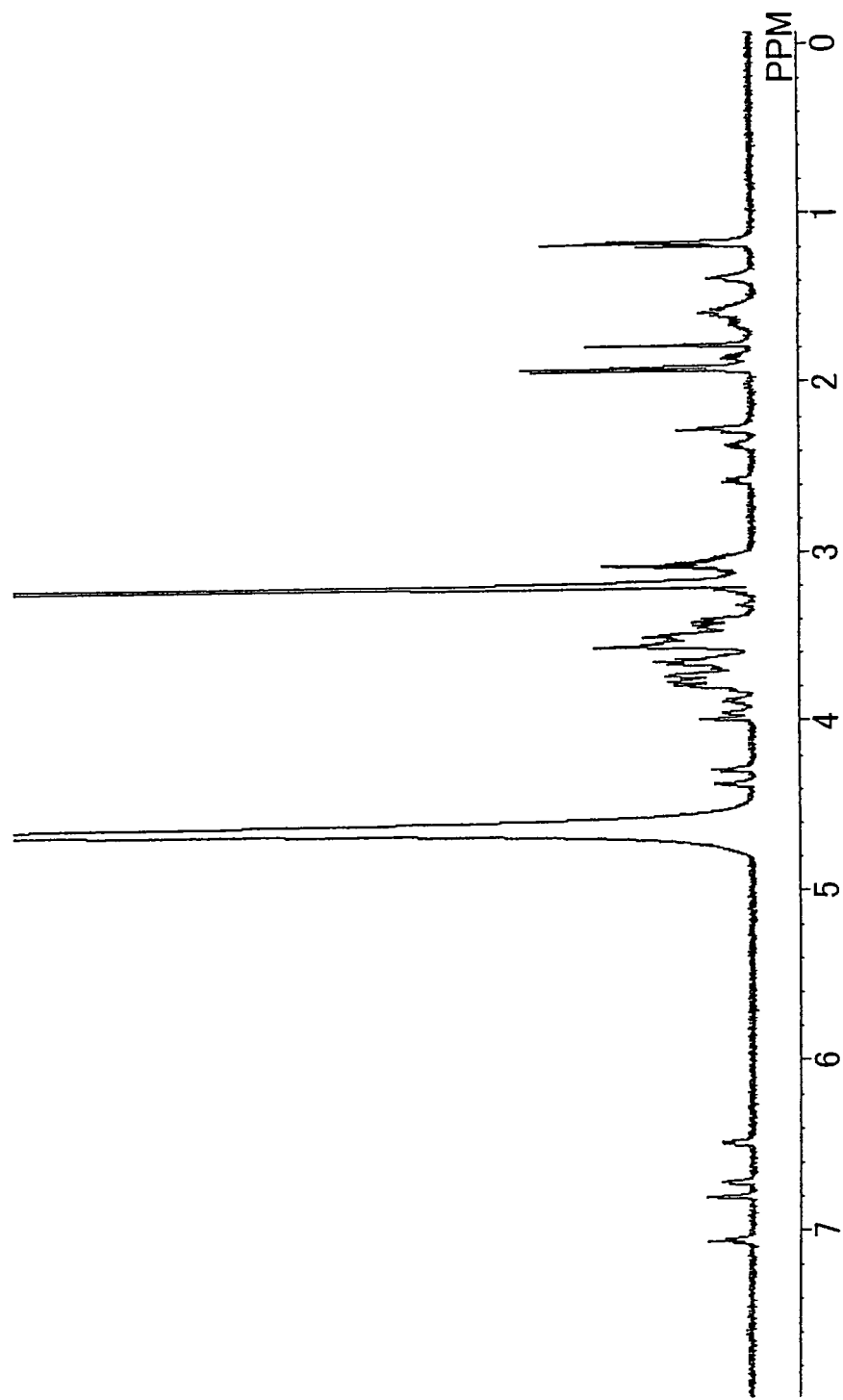
FIG. 13 is a chart of $^1$H-NMR spectroscopy analysis of a ligand conjugate (Formula (41)).

¹H-NMR spectroscopy of the ligand conjugate was conducted, thereby obtaining the chart shown in FIG. 13. This confirmed the structure of the ligand conjugate shown in Formula (41):

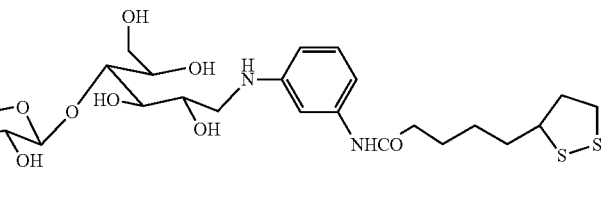

(41)

(8) Synthesis of Ligand Conjugate (Formula (42))

The ligand conjugate shown in Formula (42) was synthesized in the same manner as in (1).

Figure 14:
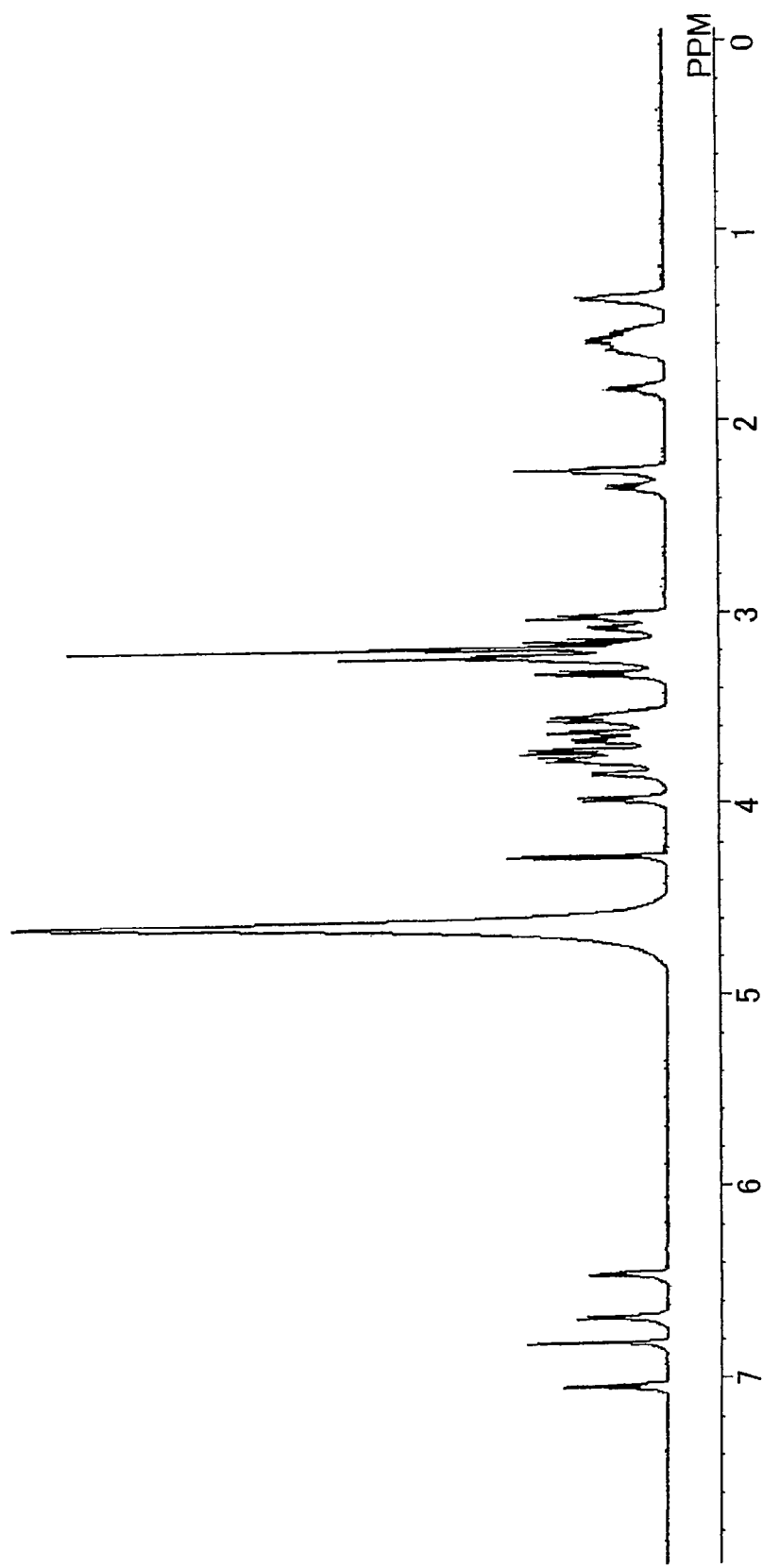
FIG. 14 is a chart of $^1$H-NMR spectroscopy analysis of a ligand conjugate (Formula (42)).

$^1$H-NMR spectroscopy of the ligand conjugate was conducted, thereby obtaining the chart shown in FIG. 14. This confirmed the structure of the ligand conjugate shown in Formula (42):

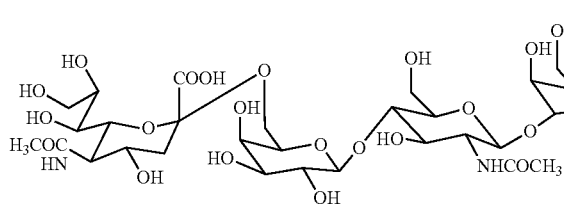

(42)

(9) Synthesis of Ligand Conjugate (Formula (43))

The ligand conjugate shown in Formula (43) was synthesized in the same manner as in (1).

Figure 15:
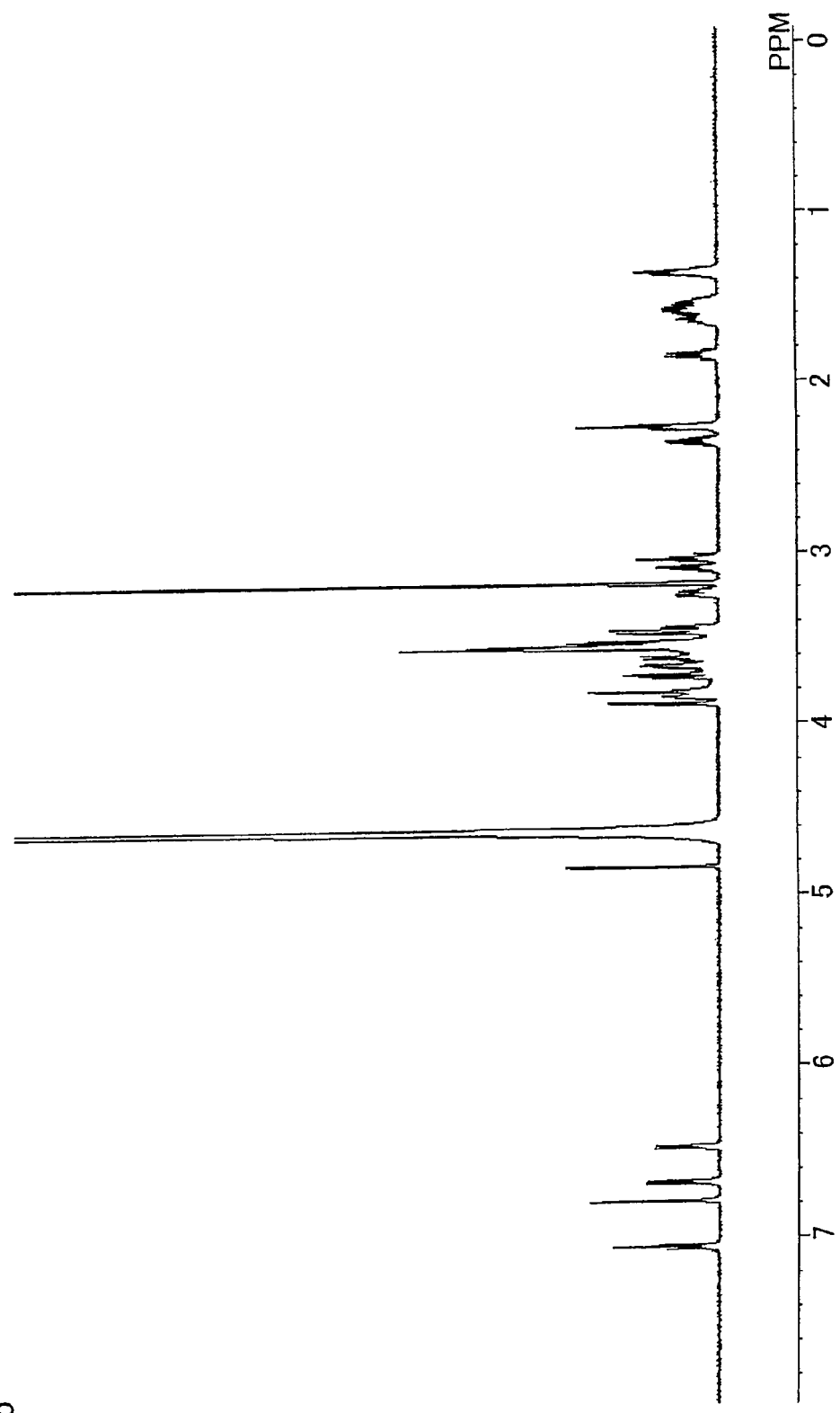
FIG. 15 is a chart of $^1$H-NM R spectroscopy analysis of a ligand conjugate (Formula (43)).

$^1$H-NMR spectroscopy of the ligand conjugate was conducted, thereby obtaining the chart shown in FIG. 15. This confirmed the structure of the ligand conjugate shown in Formula (43):

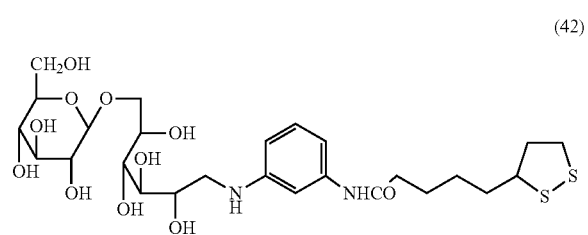

(43)

(10) Synthesis of Ligand Conjugate (Formula (44))

The ligand conjugate shown in Formula (44) was synthesized in the same manner as in (1).

Figure 16:
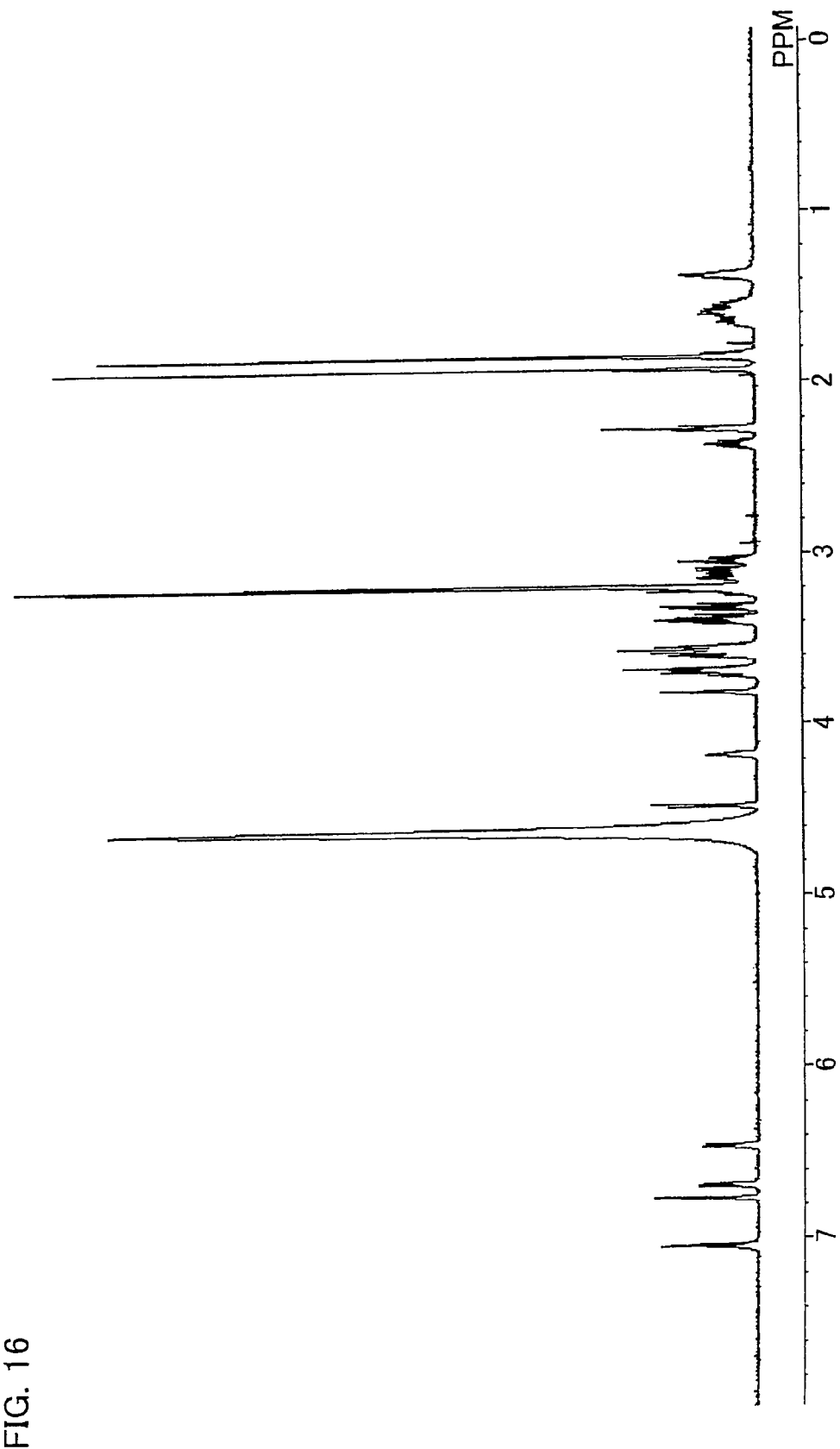
FIG. 16 is a chart of $^1$H-NMR spectroscopy analysis of a ligand conjugate (Formula (44)).

$^1$H-NMR spectroscopy of the ligand conjugate was conducted, thereby obtaining the chart shown in FIG. 16. This confirmed the structure of the ligand conjugate shown in Formula (44):

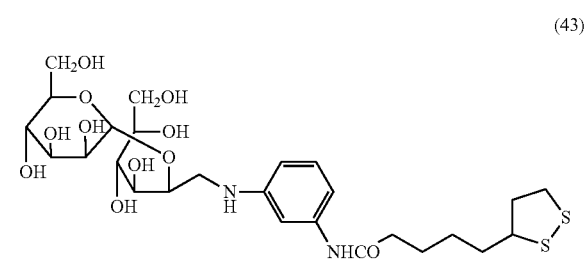

(44)

(11) Synthesis of Ligand Conjugate (Formula (45))

The ligand conjugate shown in Formula (45) was synthesized in the same manner as in (1).

Figure 17:
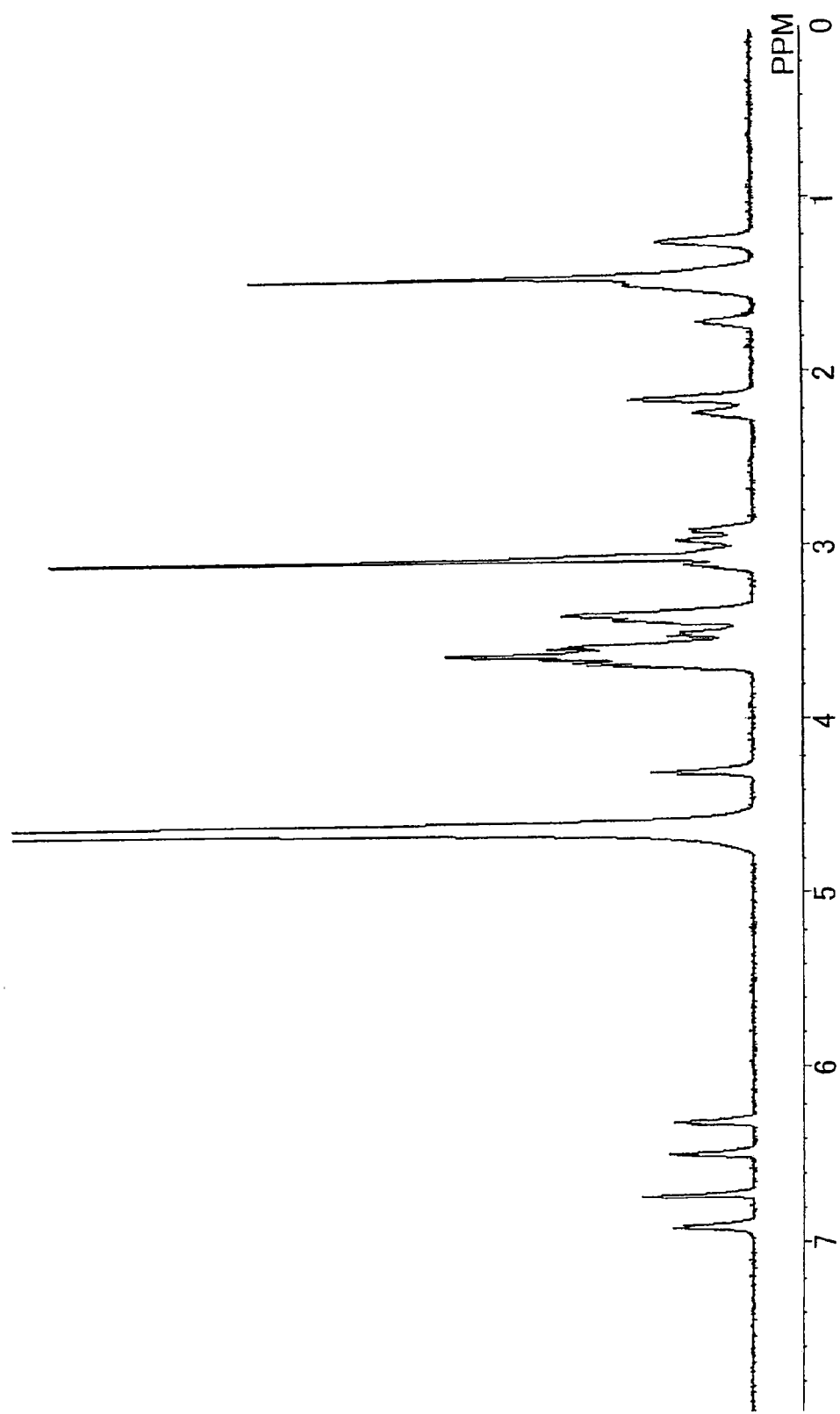
FIG. 17 is a chart of $^1$H-NMR spectroscopy analysis of a ligand conjugate (Formula (45)).

$^1$H-NMR spectroscopy of the ligand conjugate was conducted, thereby obtaining the chart shown in FIG. 17. This confirmed the structure of the ligand conjugate shown in Formula (45):

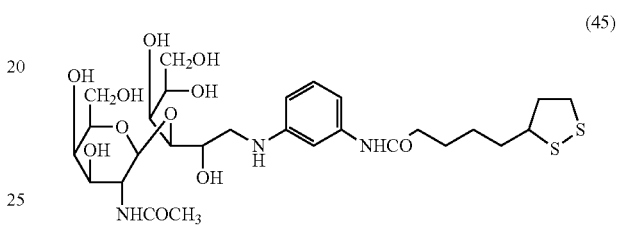

(45)

(12) Synthesis of Ligand Conjugate (Formula (46))

The ligand conjugate shown in Formula (46) was synthesized in the same manner as in (1).

Figure 18:
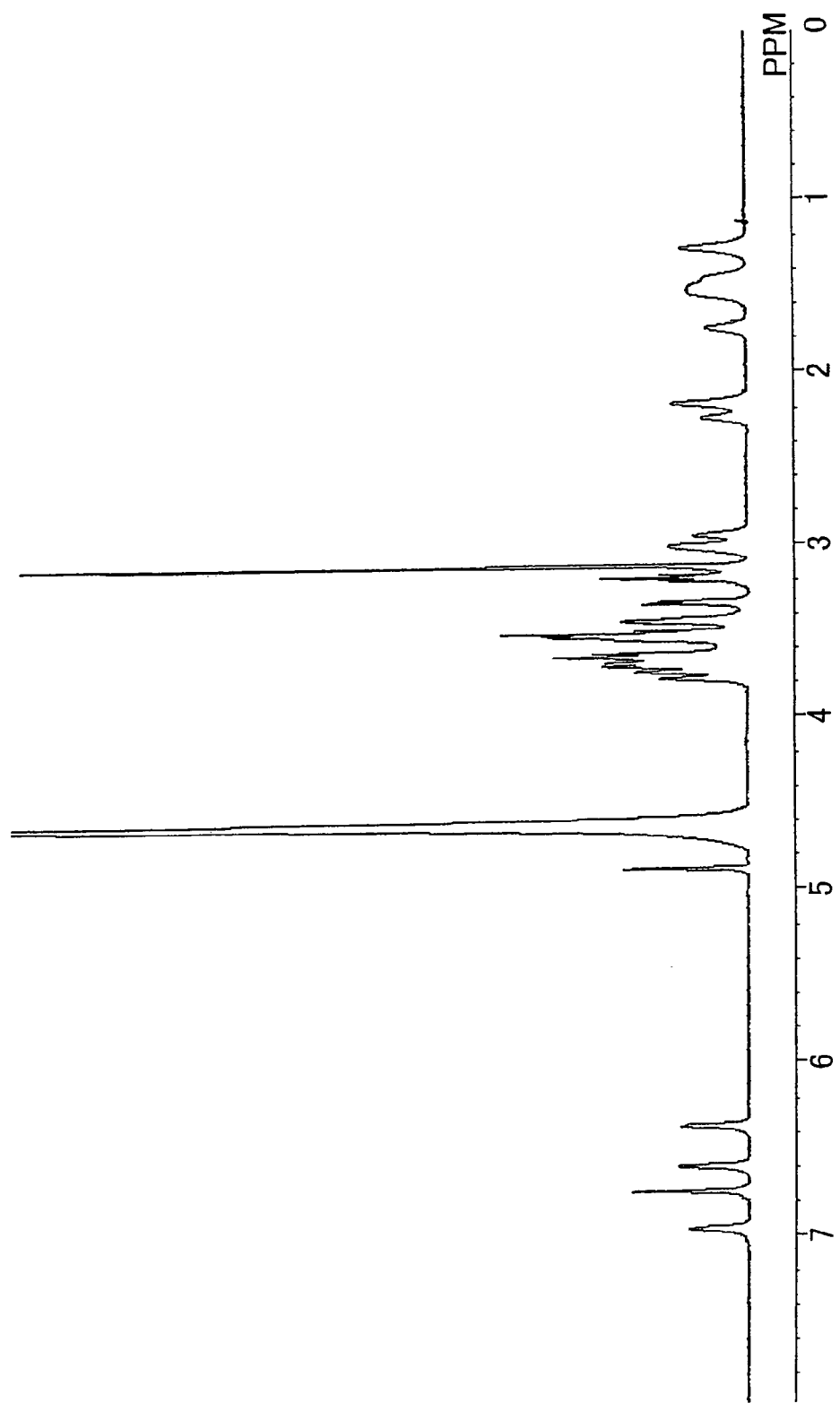
FIG. 18 is a chart of $^1$H-NMR spectroscopy analysis of a ligand conjugate (Formula (46)).

$^1$H-NMR spectroscopy of the ligand conjugate was conducted, thereby obtaining the chart shown in FIG. 18. This confirmed the structure of the ligand conjugate shown in Formula (46):

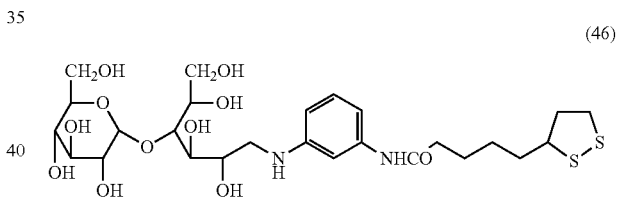

(46)

(13) Synthesis of Ligand Conjugate (Formula (47))

The ligand conjugate shown in Formula (47) was synthesized in the same manner as in (1).

Figure 19:
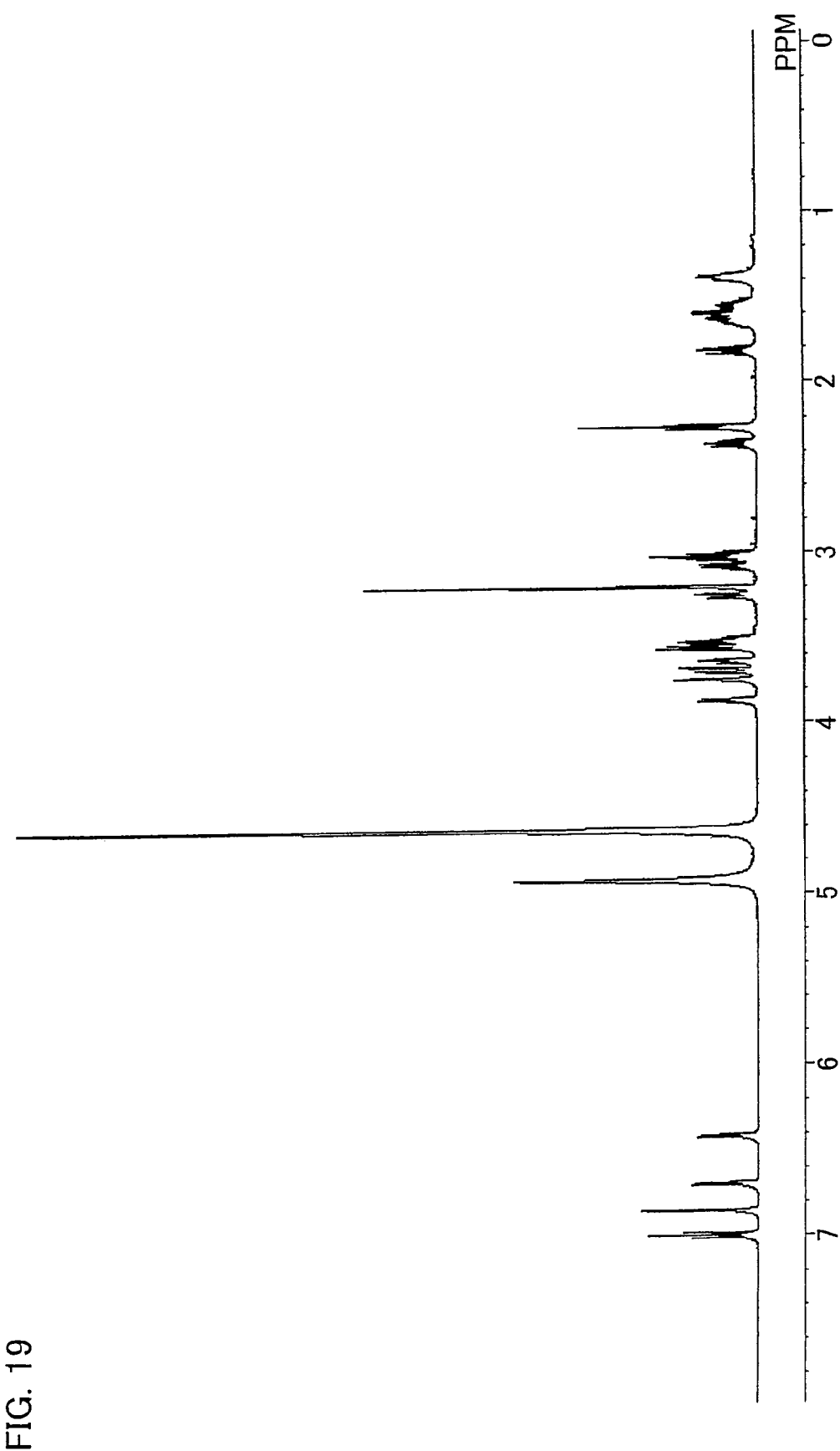
FIG. 19 is a chart of $^1$H-NMR spectroscopy analysis of a ligand conjugate (Formula (47)).

$^1$H-NMR spectroscopy of the ligand conjugate was conducted, thereby obtaining the chart shown in FIG. 19. This confirmed the structure of the ligand conjugate shown in Formula (47):

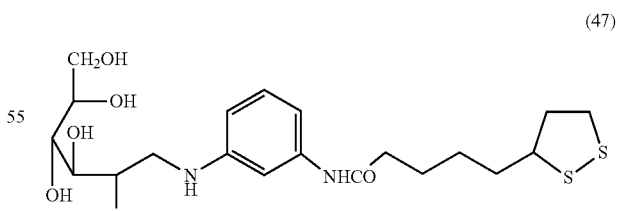

(47)

(14) Synthesis of Ligand Conjugate (Formula (48))

The ligand conjugate shown in Formula (48) was synthesized in the same manner as in (1).

Figure 20:
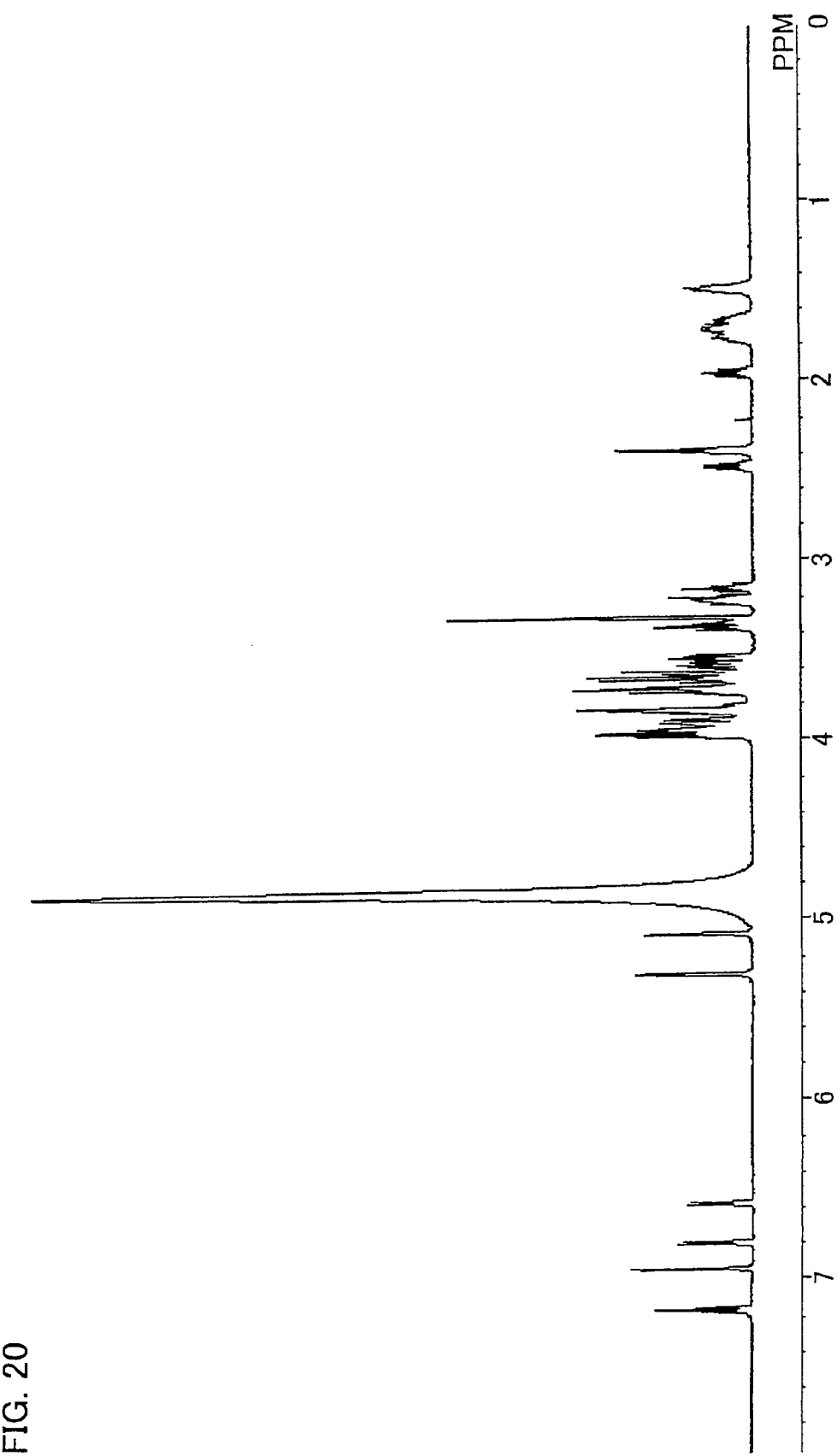
FIG. 20 is a chart of $^1$H-NMR spectroscopy analysis of a ligand conjugate (Formula (48)).

$^1$H-NMR spectroscopy of the ligand conjugate was conducted, thereby obtaining the chart shown in FIG. 20. This confirmed the structure of the ligand conjugate shown in Formula (48):

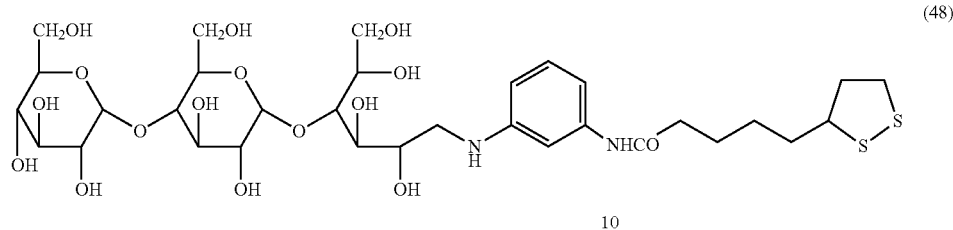

(48)

(15) Synthesis of Ligand Conjugate (Formula (49))

The ligand conjugate shown in Formula (49) was synthesized in the same manner as in (1).

Figure 21:
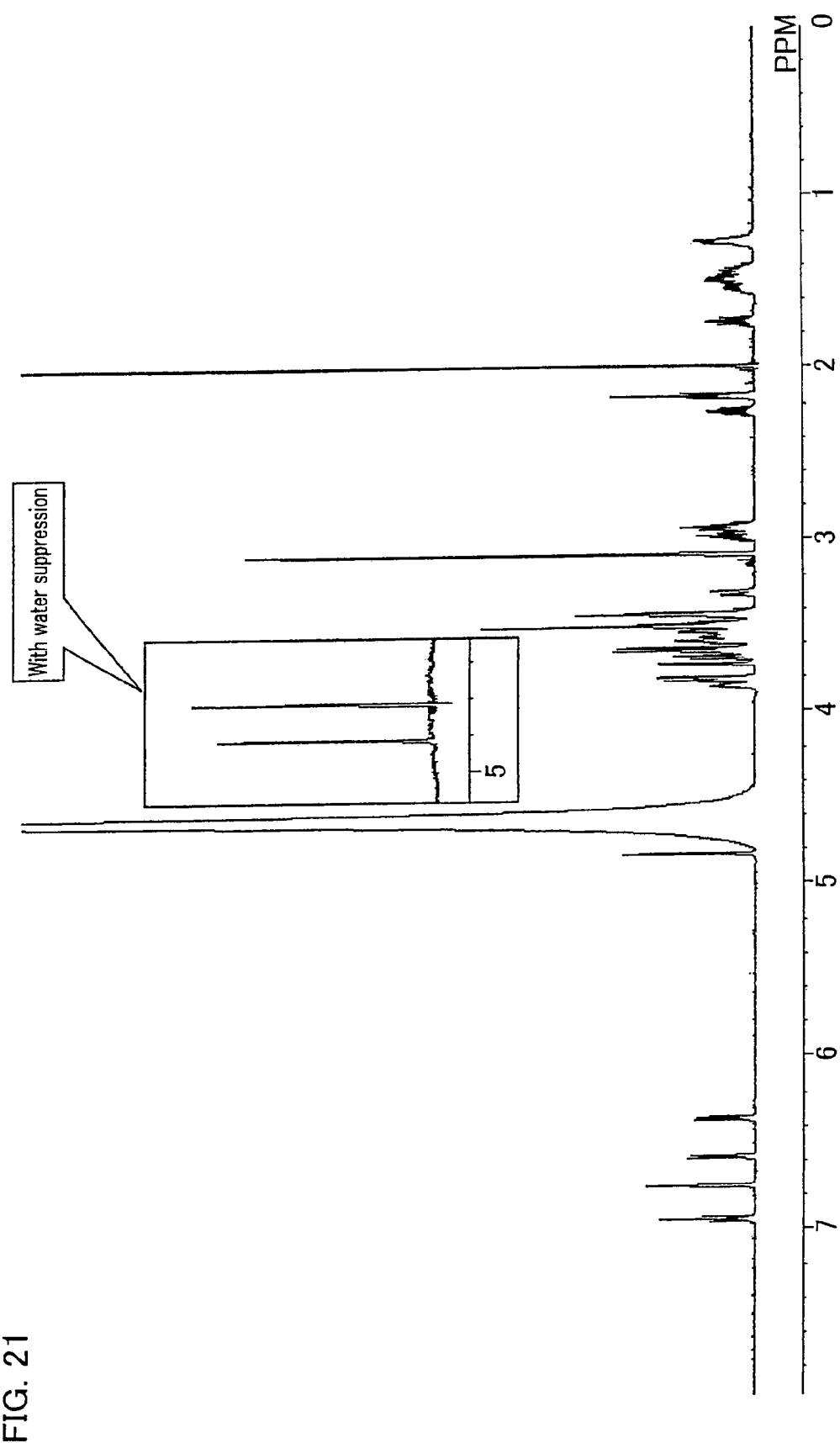
FIG. 21 is a chart of $^1$H-NMR spectroscopy analysis of a ligand conjugate (Formula (49)).

$^1$H-NMR spectroscopy of the ligand conjugate was conducted, thereby obtaining the chart shown in FIG. 21. This confirmed the structure of the ligand conjugate shown in Formula (49):

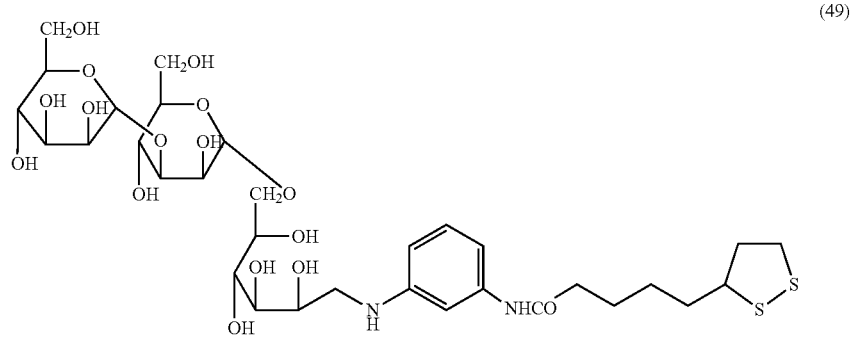

(49)

(16) Synthesis of Ligand Conjugate (Formula (50))

The ligand conjugate shown in Formula (50) was synthesized in the same manner as in (1).

Figure 22:
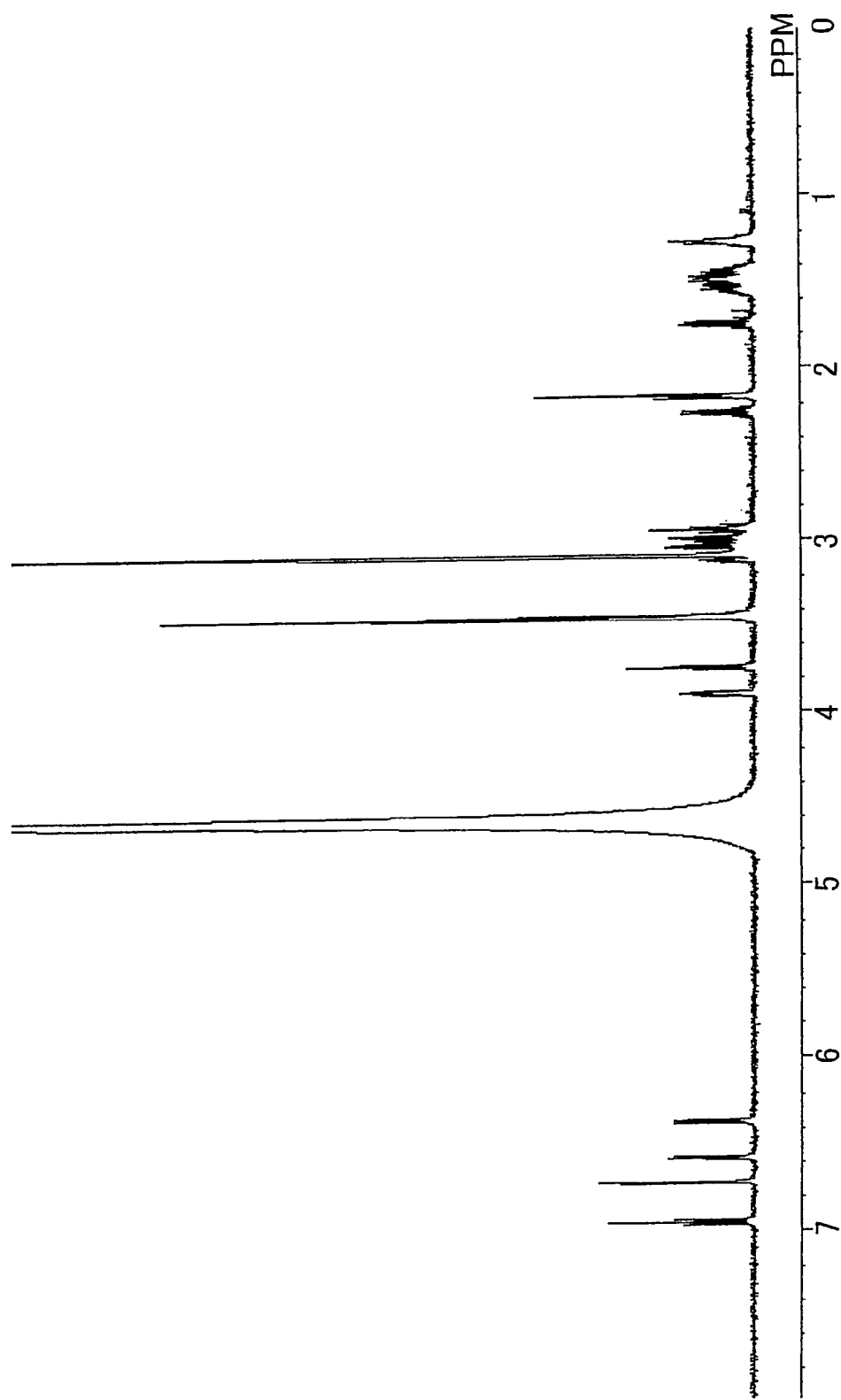
FIG. 22 is a chart of $^1$H-NMR spectroscopy analysis of a ligand conjugate (Formula (50)).

$^1$H-NMR spectroscopy of the ligand conjugate was conducted, thereby obtaining the chart shown in FIG. 22. This confirmed the structure of the ligand conjugate shown in Formula (50):

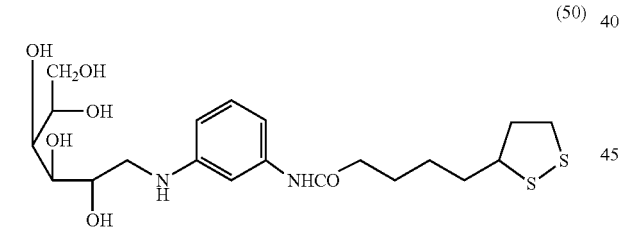

(50)

(17) Synthesis of Ligand Conjugate (Formula (51))

The ligand conjugate shown in Formula (51) was synthesized in the same manner as in (1).

Figure 23:
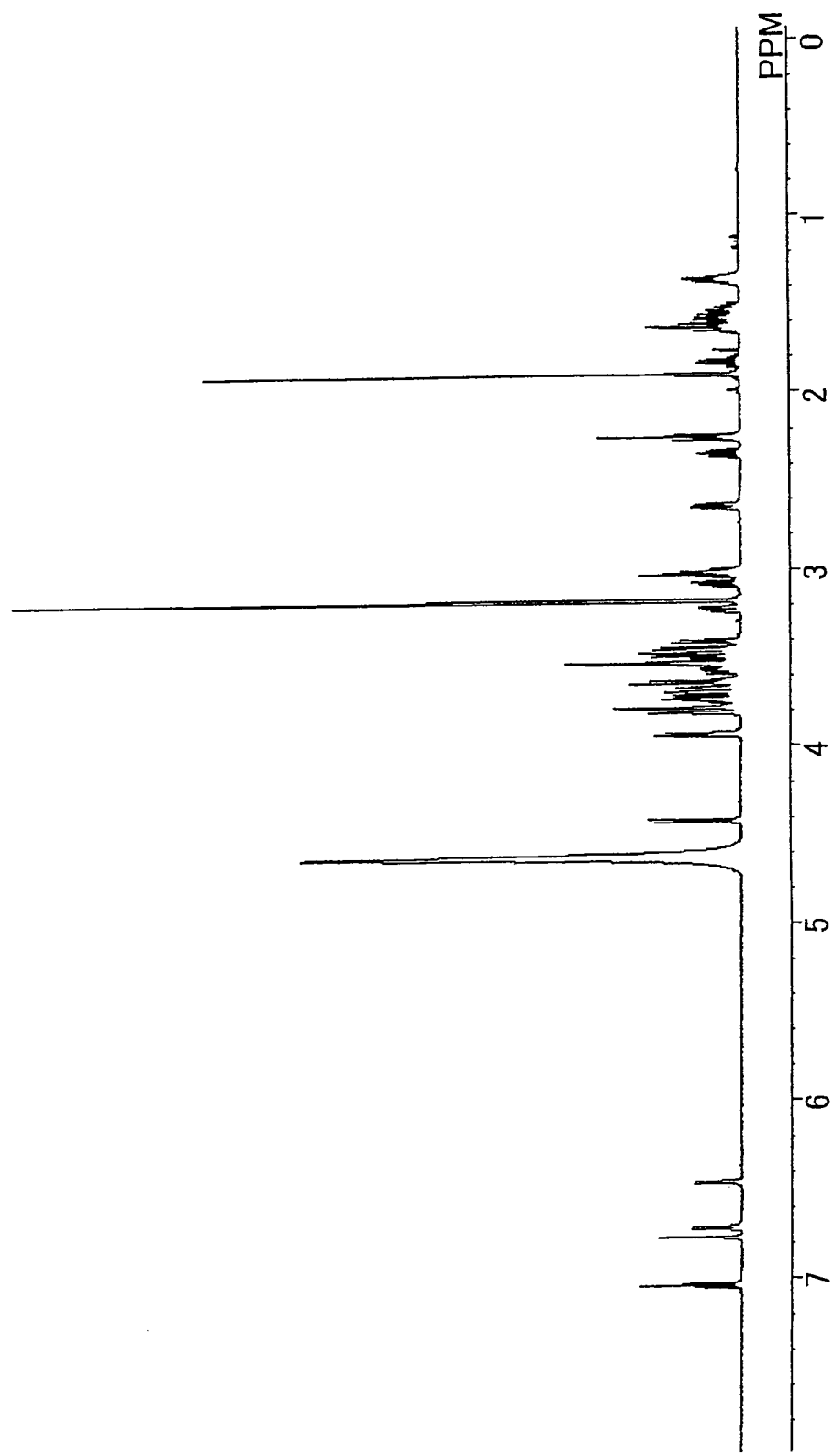
FIG. 23 is a chart of $^1$H-NMR spectroscopy analysis of a ligand conjugate (Formula (51)).

$^1$H-NMR spectroscopy of the ligand conjugate was conducted, thereby obtaining the chart shown in FIG. 23. This confirmed the structure of the ligand conjugate shown in Formula (51):

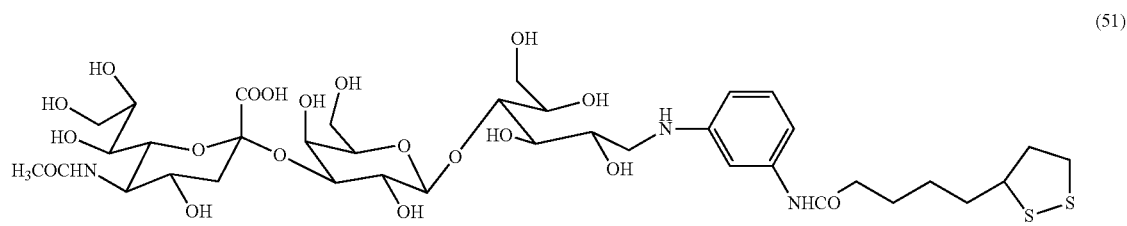

(51)

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

INDUSTRIAL APPLICABILITY

As described above, a ligand conjugate according to the present invention is capable of having a plurality of sugar chains per ligand conjugate. Thus, it is possible to have a large number of sugar molecules on a supporter surface without increasing a number of ligand conjugates introduced on the supporter surface. By using a linker compound according to the present invention, interaction between the sugar molecule and protein can be evaluated with good reproducibility.

Moreover, a ligand carrier is applicable to identification of unknown protein. Furthermore, protein analysis according to the present invention is applicable to identification of unknown protein.

The present invention provides novel ligand conjugate, ligand carrier, and the like, which are effectively applicable to functional analysis of proteins. A ligand carrier (chip) having an oligosaccharide chain immobilized thereon thereby to be developed as a tool for the functional analysis of sugars and proteins can contribute to understanding of biological phenomenon to which oligosaccharide chains relate. Further, such a ligand carrier is expected to be a technology important to pharmaceutical development. Thus, the present invention is highly useful.

The invention claimed is:
1. A ligand conjugate comprising a linker compound and a sugar chain,
the linker compound having a structure represented by General Formula (1):

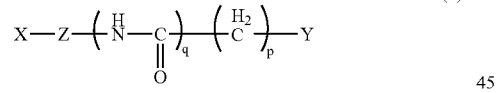

(1)

where p and q are independently integers of not less than 1 but not more than 6, in which
X is a structure represented by formula 3:

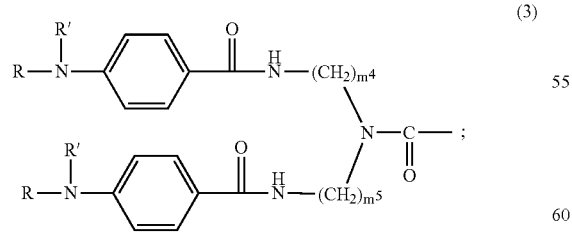

(3)

wherein $m^4$ and $m^5$ are each independently integers of not less than 1 but not more than 6, and R' is a hydrogen (H) or R,
Y is a hydrocarbon structure having an S—S bond or an S—H group,
Z is a straight-chain structure comprising a carbon-carbon bond or carbon-oxygen bond, and
R comprises a substituent derived from the sugar chain selected from the group consisting of:

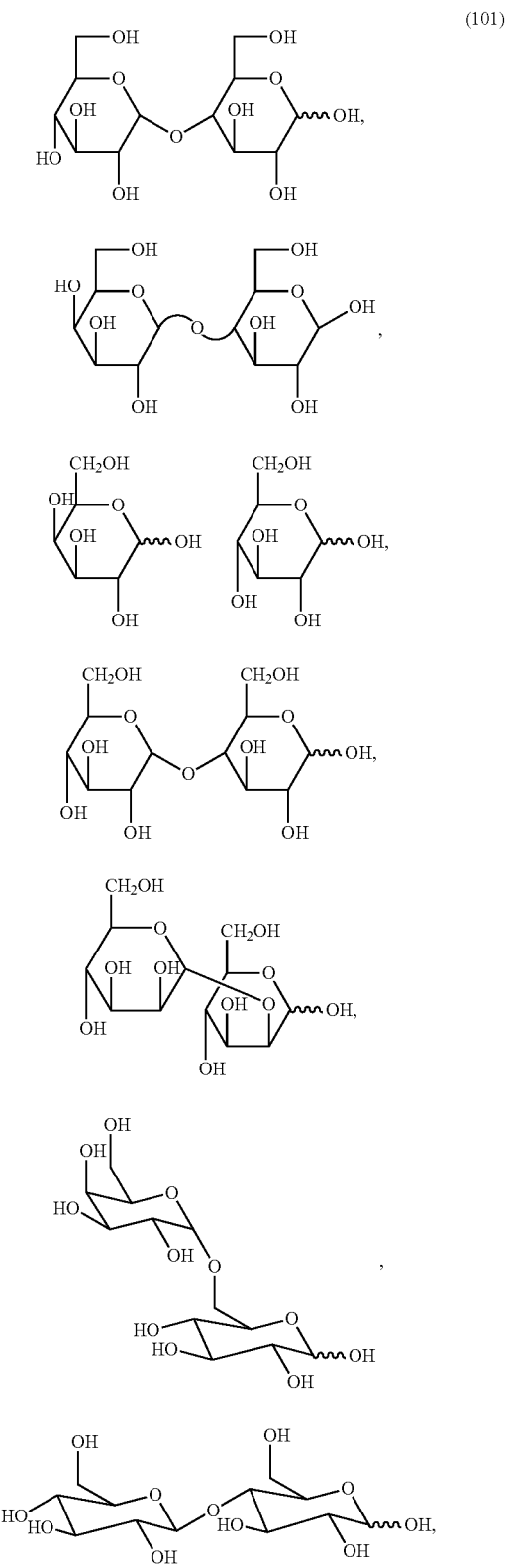

(101)

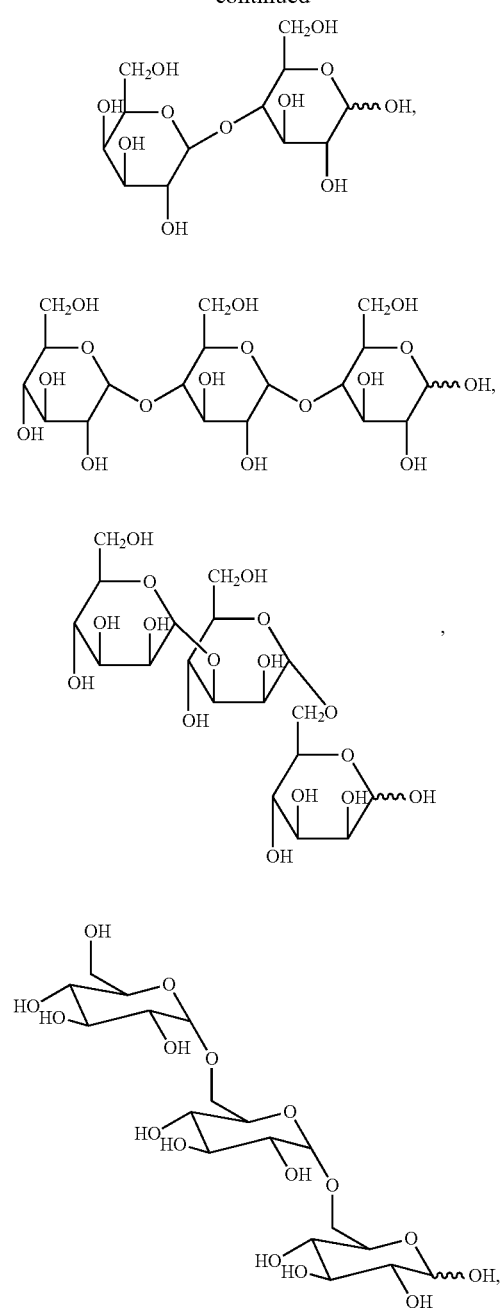
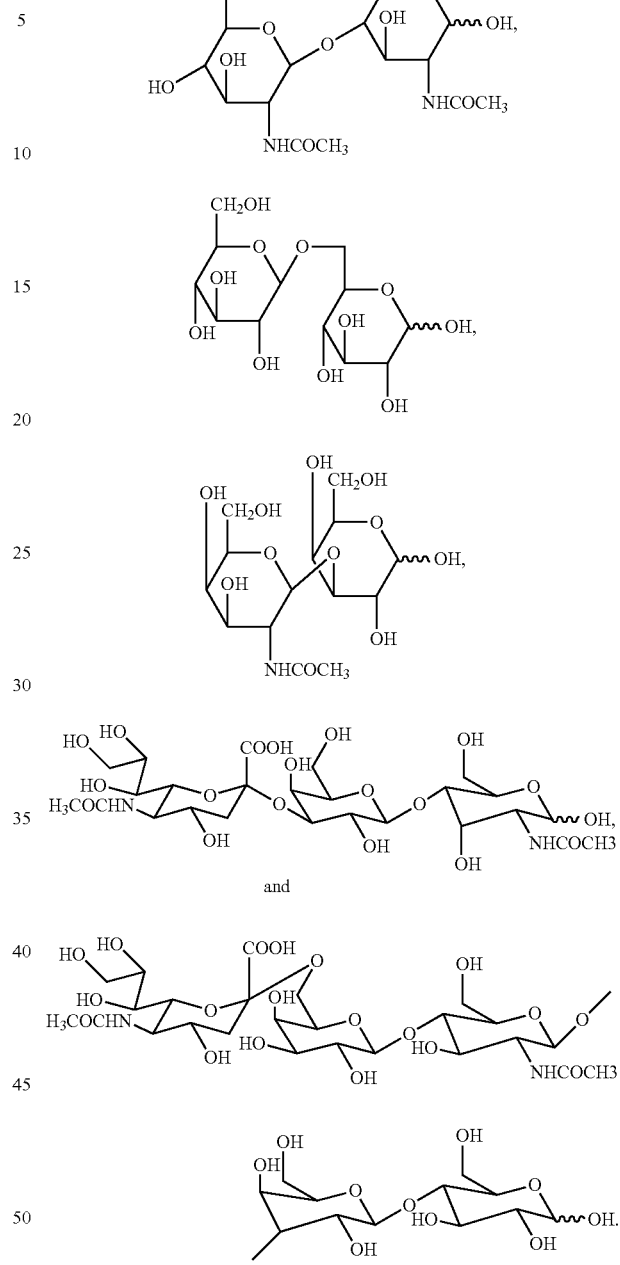
2. The ligand conjugate of claim 1, wherein:
Z has a structure of Formula (5) or (6):
 (5)
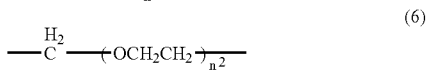 (6)
where $n^1$ and $n^2$ are independently integers of not less than 1 but not more than 6.

3. The ligand conjugate as set forth in claim 1 having a structure represented by General Formula (108):

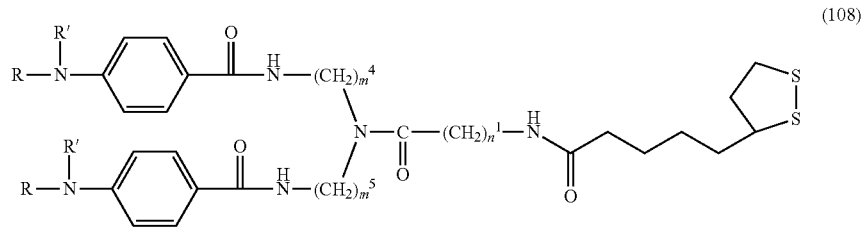

(108)

where $n^1$ is an integer of not less than 1 but not more than 6.

4. A ligand carrier in which the ligand conjugate as set forth in any one of claims 1, 2 or 3 is immobilized on a support having a metal on a surface thereof.

5. A method for analyzing protein, comprising:
allowing the ligand conjugate as set forth in any one of claim 1, 2, or 3 to come in contact with a support having a metal on a surface thereof so as to prepare a ligand carrier in which the ligand conjugate is immobilized on the support;
analyzing intermolecular interaction by surface plasmon resonance (SPR) after allowing the ligand carrier to come in contact with a protein solution; and
performing mass spectroscopy after the analysis of the intermolecular interaction, so as to identify a protein bound on the ligand carrier.

6. The ligand conjugate as set forth in claim 1, wherein $m^4$ and $m^5$ are each 2.

7. A method for analyzing protein, comprising:
allowing the ligand carrier of claim 4 to come in contact with a protein solution, and analyzing intermolecular interaction by SPR measurement.

* * * * *